US011008366B2

(12) United States Patent
Guerlavais et al.

(10) Patent No.: US 11,008,366 B2
(45) Date of Patent: *May 18, 2021

(54) PEPTIDOMIMETIC MACROCYCLES

(71) Applicant: AILERON THERAPEUTICS, INC., Watertown, MA (US)

(72) Inventors: Vincent Guerlavais, Arlington, MA (US); Noriyuki Kawahata, West Roxbury, MA (US)

(73) Assignee: AILERON THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,845

(22) Filed: Sep. 6, 2019

(65) Prior Publication Data
US 2020/0102351 A1 Apr. 2, 2020

Related U.S. Application Data

(60) Continuation of application No. 16/126,300, filed on Sep. 10, 2018, now Pat. No. 10,703,780, which is a continuation of application No. 14/460,848, filed on Aug. 15, 2014, now abandoned, which is a division of application No. 13/816,880, filed as application No. PCT/US2011/047692 on Aug. 13, 2011, now Pat. No. 8,859,723.

(60) Provisional application No. 61/374,163, filed on Aug. 16, 2010, provisional application No. 61/373,638, filed on Aug. 13, 2010, provisional application No. 61/373,701, filed on Aug. 13, 2010.

(51) Int. Cl.
| C07K 7/64 | (2006.01) |
| C07K 7/56 | (2006.01) |
| A61K 38/00 | (2006.01) |
| C07K 14/47 | (2006.01) |

(52) U.S. Cl.
CPC ............. *C07K 7/64* (2013.01); *C07K 7/56* (2013.01); *C07K 14/4746* (2013.01); *A61K 38/00* (2013.01)

(58) Field of Classification Search
None
See application file for complete search history.

(56) References Cited

U.S. PATENT DOCUMENTS

| 5,708,136 A | 1/1998 | Burrell et al. |
| 5,710,245 A | 1/1998 | Kahn |
| 5,756,669 A | 5/1998 | Bischoff et al. |
| 5,770,377 A | 6/1998 | Picksley et al. |
| 5,811,515 A | 9/1998 | Grubbs et al. |
| 5,874,529 A | 2/1999 | Gilon et al. |
| 6,153,391 A | 11/2000 | Picksley et al. |
| 6,169,073 B1 | 1/2001 | Halazonetis et al. |
| 6,177,076 B1 | 1/2001 | Lattime et al. |
| 6,420,118 B1 | 7/2002 | Halazonetis et al. |
| 6,686,148 B1 | 2/2004 | Shen et al. |
| 7,083,983 B2 | 8/2006 | Lane et al. |
| 7,084,244 B2 | 8/2006 | Gilon et al. |
| 7,115,372 B2 | 10/2006 | Shen et al. |
| 7,189,801 B2 | 3/2007 | Halazonetis et al. |
| 7,192,713 B1 | 3/2007 | Verdine et al. |
| 7,202,332 B2 | 4/2007 | Arora et al. |
| 7,638,138 B2 | 12/2009 | Oki et al. |
| 7,666,983 B2 | 2/2010 | Halazonetis et al. |
| 7,705,118 B2 | 4/2010 | Arora et al. |
| 7,723,469 B2 | 5/2010 | Walensky et al. |
| 7,759,383 B2 | 7/2010 | Wang et al. |
| 7,786,072 B2 | 8/2010 | Verdine et al. |
| 7,960,506 B2 | 6/2011 | Nash |
| 7,981,998 B2 | 7/2011 | Nash |
| 7,981,999 B2 | 7/2011 | Nash |
| 8,071,541 B2 | 12/2011 | Arora et al. |
| 8,198,405 B2 | 6/2012 | Walensky et al. |
| 8,324,428 B2 | 12/2012 | Verdine et al. |
| 8,343,760 B2 | 1/2013 | Lu et al. |
| 8,389,484 B2 | 3/2013 | Shen et al. |
| 8,399,405 B2 | 3/2013 | Nash et al. |
| 8,524,653 B2 | 9/2013 | Nash et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 * | 10/2014 | Guerlavais ............... C07K 7/56 530/321 |
| 8,871,899 B2 | 10/2014 | Wang et al. |
| 8,889,632 B2 | 11/2014 | Bernal et al. |
| 8,895,699 B2 | 11/2014 | Verdine et al. |

(Continued)

FOREIGN PATENT DOCUMENTS

| AU | 2008232709 A1 | 10/2008 |
| CA | 2700925 A1 | 4/2009 |

(Continued)

OTHER PUBLICATIONS

Abbas, et al. (2010). Mdm2 is required for survival of hematopoietic stem cells/progenitors via dampening of ROS-induced p53 activity. Cell Stem Cell 7, 606-617.
Andrews et al. Forming Stable Helical Peptide Using Natural and Artificial Amino Acids. Tetrahedron. 1999;55:11711-11743.
Bernal, et al. A stapled p53 helix overcomes HDMX-mediated suppression of p53. Cancer Cell. Nov. 16, 2010;18(5):411-22. doi: 10.1016/j.ccr.2010.10.024.
Bernal, et al. Reactivation of the p53 tumor suppressor pathway by a stapled p53 peptide. J Am Chem Soc. Mar. 7, 2007;129(9):2456-7.

(Continued)

*Primary Examiner* — Sergio Coffa
(74) *Attorney, Agent, or Firm* — Wilson Sonsini Goodrich & Rosati

(57) ABSTRACT

The present invention provides novel peptidomimetic macrocycles and methods of using such macrocycles for the treatment of disease.

11 Claims, 17 Drawing Sheets

Specification includes a Sequence Listing.

(56) References Cited

U.S. PATENT DOCUMENTS

| | | | |
|---|---|---|---|
| 8,927,500 B2 * | 1/2015 | Guerlavais | C07K 7/54 |
| | | | 514/18.9 |
| 8,987,414 B2 | 3/2015 | Guerlavais et al. | |
| 9,023,988 B2 | 5/2015 | Nash | |
| 9,096,684 B2 | 8/2015 | Kawahata et al. | |
| 9,163,330 B2 | 10/2015 | Verdine et al. | |
| 9,175,045 B2 | 11/2015 | Nash et al. | |
| 9,175,047 B2 | 11/2015 | Nash et al. | |
| 9,175,056 B2 | 11/2015 | Nash | |
| 9,206,223 B2 | 12/2015 | Nash et al. | |
| 9,273,099 B2 | 3/2016 | Walensky et al. | |
| 9,394,336 B2 | 7/2016 | Nash et al. | |
| 9,458,189 B2 | 10/2016 | Verdine et al. | |
| 9,458,202 B2 | 10/2016 | Nash et al. | |
| 9,464,115 B2 | 10/2016 | Walensky et al. | |
| 9,493,509 B2 | 11/2016 | Nash | |
| 9,505,801 B2 | 11/2016 | Verdine et al. | |
| 9,505,804 B2 | 11/2016 | Guerlavais et al. | |
| 9,522,947 B2 | 12/2016 | Kawahata et al. | |
| 9,527,896 B2 | 12/2016 | Bernal et al. | |
| 9,556,227 B2 | 1/2017 | Verdine et al. | |
| 9,604,919 B2 | 3/2017 | Darlak et al. | |
| 9,617,309 B2 | 4/2017 | Verdine et al. | |
| 9,675,661 B2 | 6/2017 | Nash | |
| 9,845,287 B2 | 12/2017 | Darlak et al. | |
| 9,951,099 B2 | 4/2018 | Verdine et al. | |
| 9,957,296 B2 | 5/2018 | Nash et al. | |
| 9,957,299 B2 | 5/2018 | Guerlavais et al. | |
| 1,002,242 A1 | 7/2018 | Nash et al. | |
| 1,002,361 A1 | 7/2018 | Guerlavais et al. | |
| 1,003,004 A1 | 7/2018 | Nash | |
| 1,005,974 A1 | 8/2018 | Annis et al. | |
| 1,020,243 A1 | 2/2019 | Bernal et al. | |
| 1,021,347 A1 | 2/2019 | Guerlavais et al. | |
| 1,022,738 A1 | 3/2019 | Guerlavais et al. | |
| 1,024,649 A1 | 4/2019 | Guerlavais et al. | |
| 1,025,306 A1 | 4/2019 | Chen et al. | |
| 1,030,010 A1 | 5/2019 | Nash et al. | |
| 1,030,135 A1 | 5/2019 | Verdine et al. | |
| 1,030,869 A1 | 6/2019 | Kawahata et al. | |
| 1,032,811 A1 | 6/2019 | Nash | |
| 1,046,497 A1 | 11/2019 | Walensky et al. | |
| 1,047,112 A1 | 11/2019 | Chen et al. | |
| 1,048,711 A1 | 11/2019 | Verdine et al. | |
| 2002/0098580 A1 | 7/2002 | Nandabalan et al. | |
| 2002/0132977 A1 | 9/2002 | Yuan et al. | |
| 2003/0060432 A1 | 3/2003 | Tocque et al. | |
| 2003/0144331 A1 | 7/2003 | Gudkov et al. | |
| 2003/0176318 A1 | 9/2003 | Gudkov et al. | |
| 2004/0146971 A1 | 7/2004 | Lane et al. | |
| 2005/0137137 A1 | 6/2005 | Lane et al. | |
| 2005/0227932 A1 | 10/2005 | Lu et al. | |
| 2005/0250680 A1 | 11/2005 | Walensky et al. | |
| 2006/0008848 A1 | 1/2006 | Verdine et al. | |
| 2006/0014675 A1 | 1/2006 | Arora et al. | |
| 2007/0197772 A1 | 8/2007 | Arora et al. | |
| 2008/0161426 A1 | 7/2008 | Gudkov et al. | |
| 2008/0262200 A1 | 10/2008 | Nash | |
| 2009/0047711 A1 | 2/2009 | Nash | |
| 2009/0088553 A1 | 4/2009 | Nash | |
| 2009/0149630 A1 | 6/2009 | Walensky et al. | |
| 2009/0176964 A1 | 7/2009 | Walensky et al. | |
| 2009/0221512 A1 | 9/2009 | Acosta et al. | |
| 2009/0275519 A1 | 11/2009 | Nash et al. | |
| 2009/0326192 A1 * | 12/2009 | Nash | G01N 33/68 |
| | | | 530/317 |
| 2010/0081611 A1 | 4/2010 | Bradner et al. | |
| 2010/0093086 A1 | 4/2010 | Lin et al. | |
| 2010/0168388 A1 | 7/2010 | Bernal et al. | |
| 2010/0184628 A1 | 7/2010 | Nash | |
| 2010/0184645 A1 | 7/2010 | Verdine et al. | |
| 2010/0210515 A1 | 8/2010 | Nash et al. | |
| 2010/0216688 A1 | 8/2010 | Nash et al. | |
| 2010/0234563 A1 | 9/2010 | Arora et al. | |
| 2010/0273704 A1 | 10/2010 | Korsmeyer et al. | |
| 2010/0298201 A1 | 11/2010 | Nash et al. | |
| 2011/0028753 A1 | 2/2011 | Verdine et al. | |
| 2011/0144303 A1 | 6/2011 | Nash et al. | |
| 2011/0144306 A1 | 6/2011 | Verdine et al. | |
| 2011/0223149 A1 | 9/2011 | Nash et al. | |
| 2011/0245175 A1 | 10/2011 | Arora et al. | |
| 2011/0245459 A1 | 10/2011 | Marsault et al. | |
| 2011/0250685 A1 | 10/2011 | Nash | |
| 2011/0263815 A1 | 10/2011 | Nash | |
| 2012/0040889 A1 | 2/2012 | Nash et al. | |
| 2012/0082636 A1 | 4/2012 | Walensky et al. | |
| 2012/0101047 A1 | 4/2012 | Nash et al. | |
| 2012/0115783 A1 | 5/2012 | Nash et al. | |
| 2012/0115793 A1 | 5/2012 | Nash et al. | |
| 2012/0149648 A1 | 6/2012 | Nash et al. | |
| 2012/0165566 A1 | 6/2012 | Marsault et al. | |
| 2012/0172311 A1 | 7/2012 | Nash et al. | |
| 2012/0178700 A1 | 7/2012 | Nash et al. | |
| 2012/0190818 A1 | 7/2012 | Nash | |
| 2012/0226066 A1 | 9/2012 | Marsault et al. | |
| 2012/0226067 A1 | 9/2012 | Marsault et al. | |
| 2012/0226072 A1 | 9/2012 | Marsault et al. | |
| 2012/0264674 A1 | 10/2012 | Nash et al. | |
| 2012/0270800 A1 | 10/2012 | Verdine et al. | |
| 2012/0328692 A1 | 12/2012 | Lu et al. | |
| 2013/0005943 A1 | 1/2013 | Arora et al. | |
| 2013/0023646 A1 | 1/2013 | Nash et al. | |
| 2013/0072439 A1 | 3/2013 | Nash et al. | |
| 2013/0123196 A1 | 5/2013 | Arora et al. | |
| 2013/0210743 A1 | 8/2013 | Guerlavais et al. | |
| 2013/0210745 A1 | 8/2013 | Guerlavais et al. | |
| 2013/0211046 A1 | 8/2013 | Verdine et al. | |
| 2013/0274205 A1 | 10/2013 | Guerlavais et al. | |
| 2014/0005118 A1 | 1/2014 | Verdine et al. | |
| 2014/0018302 A1 | 1/2014 | Walensky et al. | |
| 2014/0051828 A1 | 2/2014 | Arora et al. | |
| 2014/0162339 A1 | 6/2014 | Verdine et al. | |
| 2014/0296160 A1 | 10/2014 | Walensky et al. | |
| 2014/0323701 A1 | 10/2014 | Nash et al. | |
| 2014/0378390 A1 | 12/2014 | Guerlavais et al. | |
| 2015/0038430 A1 | 2/2015 | Nash et al. | |
| 2015/0051155 A1 | 2/2015 | Guerlavais et al. | |
| 2015/0056612 A1 | 2/2015 | Shen et al. | |
| 2015/0119551 A1 | 4/2015 | Bernal et al. | |
| 2016/0068573 A1 | 3/2016 | Nash et al. | |
| 2016/0095896 A1 | 4/2016 | Nash et al. | |
| 2016/0096873 A1 | 4/2016 | Nash et al. | |
| 2016/0101145 A1 | 4/2016 | Annis et al. | |
| 2016/0108089 A1 | 4/2016 | Nash et al. | |
| 2016/0115204 A1 | 4/2016 | Nash et al. | |
| 2016/0215036 A1 | 7/2016 | Verdine et al. | |
| 2016/0244494 A1 | 8/2016 | Verdine et al. | |
| 2016/0250278 A1 | 9/2016 | Nash et al. | |
| 2016/0251399 A1 | 9/2016 | Nash et al. | |
| 2016/0257716 A1 | 9/2016 | Guerlavais et al. | |
| 2016/0257725 A1 | 9/2016 | Verdine et al. | |
| 2016/0287569 A1 | 10/2016 | Caenepeel et al. | |
| 2016/0289274 A1 | 10/2016 | Nash | |
| 2017/0002042 A1 | 1/2017 | Annis et al. | |
| 2017/0008930 A1 | 1/2017 | Walensky et al. | |
| 2017/0037086 A1 | 2/2017 | Kawahata et al. | |
| 2017/0037105 A1 | 2/2017 | Samant | |
| 2017/0088581 A1 | 3/2017 | Verdine et al. | |
| 2017/0107252 A1 | 4/2017 | Guerlavais et al. | |
| 2017/0114098 A1 | 4/2017 | Aivado et al. | |
| 2017/0212125 A1 | 7/2017 | Nash et al. | |
| 2017/0298099 A1 | 10/2017 | Nash et al. | |
| 2017/0349638 A1 | 12/2017 | Aivado | |
| 2017/0360881 A1 | 12/2017 | Samant et al. | |
| 2018/0085426 A1 | 3/2018 | Nash et al. | |
| 2018/0100001 A1 | 4/2018 | Verdine et al. | |
| 2018/0265459 A1 | 9/2018 | Darlak et al. | |

FOREIGN PATENT DOCUMENTS

| | | |
|---|---|---|
| CN | 1906209 A | 1/2007 |
| CN | 101636407 A | 1/2010 |
| CN | 102223891 A | 10/2011 |
| EP | 0977580 B1 | 4/2003 |

(56) References Cited

FOREIGN PATENT DOCUMENTS

| | | |
|---|---|---|
| EP | 0958305 B1 | 6/2008 |
| EP | 2091552 A2 | 8/2009 |
| EP | 2310407 A2 | 4/2011 |
| EP | 2488193 A1 | 8/2012 |
| EP | 2489360 A1 | 8/2012 |
| EP | 2114428 B1 | 10/2012 |
| EP | 2637680 A2 | 9/2013 |
| JP | 2008501623 A | 1/2008 |
| JP | 2010518017 A | 5/2010 |
| JP | 2010120881 A | 6/2010 |
| JP | 2010519318 A | 6/2010 |
| JP | 2012503025 A | 2/2012 |
| WO | WO-2005044839 A2 | 5/2005 |
| WO | WO-2005040202 A3 | 6/2005 |
| WO | WO-2005044839 A3 | 7/2005 |
| WO | WO-2005118620 A2 | 12/2005 |
| WO | WO-2005118620 A3 | 6/2006 |
| WO | WO-2006137974 A3 | 4/2007 |
| WO | WO-2008061192 A2 | 5/2008 |
| WO | WO-2008076904 A1 | 6/2008 |
| WO | WO-2008061192 A3 | 7/2008 |
| WO | WO-2008095063 A1 | 8/2008 |
| WO | WO-2008121767 A2 | 10/2008 |
| WO | WO-2008104000 A3 | 11/2008 |
| WO | WO-2008137633 A2 | 11/2008 |
| WO | WO-2008121767 A3 | 1/2009 |
| WO | WO-2009099677 A2 | 8/2009 |
| WO | WO-2009110952 A2 | 9/2009 |
| WO | WO-2009126292 A2 | 10/2009 |
| WO | WO 2009/149339 * | 12/2009 |
| WO | WO-2009149214 A2 | 12/2009 |
| WO | WO-2009149339 A2 | 12/2009 |
| WO | WO-2010011313 A2 | 1/2010 |
| WO | WO-2010013011 A1 | 2/2010 |
| WO | WO-2010033617 A2 | 3/2010 |
| WO | WO-2010033879 A2 | 3/2010 |
| WO | WO-2010034026 A1 | 3/2010 |
| WO | WO-2010034028 A1 | 3/2010 |
| WO | WO-2010034029 A1 | 3/2010 |
| WO | WO-2010034031 A1 | 3/2010 |
| WO | WO-2010034032 A1 | 3/2010 |
| WO | WO-2010034034 A1 | 3/2010 |
| WO | WO-2010058819 A1 | 5/2010 |
| WO | WO-2010060112 A1 | 5/2010 |
| WO | WO-2010083347 A2 | 7/2010 |
| WO | WO-2010011313 A3 | 12/2010 |
| WO | WO-2011005219 A1 | 1/2011 |
| WO | WO-2011008260 A2 | 1/2011 |
| WO | WO-2011008260 A3 | 3/2011 |
| WO | WO-2011038049 A1 | 3/2011 |
| WO | WO-2011047215 A1 | 4/2011 |
| WO | WO-2011106650 A2 | 9/2011 |
| WO | WO-2012012352 A2 | 1/2012 |
| WO | WO-2012021874 A1 | 2/2012 |
| WO | WO-2012021875 A1 | 2/2012 |
| WO | WO-2012021876 A2 | 2/2012 |
| WO | WO-2012033525 A2 | 3/2012 |
| WO | WO-2012122059 A1 | 9/2012 |
| WO | WO-2012173846 A2 | 12/2012 |
| WO | WO-2013036208 A1 | 3/2013 |
| WO | WO-2013062923 A1 | 5/2013 |
| WO | WO-2014052647 A2 | 4/2014 |
| WO | WO-2014055564 A1 | 4/2014 |

OTHER PUBLICATIONS

Blackwell, et al. Highly Efficient Synthesis of Covalently Cross-Linked Peptide Helices by Ring-Closing Metathesis. Angewandte Chemie International Edition. 1998; 37(23):3281-3284.
Blackwell, et al. Ring-closing metathesis of olefinic peptides: design, synthesis, and structural characterization of macrocyclic helical peptides. J Org Chem. Aug. 10, 2001;66(16):5291-302.
Blaser, et al., "The facile synthesis of a series of tryptophan derivatives", Tetrahedron Letters 49 (2008) 2795-2798.

Bo, M.D., et al. (2010). MDM4 (MDMX) is overexpressed in chronic lymphocytic leukaemia (CLL) and marks a subset of p53wild-type CLL with a poor cytotoxic response to Nutlin-3. Br J Haematol 150, 237-239.
Boguslavsky, et al. Effect of peptide conformation on membrane permeability. J Pept Res. Jun. 2003;61(6):287-97.
Bottger, et al. Molecular characterization of the hdm2-p53 interaction. J Mol Biol. Jun. 27, 1997;269(5):744-56.
Bueso-Ramos, et al. (1993). The human MDM-2 oncogene is overexpressed in leukemias. Blood 82, 2617-2623.
Chène et al., "Study of the Cytotoxic Effect of a Peptidic Inhibitor of the p53-hdm2 Interaction in Tumor Cells," FEBS Lett. 529:293-297 (2002).
Chène, P., "Inhibiting the p53-MDM2 Interaction: An Important Target for Cancer Therapy," Nat Rev. Cancer 3:102-109 (2003).
Database: Genpept, Accession No. AAS47564.1, "mixed type I polyketide synthase/nonribosomal peptide synthetase [symbiont bacterium of Paederus fuscipes]", Submitted (Jun. 19, 2003).
Final Office Action dated Jan. 17, 2014 for U.S. Appl. No. 13/816,880.
Final Office Action dated Jan. 13, 2020 for U.S. Appl. No. 16/126,300.
Fischer, et al. Apoptosis-based therapies and drug targets. Cell Death and Differentiation. 2005; 12:942-961.
Fischer, P. Peptide, Peptidomimetic, and Small-molecule Antagonists of the p53-HDM2 Protein-Protein Interaction. Int J Pept Res Ther. Mar. 2006;12(1):3-19. Epub Mar. 15, 2006.
Gante, Peptidomimetics—Tailored Enzyme Inhibitors. J Angew Chem Int Ed Engl. 1994;33:1699-1720.
García-Echeverría et al., "Discovery of Potent Antagonists of the Interaction between Human Double Minute 2 and Tumor Suppressor p53," J. Med. Chem. 43:3205-3208 (2000).
Giannis et aL, Peptidomimetics for Receptor Ligands—Discovery, Development, and Medical Perspectives. Angew Chem Int Ed Engl. 1993;32:1244-67.
Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285.2010.00951.x.
Haupt, et al. (1997). Mdm2 promotes the rapid degradation of p53. Nature 387, 296-299.
Hu, et al. Efficient p53 activation and apoptosis by simultaneous disruption of binding to MDM2 and Mdmx. Cancer Res. Sep. 15, 2007;67(18):8810-7.
International search report and written opinion dated Oct. 12, 2011 for PCT/US2011/047692.
International Search Report and Written Opinion for PCT/US2013/062929, dated Jan. 30, 2014 (H0824.70126W000).
Jones, et al. (1998). Overexpression of Mdm2 in mice reveals a p53-independent role for Mdm2 in tumorigenesis. Proc Natl Acad Sci U S A 95, 15608-15612.
Kallen, et al. Crystal structures of human MdmX(HdmX) in complex with p53 peptide analogues reveal surprising conformational changes. Journal of Biological Chemistry. Mar. 27, 2009; 284:8812-8821.
Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.
Kotha et al., Modification of constrained peptides by ring-closing metathesis reaction. Bioorg Med Chem Lett. Jun. 4, 2001;11(11):1421-3.
Kritzer et al., "Helical β-Peptide Inhibitors of the p53-hDM2 Interaction," J. Am. Chem. Soc. 126:9468-9469 (2004).
Kubbutat, et al. Regulation of p53 stability by Mdm2. Nature. May 15, 1997;387(6630):299-303.
Kussie et al, "Structure of the MDM2 Oncoprotein Bound to the p53 Tumor Suppressor Transactivation Domain," Science 274:948-953 (1996).

(56) References Cited

OTHER PUBLICATIONS

Liskamp, et al. Conformationally restricted amino acids and dipeptides, (non)peptidomimetics and secondary structure mimetics. Recl Travl Chim Pays-Bas. 1994; 113:1-19.
Lu, et al. Proteomimetic libraries: design, synthesis, and evaluation of p53-MDM2 interaction inhibitors. J Comb Chem. May-Jun. 2006;8(3):315-25.
Madden, et al. Synthesis of cell-permeable stapled peptide dual inhibitors of the p53-Mdm2/Mdmx interactions via photoinduced cycloaddition. Bioorg Med Chem Lett. Mar. 1, 2011;21(5):1472-5. doi: 10.1016/j.bmcl.2011.01.004. Epub Jan. 7, 2011.
Miller et al., Application of Ring-Closing Metathesis to the Synthesis of Rigidified Amino Acids and Peptides. J Am Chem Soc. 1996;118(40):9606-9614.
Murray, et al. Targeting protein-protein interactions: lessons from p53/MDM2. Biopolymers. 2007;88(5):657-86.
Nahi, et al. Mutated and non-mutated TP53 as targets in the treatment of leukaemia. Br J Haematol. May 2008;141(4):445-53.
Non-Final Office Action dated Jun. 28, 2019 for U.S. Appl. No. 16/126,300.
Notice of Allowance dated May 27, 2014 for U.S. Appl. No. 13/816,880.
Office action dated Jan. 3, 2013 for U.S. Appl. No. 12/593,384.
Office action dated Mar. 3, 2017 for U.S. Appl. No. 14/460,848.
Office action dated Apr. 10, 2015 for U.S. Appl. No. 14/460,848.
Office action dated Jun. 19, 2017 for U.S. Appl. No. 15/135,098.
Office action dated Oct. 10, 2013 for U.S. Appl. No. 13/816,880.
Office action dated Oct. 26, 2015 for U.S. Appl. No. 14/460,848.
Office action dated Oct. 26, 2017 for U.S. Appl. No. 14/460,848.
Office action dated Nov. 24, 2017 for U.S. Appl. No. 15/135,098.
Patgiri, et al. A hydrogen bond surrogate approach for stabilization of short peptide sequences in alpha-helical conformation. Acc Chem Res. Oct. 2008;41(10):1289-300. Epub Jul. 17, 2008.
Pazgier, et al. Structural basis for high-affinity peptide inhibition of p53 interactions with MDM2 and MDMX. Proc Natl Acad Sci U S A. Mar. 24, 2009;106(12):4665-70. doi: 10.1073/pnas.0900947106. Epub Mar. 2, 2009.
Peller, et al. (2003). TP53 in hematological cancer: low incidence of mutations with significant clinical relevance. Hum Mutat 21, 277-284.
Pellois et al., Semisynthetic proteins in mechanistic studies: using chemistry to go where nature can't. Curr Opin Chem Biol. Oct. 2006;10(5):487-91. Epub Aug. 28, 2006.
Phan, et al. Structure-based design of high affinity peptides inhibiting the interaction of p53 with MDM2 and MDMX. J Biol Chem. Jan. 15, 2010;285(3):2174-83. doi: 10.1074/jbc.M109.073056. Epub Nov. 12, 2009.
Phelan, et al. A General Method for Constraining Short Peptides to an α-Helical Conformation. J. Am. Chem. Soc. 1997;119:455-460.0.
Picksley et al., Immunochemical analysis of the interaction of p53 with MDM2;—fine mapping of the MDM2 binding site on p53 using synthetic peptides. Oncogene. Sep. 1994;9(9):2523-9.
Roof, et al. Mechanism of action and structural requirements of constrained peptide inhibitors of RGS proteins. Chem Biol Drug Des. Apr. 2006;67(4):266-74.
Schafmeister et al. An all-hydrocarbon crosslinking system for enhancing the helicity and metabolic stability of peptides. J. Am Chem. Soc. 2000;122:5891-5892.
Schmiedeberg et al. Reversible backbone protection enables combinatorial solid-phase ring-closing metathesis reaction (RCM) in peptides. Org Lett. Jan. 10, 2002;4(1):59-62.
Shangary, et al. Targeting the MDM2-p53 interaction for cancer therapy. Clin Cancer Res. Sep. 1, 2008;14(17):5318-24. doi: 10.1158/1078-0432.CCR-07-5136.
Shvarts, et al. (1996). MDMX: a novel p53-binding protein with some functional properties of MDM2. EMBO J 15, 5349-5357.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S39.
Stad, et al. (2000). Hdmx stabilizes Mdm2 and p53. J Biol Chem 275, 28039-28044.
Stad, et al. (2001). Mdmx stabilizes p53 and Mdm2 via two distinct mechanisms. EMBO Rep 2, 1029-1034.
Tanimura, et al. (1999). MDM2 interacts with MDMX through their Ring finger domains. FEBS Lett 447, 5-9.
Taylor. The synthesis and study of side-chain lactam-bridged peptides. Biopolymers. 2002;66(1):49-75.
Toniolo, Conformationally restricted peptides through short-range cyclizations. Int J Pept Protein Res. Apr. 1990;35(4):287-300.
Tyndall et al. Macrocycles mimic the extended peptide conformation recognized by aspartic, serine, cysteine and metallo proteases. Curr Med Chem. Jul. 2001;8(8):893-907.
Uesugi et al., The alpha-helical FXXPhiPhi motif in p53: TAF interaction and discrimination by MDM2. Proc Natl Acad Sci U S A. Dec. 21, 1999;96(26):14801-6.
U.S. Appl. No. 14/460,848 Office Action dated Jun. 11, 2018.
U.S. Appl. No. 15/135,098 Notice of Allowance dated Jan. 25, 2018.
Vassilev, et al. In Vivo Activation of the p53 Pathway by Small-molecule Antagonists of MDM2. Science. 2004; 303:844-848.
Xiong, et al. (2010). Spontaneous tumorigenesis in mice overexpressing the p53-negative regulator Mdm4. Cancer Res 70, 7148-7154.
Zhao, et al. (2010). p53 loss promotes acute myeloid leukemia by enabling aberrant self-renewal. Genes Dev 24, 1389-1402.

\* cited by examiner

FIG. 6A

| SP# | MW | Sequence | SJSA-1 Cell viability EC50 (µM) serum free 24h | 72h | Competition ELISA IC50 (nM) GST-hDM2 | GST-hDMX | p53 Nuclear translocation of p53 (GRIP assay) | Affinity selection MS Kd (nM) GST-hDM2 | GST-hDMX | p21 activation ELISA 20µM | 10µM | 1uM | FP Competition Binding IC50 (nM) HDM2 | HDMX | CD %Helicity 0%TFE | 50%TFE |
|---|---|---|---|---|---|---|---|---|---|---|---|---|---|---|---|---|
| SP-1 | 2069.40 | Ac-LSQETFSr8DLWKLLSEN-NH2 | >50 | | | | | | | | | | | | | |
| SP-2 | 2067.43 | Ac-LSQETFSr8NLWKLLSQN-NH2 | >50 | | | | | | | | | | | | | |
| SP-3 | 2094.46 | Ac-LSQQTFSr8NLWRLLSQN-NH2 | 17.6; 10.3 | | 13.4 | | | | | | | | | | | |
| SP-4 | 2081.42 | Ac-QSQQTFSr8NLWRLLSQN-NH2 | 36.8; 21.2 | | | | | | | | | | | | | |
| SP-5 | 2109.4 | Ac-QSQQTFSr8NLWRLLSQN-NH2 | 22.6, 16.5, 18.4, 18.4, 17.1, 17.9 | 12.0 | 2.7; 5.4 | 67; 56 | 14.3 | 25 | 90 | 32; 16 | 1 | 0.9 | 74.8, 76.5 | 100 | | |
| SP-6 | 2033.33 | Ac-QSQQTASr8NLWRLLSQN-NH2 | >50 | >25 | >1000 | >1000 | >50 | | | | | | | | | |
| SP-7 | 2107.46 | Ac-QAibQQTFSr8NLWRLLSQN-NH2 | 19.9; 14.3; 10.3 | >25 | | | | | | | | | | | | |
| SP-8 | 2001.21 | Ac-QSQQTFSNLWRLLPQN-NH2 | >50 | | | | | | | | | | | | | |
| SP-9 | 2137.48 | Ac-QSQQTFSjr8NLWRLLSQN-NH2 | 7.3 | | >1000 | >1000 | >50 | | | | | | 5 | 34 | | |
| SP-10 | 2066.40 | Ac-QSQAibTFSjr8NLWRLLSQN-NH2 | 11.4 | | 26.6 | | | | | | | | 55 | 98 | | |
| SP-11 | 2052.38 | Ac-QSQQTFSr8NLWRLLSAN-NH2 | 13.0 | | 15.9, | | | | | | | | | | | |
| SP-12 | 2052.38 | Ac-ASQQTFSr8NLWRLLSQN-NH2 | 10.0 | | 17.4 | | | | | | | | | | | |
| SP-13 | 2066.40 | Ac-QSQQTFSr8ALWRLLSQN-NH2 | 13.7 | | | | | | | | | | | | | |
| SP-14 | 2110.41 | Ac-QSQQTFSr8NLWRLLSEN-NH2 | >50 | | | | | | | | | | | | | |
| SP-15 | 2137.49 | Ac-RSQQTFSr8NLWRLLSQN-NH2 | 5.6 | | 42.3, 13.5 | 199, | 13.45 | | | | | | 62.3 | 94.6 | | |
| SP-16 | 2138.47 | Ac-RSQQTFSr8NLWRLLSEN-NH2 | 10.3 | | | | | | | | | | | | | |
| SP-17 | 1961.17 | Ac-LSQETFSDLWKLLPEN-NH2 | >50 | | | | | | | | | | | | | |
| SP-18 | 2009.31 | Ac-QSQQTFSjLWRLLPQN-NH2 | >50 | | | | | | | | | | | | | |
| SP-19 | 2037.28 | Ac-QSQQSFSNSMRLLPQN-NH2 | >50 | | | | | | | | | | | | | |
| SP-20 | 1918.16 | Ac-QSQQTSSNLSRLLPQN-NH2 | >50 | | | | | | | | | | | | | |
| SP-21 | 2008.28 | Ac-QSQQTFSNLWSLLPQN-NH2 | >50 | | | | | | | | | | | | | |
| SP-22 | 2311.64 | Ac-RTQATFSr8NQWAibANi6TNAibTR-NH2 | 35.2 | | | | | | | | | | | | | |
| SP-23 | 2137.49 | Ac-QSQQTFSr8NLWRLLSRN-NH2 | >50 | | | | | | | | | | | | | |
| SP-24 | 2137.49 | Ac-QSQRTFSr8NLWRLLSQN-NH2 | >50 | | | | | | | | | | | | | |

FIG. 6B

| SP# | MW | Sequence | SJSA-1 Cell viability EC50 (μM) serum free | | Competition ELISA IC50 (nM) | | p53 Nuclear translocation of p53 (GRIP assay) | Affinity selection MS Kd (nM) | | p21 activation ELISA | | | FP Competition Binding IC50 (nM) | | CD %Helicity | |
|---|---|---|---|---|---|---|---|---|---|---|---|---|---|---|---|---|
| | | | 24h | 72h | GST-hDM2 | GST-hDMX | | GST-hDM2 | GST-hDMX | 20μM | 10μM | 1μM | HDM2 | HDMx | 0%TFE | 50%TFE |
| SP-25 | 2109.43 | Ac-QSQQTF$r8NNIeWRLLSQN-NH2 | | | | | | | | | | | | | | |
| SP-26 | 2109.43 | Ac-QSQQTF$r8NLWRNIeLSQN-NH2 | 14.8; 6.2; 11.8; 19.7 | | | | | | | | | | | | | |
| SP-27 | 2109.43 | Ac-QSQQTF$r8NLWRLNIeSQN-NH2 | 14.8 | | | | | | | | | | | | | |
| SP-28 | 2125.43 | Ac-QSQQTYS$r8NLWRLLSQN-NH2 | >50 | | | | | | | | | | | | | |
| SP-29 | 2135.51 | Ac-RAibQQTF$r8NLWRLLSQN-NH2 | 5; 4.9; 11.5; 19.5 | | | | | | | | | | | | | |
| SP-30 | 1599.83 | Ac-MPRFMDYWEGLN-NH2 | 8.6 | | 64 | | 26.8 | | | 62.6 | 1.1 | 0.9 | | | 7.5 | 58.2 |
| SP-31 | 2192.57 | Ac-RSQQRF$r8NLWRLLSQN-NH2 | 15.5,16.9 | | | | | | | | | | | | | |
| SP-32 | 2164.51 | Ac-QSQQRF$r8NLWRLLSQN-NH2 | 7.6 | | | | | | | | | | | | | |
| SP-33 | 2190.59 | Ac-RAibQQRF$r8NLWRLLSQN-NH2 | 5.2, 4.8 | | | | | | | | | | | | | |
| SP-34 | 2226.58 | Ac-RSQQRF$r8NPWRLLSQN-NH2 | | | | | | | | | | | | | | |
| SP-35 | 2247.58 | Ac-RSQQRF$r8NYWRLLSQN-NH2 | 5.3, 5.7, 11.4 | | | | | | | | | | | | | |
| SP-36 | 2109.43 | Ac-RSQQTF$r8NLWQLLSQN-NH2 | 41.9 | | | | | | | | | | | | | |
| SP-37 | 2095.40 | Ac-QSQQTF$r8NLWQAmILSQN-NH2 | 9.1 | | | | | | | | | | | | | |
| SP-38 | 2123.46 | Ac-QSQQTF$r8NAmWRLLSQN-NH2 | >50 | | | | | | | | | | | | | |
| SP-39 | 1871.14 | Ac-NlePRF$r8DYWEGLSQN-NH2 | 5.2; 5.9 | | | | 3.82 | | | 0.8 | 1.5 | 1.3 | | | 62.6 | 90.6 |
| SP-40 | 1953.33 | Ac-NlePRF$r8NYWRLLSQN-NH2 | >50 | | | | 6.3 | | | 3.1 | 1.7 | 1 | | | | |
| SP-41 | 1578.94 | Ac-RF$r8NLWRLLSQ-NH2 | 14.5 | | | | | | | | | | | | | |
| SP-42 | 2161.44 | Ac-QSQQTF$r8N2fWRLLSQN-NH2 | 18.3 | | | | | | | | | | | | | |
| SP-43 | 2161.44 | Ac-QSQQTF$r8N3fWRLLSQN-NH2 | 14 | | | | 29.3 | 25 | 180 | | | | | | 50.5 | 94.8 |
| SP-44 | 2081.38 | Ac-QSQQTF#r8NLWRLL#QN-NH2 | 32.85 | | | | | | | | | | | | | |
| SP-45 | 2061.39 | Ac-RSQQTA$r8NLWRLLSQN-NH2 | 6.8 | | 175 | | 10.1 | | | | | | | | 64.3, 85 | 88.5, 121 |
| SP-46 | 2111.45 | Ac-QSQQTF%r8NLWRLL%QN-NH2 | >50 | | | | | | | | | | | | | |
| SP-47 | 2052.33 | HepQSQSTFSNLWRLLPQN-NH2 | >50 | | | | | | | | | | | | | |
| SP-48 | 2160.56 | HepQSQSTFS$r8NLWRLLSQN-NH2 | | | | | | | | | | | | | | |

FIG. 6C

| SP# | MW | Sequence | SJSA-1 Cell viability EC50 (μM) serum free 24h | SJSA-1 Cell viability EC50 (μM) serum free 72h | Competition ELISA IC50 (nM) GST-hDM2 | Competition ELISA IC50 (nM) GST-hDMX | p53 Nuclear translocation of p53 (GRIP assay) | Affinity selection MS Kd (nM) GST-hDM2 | Affinity selection MS Kd (nM) GST-hDMX | p21 activation ELISA 20μM | p21 activation ELISA 10μM | p21 activation ELISA 1μM | FP Competition Binding IC50 (nM) HDM2 | FP Competition Binding IC50 (nM) HDMx | CD %Helicity 0%TFE | CD %Helicity 50%TFE |
|---|---|---|---|---|---|---|---|---|---|---|---|---|---|---|---|---|
| SP-49 | 2143.87 | Ac-QSQQTF$r8NL6c1WRLL$QN-NH2 | 15.94 | | | | 11.25 | | | | | | | | | |
| SP-50 | 2157.90 | Ac-QSQQTF$r8NLMe6c1WRLL$QN-NH2 | | | | | >50 | | | | | | | | | |
| SP-51 | 1536.68 | Ac-LITEHYWAQLTS-NH2 | >50 | | | | | | | | | | | | 60.9 | 82.4 |
| SP-52 | 1586.83 | Ac-LITF$HYW$QLTS-NH2 | >50 | | | | | | | | | | | | -0.5 | 61.6 |
| SP-53 | 1521.75 | Ac-LITFE$YWA$LTS-NH2 | >50 | | | | | | | | | | | | | |
| SP-54 | 1598.88 | Ac-LITF$r8HYWAQL$S-NH2 | 16.3 | | | | 19.3 | | | | | | | | 85.6 | 96.6 |
| SP-55 | 1683.99 | Ac-LITF$r8HYWRQL$S-NH2 | 12.8 | | | | >50 | | | | | | | | 59.5 | 84.2 |
| SP-56 | 2146.53 | Ac-QSQQTF$NLWRLL$s8QN-NH2 | >50 | | 383 | | | | | 25.2 | 15.1 | | | | 98.9, 109 | 110, 124 |
| SP-57 | 1925.11 | Ac-QSQQTA$NLWRLLPQN-NH2 | >50 | | | | | | | 1 | 1 | | | | | |
| SP-58 | 2061.39 | Ac-QSQQTA$r8NLWRLL$QN-NH2 | | | | | | | | | | | | | | |
| SP-59 | 2080.43 | Ac-ASQQTF$r8NLWRLL$QN-NH2 | | | | | | | | | | | | | | |
| SP-60 | 2010.30 | Ac-SSQQ$FSNLWRLLAibQN-NH2 | | | | | | | | | | | | | | |
| SP-61 | 2024.32 | Ac-QS$QQTF$NLWRLLAibQN-NH2 | 35.76 | | | | | | | | | | | | | |
| SP-62 | 2025.27 | Ac-QSQQ$FSN$WRLLAibQN-NH2 | >50 | | | | | | | | | | | | | |
| SP-63 | 1996.27 | Ac-QSQQTF$NLW$LLAibQN-NH2 | >50 | | | | | | | | | | | | | |
| SP-64 | 2012.27 | Ac-QSQQTF$$LWR$LAibQN-NH2 | >50 | | | | | | | | | | | | | |
| SP-65 | 1941.19 | Ac-QSQQTF$NLW$LLA$N-NH2 | >50 | | | | | | | | | | | | | |
| SP-66 | 2038.35 | Ac-$SQQ$FSNLW$LLAibQN-NH2 | 16.57 | | | | | | | | | | | | | |
| SP-67 | 2052.38 | Ac-QS$/QQTF$/NLWRLLAibQN-NH2 | 36.94 | | | | | | | | | | | | | |
| SP-68 | 2053.32 | Ac-QSQQ$/FSN$/WRLLAibQN-NH2 | >50 | | | | | | | | | | | | | |
| SP-69 | 2024.32 | Ac-QSQQTF$/NLW$/LLAibQN-NH2 | 36.06 | | | | | | | | | | | | | |
| SP-70 | 1997.30 | Ac-QSQQ$TF$/LWRLLAibQN-NH2 | 36.06 | | | | | | | | | | | | | |
| SP-71 | 2025.35 | Ac-QSQ$/TF$/LWRLLAibQN-NH2 | 30.36 | | | | | | | | | | | | | |
| SP-72 | 2202.64 | Ac-QS$/QTF$/NLWRLL$s8QN-NH2 | 5.1 | | >1000 | | 10.68 | | | | | | | | 99 | 108 |

FIG. 6D

| SP# | MW | Sequence | SJSA-1 Cell viability EC50 (μM) serum free | | Competition ELISA IC50 (nM) | | p53 Nuclear translocation of p53 (GRIP assay) | Affinity selection MS Kd (nM) | | p21 activation ELISA | | | | FP Competition Binding IC50 (nM) | | CD %Helicity | |
|---|---|---|---|---|---|---|---|---|---|---|---|---|---|---|---|---|---|
| | | | 24h | 72h | GST-hDM2 | GST-hDMX | | GST-hDM2 | GST-hDMX | 20μM | 10μM | 1μM | HDM2 | HDM2 | HDMx | 0%TFE | 50%TFE |
| SP-73 | 2039.38 | Ac-S$r8SQQTFS$LWRLLAibQN-NH2 | 14.01 and 26.91 | | | | | | | | | | | | | | |
| SP-74 | 1997.30 | Ac-QSQS$r8TFSNLW$LLAibQN-NH2 | >50 (both) | | | | | | | | | | | | | | |
| SP-75 | 2025.35 | Ac-QSQQTFS$r8LWRLLA$N-NH2 | >50 | | | | | | | | | | | | | | |
| SP-76 | 2033.37 | Ac-QS$r5QTFSNLW$SLLAibQN-NH2 | >50 | | | | | | | | | | | | | 0 | 58 |
| SP-77 | 2067.43 | Ac-S$r8SQQTFS$LWRLLAibQN-NH2 | | | | | | | | | | | | | | | | |
| SP-78 | 2025.35 | Ac-QSQS$r8TFSNLW$LLAibQN-NH2 | | | | | | | | | | | | | | | | |
| SP-79 | 2053.41 | Ac-QSQQTFS$r8LWRLLA$N-NH2 | | | | | | | | | | | | | | | | |
| SP-80 | 2089.48 | Ac-QS$r5QTFS$/NLW$LLAibQN-NH2 | | | | | | | | | | | | | | | | |
| SP-81 | 1989.19 | Ac-QSQQTF5NLWRLLAibQN-NH2 | | | | | | | | | | | | | | | | |
| SP-82 | 2216.67 | Hep(Q)SQS/TF$/r8NLWRLL$/QN-NH2 | | | | | | | | | | | | | | | | |
| SP-83 | 2052.38 | Ac-ASQQTF5$r8NLRW/LSQN-NH2 | | | | | | | | | | | | | | | | |
| SP-84 | 2023.38 | Ac-QSQQTF$/r8NLWRLL$/Q-NH2 | | | >50 | | | | | | | | | | | | | |
| SP-85 | 1995.33 | Ac-QSQQTFS$r8NLWRLLSQ-NH2 | 9.35 | | 20.7 | | | | | | | | | | | | | |
| SP-86 | 1516.79 | Ac-AAARAA$r8AAARA$AA-NH2 | | | | | | | | | | | | | | | | |
| SP-87 | 1607.76 | Ac-LTFEHYWAQLTSA-NH2 | | | | | | | | | | | | | | | | |
| SP-88 | 1669.96 | Ac-LTF5/r8HYWAQLS$A-NH2 | | | 6.5 | | | | 12.1 | | | | | | | | | |
| SP-89 | 1944.15 | Ac-ASQQTFSNLWRLLPQN-NH2 | | | | | | | | | | | | | | | | |
| SP-90 | 2033.37 | Ac-QS$r8QTFSNLW$r5LLAibQN-NH2 | | | | | | | | | | | | | | 77.8 | 95.7 | |
| SP-91 | 1987.22 | Ac-QSQQTFAibNLWRLLAibQN-NH2 | | | | | | | | | | | | | | 13.1 | 14.3 | |
| SP-92 | 2043.33 | Ac-QSQQTFNleNLWRLLNleQN-NH2 | | | | | | | | | | | | | | | | |
| SP-93 | 2083.39 | Ac-QSQQTF$/r8NLWRLLAibQN-NH2 | | | | | | | | | | | | | | 80.8 | 81.8 | |
| SP-94 | 2111.45 | Ac-QSQQTF$/r8NLWRLLNleQN-NH2 | | | | | | | | | | | | | | | | |
| SP-95 | 2041.31 | Ac-QSQQTFAibNLWRLLS$QN-NH2 | | | | | | | | | | | | | | | | |
| SP-96 | 2069.37 | Ac-QSQQTFNleNLWRLLS$QN-NH2 | | | | | | | | | | | | | | | | |

FIG. 6E

| SP# | MW | Sequence | SJSA-1 Cell viability EC50 (μM) serum free | | Competition ELISA IC50 (nM) | | p53 Nuclear translocation of p53 (GRIP assay) | Affinity selection MS Kd (nM) | | p21 activation ELISA | | | | FP Competition Binding IC50 (nM) | | | CD % Helicity | |
|---|---|---|---|---|---|---|---|---|---|---|---|---|---|---|---|---|---|---|
| | | | 24h | 72h | GST-hDM2 | GST-hDMX | | GST-hDM2 | GST-hDMX | 20μM | 10μM | 1μM | | HDM2 | HDMx | 0%TFE | 50%TFE |
| SP-97 | 2145.89 | Ac-QSQQTF$%r8NL6clWRNle_%QN-NH2 | | | | | | | | | | | | | | | | |
| SP-98 | 2159.92 | Ac-QSQQTF%r8NLMe6clwRLL%QN-NH2 | | | | | | | | | | | | | | | 62.4 | 71.1 |
| SP-101 | 1161.39 | Ac-FNle6SYWE$L-NH2 | | | | | | | | | | | | | | | | |
| SP-102 | 1345.63 | Ac-F$r8AYWELL$A-NH2 | | | | | | | | | | | | | | | | |
| SP-103 | 1344.64 | Ac-F$r8AYWQLL$A-NH2 | | | | | | | | | | | | | | | | |
| SP-104 | 1926.26 | Ac-NlePRF$r8NYWELL$QN-NH2 | | | | | | | | | | | | | | | | |
| SP-105 | 1954.32 | Ac-NlePRF$8DYWRLL$QN-NH2 | | | | | | | | | | | | | | | | |
| SP-106 | 1839.23 | Ac-NlePRF$r8NVWRLL$Q-NH2 | | | | | | | | | | | | | | | | |
| SP-107 | 1711.10 | Ac-NlePRF$r8NYWRLL$-NH2 | | | | | | | | | | | | | | | 54.4 | 80.5 |
| SP-108 | 2110.41 | Ac-QSQQTF$r8DLWRLL$QN-NH2 | | | | | | | | | | | | | | | | |
| SP-109 | 2110.41 | Ac-QSQQTF$r8NLWRLL$EN-NH2 | | | | | | | | | | | | | | | | |
| SP-110 | 2110.41 | Ac-QSQQTF$r8NLWRLL$QD-NH2 | | | | | | | | | | | | | | | | |
| SP-111 | 1954.27 | Ac-QSQQTF$r8NLWRLL$S-NH2 | | | | | | | | | | | | | | | | |
| SP-112 | 2110.41 | Ac-ESQQTF$r8NLWRLL$QN-NH2 | | | | | | | | | | | | | | | | |
| SP-113 | 1637.02 | Ac-LlTF$r8NLWRNleL$Q-NH2 | | | | | | | | | | | | | | | | |
| SP-114 | 1692.10 | Ac-LRPF$r8NLWRNle$Q-NH2 | | | | | | | | | | | | | | | | |
| SP-115 | 2182.48 | Ac-QSQQTF$r8NWWRNleL$QN-NH2 | | | | | | | | | | | | | | | | |
| SP-116 | 1995.33 | Ac-QSQQTF$r8NLWRNle$Q-NH2 | | | | | | | | | | | | | | | | |
| SP-117 | 1766.09 | Ac-QTF$r8NLWRNle$QN-NH2 | | | | | | | | | | | | | | | | |
| SP-118 | 1976.37 | Ac-NlePRF$r8NWWRLL$QN-NH2 | | | | | | | | | | | | | | | | |
| SP-119 | 1805.22 | Ac-NlePRF$r8NWWRLL$A-NH2 | | | | | | | | | | | | | | | | |
| SP-120 | 1468.61 | Ac-TSPAEYWNLL$P-NH2 | | | | | | | | | | | | | | | 6.8 | 30.6 |
| SP-121 | 1652.89 | Ac-QTF$r8HWWSQL$S-NH2 | | 4.1 | | | | | | | | | | | | | 21.6 | 88.2 |
| SP-122 | 1179.43 | Ac-FMSYWE$L-NH2 | | | | | | | | | | | | | | | | |
| SP-123 | 1602.75 | Ac-QTFEHWWSQLL$-NH2 | | | | | | | | | | | | | | | 21.6 | 87.6 |

FIG. 6F

| SP# | MW | Sequence | SJSA-1 Cell viability EC50 (µM) serum free | | Competition ELISA IC50 (nM) | | p53 Nuclear translocation of p53 (GRIP assay) | Affinity selection MS Kd (nM) | | p21 activation ELISA | | | FP Competition Binding IC50 (nM) | | CD % Helicity | |
|---|---|---|---|---|---|---|---|---|---|---|---|---|---|---|---|---|
| | | | 24h | 72h | GST-hDM2 | GST-hDMX | | GST-hDM2 | GST-hDMX | 20µM | 10µM | 1µM | HDM2 | HDMx | 0% TFE | 50% TFE |
| SP-124 | 2123.46 | Ac-QSQQTF$r8NLAmwRLNl$s8QN-NH2 | | | | | | | | | | | | | | |
| SP-125 | 1131.73 | Ac-FNAibY6clWEAc3cL-NH2 | | | | | | | | | | | | | -3.6 | 16.3 |
| SP-126 | 1195.84 | Ac-FNle$Y6clWE$L-NH2 | | | | | | | | | | | | | 4.6 and 2.3 | 58.1 |
| SP-127 | 1278.92 | Ac-F$r8AY6clWEAc3cL$-NH2 | | | | | | | | | | | | | | |
| SP-128 | 1350.00 | Ac-F$r8AY6clWEAc3cL$A-NH2 | | | | | | | | | | | | | | |
| SP-129 | 1987.78 | Ac-NlePRF$r8NY6clWRLLSQN-NH2 | | | | | | | | | | | | | | |
| SP-130 | 1224.49 | Ac-AF$r8AAWALA$A-NH2 | | | | | | | | | | | | | | |
| SP-131 | 1396.68 | Ac-TF$r8AAWRLA$Q-NH2 | | | | | | | | | | | | | | |
| SP-132 | 1410.70 | Pr-TF$r8AAWRLA$Q-NH2 | | | | | | | | | | | | | | |
| SP-133 | 2111.45 | Ac-QSQQTF%r8NLWRNleL%QN-NH2 | | | | | | | | | | | | | 84.7 | 110.8 |
| SP-134 | 1671.98 | Ac-LTF%r8HYWAQL%S8-NH2 | | | | | | | | | | | | | 78.4 | 82 |
| SP-135 | 1955.35 | Ac-NlePRF%r8NYWRLL%QN-NH2 | | | | | | | | | | | | | 61.6 | 84.8 |
| SP-136 | 1989.80 | Ac-NlePRF%r8NY6clWRLL%QN-NH2 | 2.6 | | | | | | | | | | | | | |
| SP-137 | 1635.34 | Ac-LTF%r8HY6clWAQL%S-NH2 | 2 | | | | | | | | | | | | 69.5 | 78.6 |
| SP-138 | 2150.56 | Ac-QS%QTF%SlNLWRLL%s8QN-NH2 | | | | | | | | | | | | | 96 | 101.3 |
| SP-139 | 1720.45 | Ac-LTF%r8HY6clWRQL%S-NH2 | | | | | | | | | | | | | 74.2 | 94.2 |
| SP-140 | 2145.89 | Ac-QSQQTF%r8NL6clWRLL%QN-NH2 | | | | | | | | | | | | | 92.4 | 120.8 |
| SP-141 | 2041.40 | Ac-%r8SQQTF$%LWRLLAibQN-NH2 | 0.65 | | | | | | | | | | | | 66.7 | 105.6 |
| SP-142 | 1600.90 | Ac-LTF%r8HYWAQL%S-NH2 | | | | | | | | | | | | | 45.2 | 44.7 |
| SP-143 | 1603.90 | Ac-TSF%r8QYWNLL%P-NH2 | | | | | | | | | | | | | 2.6 | 26.5 |

FIG. 7A

| SP# | SEQUENCE | | | | | | | | | | | | | | FP Competition Binding Assay | | | | SJSA-1 Cell Viability 72h (10% FBS) | | p21 levels at 21h (10% FBS) (pg/ml) | | | |
|---|---|---|---|---|---|---|---|---|---|---|---|---|---|---|---|---|---|---|---|---|---|---|---|---|
| | | | | | | | | | | | | | | | HDM2 IC50 (nM) | HDMx IC50 (nM) | HDM2 Ki (IC50) - FAM-pDi | HDMx Ki (IC50) - FAM-pDi | AVE EC50 (uM) | SD | 30uM | 10uM | 3uM | 1uM |
| Nutlin 3a | | | | | | | | | | | | | | | 442 | 42500 | 82.3 | 6876 | 1.6 | 0.55 | 3290±619 | 2659±749 | 915±262 | BDL |
| SP-5 | Ac- | Q | | T | F | $r8 | N | L | W | R | L | $s | Q | N-NH2 | 94.1 | 667 | 14 | 91 | >30 | | ND | ND | ND | ND |
| SP-128 | | | Ac- | | F | $r8 | A | 6clW | E | Ac3c | L | $s | A | -NH2 | 114.5 | 967 | 2.5 | 85.1 | 4.5 | 1.70 | 2400±584 | 1535±166 | 522±82 | BDL |
| SP-142 | Ac- | L | T | F | $r8 | H | Y | W | A | Q | L | $s | S | -NH2 | 88.13 | 408 | 4.5 | 63.9 | 14.2 | 5.40 | 2598 | 170 | BDL | BDL |
| SP-191 | Ac- | L | T | F | $r8 | A | Y | W | A | Q | L | $s | S | -NH2 | 74.92 | 97 | 8.4 | ND | 5.7 | 0.80 | 1672±267 | 1068±93 | 105±79 | BDL |
| SP-194 | Ac- | L | T | F | $r8 | H | Y | W | A | Q | L | $s | A | A | 140.55 | 463 | 9.1 | nD | 5.2 | 1.00 | 1723±494 | 937±117 | 178±88 | BDL |
| SP-344 | Ac- | L | T | F | $r8 | A | Y | W | A | Q | L | $s | A | -NH2 | 59.41 | 348 | 5.2 | nD | 7.4 | 1.20 | 1688±443 | 1009±668 | BDL | BDL |
| SP-266 | Ac- | L | T | F | $r8 | A | Y | W | S | Q | L | $s | A | -NH2 | 66 | 301 | 7 | 80 | 4.9 | 0.50 | 3751±942 | 1620±552 | 102±45 | BDL |
| SP-267 | Ac- | L | T | F | $r8 | V | Y | W | A | Q | L | $s | S | -NH2 | 190.5 | 318.5 | 21 | 85 | 5.3 | 1.27 | 3983±957 | 1106±519- | 43±19 | BDL |
| SP-360 | Ac- | L | T | F | $r8 | F | Y | W | A | Q | F | $s | S | -NH2 | 90 | 110 | <1 | 27 | 5.0 | 2.36 | 3337±836 | 1182±509 | 265±38 | BDL |
| SP-512 | Ac- | E | T | F | $r8 | E | Y | W | S | A | L | $s | A | -NH2 | 16.2 | 26.1 | 1.86 | 4.76 | 11.3 | 3.59 | 3137±630 | 879±289 | BDL | BDL |
| SP-508 | Ac- | L | T | F | $r8 | A | Y | 6clW | E | A | L | $s | A | -NH2 | 22.76 | 88.82 | 2.18 | 15.12 | 7.1 | 3.00 | 2322±572 | 972±182 | 451±103 | BDL |
| SP-522 | mdP EG3- | L | T | F | $r8 | A | Y | W | A | Q | L | $s | A | -NH2 | ND | ND | ND | ND | 1.88 | 0.82 | 1117±267 | 1038±184 | 1023±205 | BDL |
| SP-580 | | | | F | $r8 | A | Y | W | E | A | L | $s | S | -NH2 | 81 | 195 | 10 | 24 | 8.6 | 2.8 | 505±70 | (592, 169) | BDL | BDL |
| SP-523 | | | Ac- | F | $r8 | A | Y | dl6br W | E | A | L | $s | A | -NH2 | ND | ND | ND | ND | 6.14 | 2.47 | 1016±280 | 407±25 | 41±26 | BDL |
| SP-573 | | | Ac- | F | $r8 | A | Y | 6clW | E | A | L | $s | S | -NH2 | ND | ND | ND | ND | 1.44 | 0.74 | 1103±319 | 1118±298 | 709±217 | BDL |
| SP-256 | Ac- | W | T | F | $r8 | H | Y | W | A | Q | L | $s | A | -NH2 | 185 | 204 | 201 | 54 | 6.7 | 3.3 | 3625±856 | 330±112 | BDL | BDL |
| SP-351 | | | Ac- | | F | $r8 | A | Y | W | A | Q | L | $s | S | -NH2 | 47.2 | 143 | <10 | 24.1 | 0.7 | 0.44 | 1784 | 1860 | 1184±756 | 132 |
| SP-641 | | | Ac- | F | $r8 | A | Y | 6clW | Q | A | L | $s | A | -NH2 | ND | ND | ND | ND | 2.7 | 0.23 | 1755 | 958 | 497 | 75 |

FIG. 7B

| SP# | SEQUENCE | | | | | | | | | | | | | | | | | Fold Caspase Activation relative to DMSO in 10% FBS @ 48h | | | | Cell Viability (10% FBS) EC50 (uM) | | | | | % Helicity @ 222 nM vs parent seq | |
|---|---|---|---|---|---|---|---|---|---|---|---|---|---|---|---|---|---|---|---|---|---|---|---|---|---|---|---|---|
| | | | | | | | | | | | | | | | | | | 30uM | 10uM | 3uM | 1uM | RKO (72h) | HCT-116, 5k/well (72h) | MCF-7 (7500 cells/well, 5day) | SW-480, 2k/well, 6d | RKO-E6 (72h) | 0% TFE | 50% TFE |
| Nutlin 3a | Ac | Q | S | Q | | | Q | T | F | Sr8 | N | L | W | R | L | L | S | Q | N-NH2 | 45.5 | 26.5 | 13.3 | 1.0 | 6.7±2.5 | 8.9±4.9 | 5±1.9 | >30 | >30 | 74% | 100% |
| SP-5 | | | | | Ac- | | | F | Sr8 | A | Y | 6clW | E | AC3c | L | S | A | -NH2 | ND | ND | ND | ND | ND | ND | ND | ND | ND | 10% | 188% |
| SP-128 | | | | | | | | T | F | Sr8 | H | Y | W | A | Q | L | S | S-NH2 | 29.6 | 9.1 | 2.0 | 1.0 | 20.8±10.5 | >30 | 10.7±0.4 | >30 | >30 | 94% | 94% |
| SP-142 | | | | | Ac- | | | T | F | Sr8 | A | Y | W | A | Q | L | S | S-NH2 | 30.0 | 2.0 | 1.7 | 1.0 | 12.6±1.6 | 24.1±4.3 | ND | 26.7 | >30 | 4% | 151% |
| SP-191 | | | | | Ac- | | L | T | F | Sr8 | H | Y | W | A | Q | L | S | S-NH2 | 34.5 | 5.1 | 1.8 | 1.0 | 10.6±3.8 | 11.1±2.4 | 6.4±1.2 | >30 | >30 | 5% | 143% |
| SP-194 | | | | | Ac- | | L | T | F | Sr8 | A | Y | W | A | Q | L | S | A-NH2 | 32.6 | 5.8 | 2.2 | 1.0 | ND | 11.2±6.5 | 4±0.4 | >30 | >30 | 140% | 140% |
| SP-344 | | | | | Ac- | | L | T | F | Sr8 | H | Y | W | S | Q | L | S | A | 38.8 | 5.3 | 1.6 | 1.0 | 15.3±5.1 | 11.3±3.7 | 10.2±1.6 | >30 | >30 | 2% | 142% |
| SP-266 | | | | | Ac- | | L | T | F | Sr8 | V | Y | W | A | Q | L | S | S-NH2 | 30±0 | 12±11 | 1±0 | 1.0 | 16±2 | 7.5±0.85 | ND | 19.2±2.7 | >30 | 1% | 120% |
| SP-267 | | | | | Ac- | | L | T | F | Sr8 | F | Y | W | A | Q | L | S | A-NH2 | 29±4 | 15±8 | 2±1 | 1.0 | 9.5±2.5 | 5.5±0.5 | ND | 17.5±7.8 | ~29uM | 8% | 119% |
| SP-360 | | | | | Ac- | | L | T | F | Sr8 | A | Y | W | A | Q | L | S | S-NH2 | 30±4 | 11±8 | 3±0 | 1.0 | 5.5±0.7 | 6.6 | ND | >30 | >30 | 2% | 131% |
| SP-512 | | | | | Ac- | | L | T | F | Sr8 | E | Y | W | A | Q | L | S | S-NH2 | 24±6 | 11±2 | 4±2 | 1.0 | >30 | ND | ND | >30 | >30 | 8% | 126% |
| SP-508 | | | | | Ac- | | L | T | F | Sr8 | A | Y | W | A | Q | F | S | S-NH2 | 19±6 | 8±4 | 5±1 | 1.0 | >30 | 27.1±5.1 | ND | >30 | >30 | 5% | 127% |
| SP-522 | | | | | Ac- | | E | T | F | Sr8 | A | Y | 6clW | E | A | L | S | A-NH2 | 27±1.7 | 17±2.2 | 11±0.5 | 1.0 | 11.7±1 | 13±5.8 | ND | >30 | >30 | 5% | 134% |
| SP-580 | | | | | mdPEG3- | | L | T | F | Sr8 | A | Y | W | A | Q | L | S | A-NH2 | 16±2.4 | 8±0.1 | 1±0.1 | 1.0 | >30 | 26.3±1.7 | ND | >30 | >30 | ND | ND |
| SP-523 | | | | | Ac- | | | T | F | Sr8 | A | Y | dl6brW | E | A | L | A | A-NH2 | 19±1 | 4±0.5 | 16±0.1 | 1.0 | 25±8.6 | >30 | ND | >30 | >30 | ND | ND |
| SP-573 | | | | | Ac- | | | T | F | Sr8 | A | Y | 6clW | E | A | L | S | A-NH2 | 23±1.2 | 16±1.8 | 6±2 | 1.0 | 2.25uM±7.7 | 16.8uM±6.2 | ND | 26.4uM±4.8 | >30 | ND | ND |
| SP-256 | | | | | | | W | T | F | Sr8 | H | Y | W | A | A | L | S | S-NH2 | 36±2 | 4±5 | 1±0 | 2 | 1.73 | 1.11 | ND | 4.46 | 9.07 | ND | ND |
| SP-351 | | | | | Ac- | | L | T | F | Sr8 | A | Y | W | A | A | L | S | A-NH2 | 31 | 29 | 15±5.5 | 1 | 25.49 | 28.25±2.52 | ND | >30 | >30 | ND | ND |
| SP-641 | | | | | Ac- | | | T | F | Sr8 | A | Y | 6clW | Q | A | L | S | A-NH2 | 20 | 13 | 6±1.8 | | | | | | | | |

FIG. 7C

| SP# | SEQUENCE | | | | | | | | | | | | | | FP Competition Binding Assay | | | | SJSA-1 Cell Viability 72h (10% FBS) | | p21 levels at 21h (10% FBS) (pg/ml) | | | |
|---|---|---|---|---|---|---|---|---|---|---|---|---|---|---|---|---|---|---|---|---|---|---|---|---|
| | | | | | | | | | | | | | | | HDM2 IC50 (nM) | HDMX IC50 (nM) | HDM2 Ki FAM-pDi (IC50) | HDMX Ki FAM-pDi (IC50) | AVE EC50 (uM) | SD | 30uM | 10uM | 3uM | 1uM |
| SP-684 | Ac- | I | T | F | S$8 | F | Y | W | A | Q | L | S | S | S-NH2 | 103.6 | 442 | <10 | 74.6 | 2.7 | 0.00 | 1687 | 563 | 51 | 25 |
| SP-681 | Ac- | L | T | F | S$8 | A | Y | W | V | Q | L | S | S | S-NH2 | 118 | 395 | <10 | 66.8 | 2.8 | 0.14 | 1983 | 368±290 | 57 | 76 |
| SP-686 | Ac- | F | T | F | S$8 | F | Y | W | A | Q | L | S | S | S-NH2 | 102.5 | 269 | <10 | 45.4 | 3.6 | 0.63 | 1798 | 196 | 0 | BDL |
| SP-688 | Ac- | L | T | F | S$8 | A | Y | W | A | Q | L | S | S | S-NH2 | 77.1 | 293.2 | <10 | 49.5 | 3.6 | 2.26 | 1282 | 398 | 6 | BDL |
| SP-671 | Ac- | L | T | F | S$8 | A | H | W | A | Q | L | S | A | A-NH2 | 63.6 | 110 | <10 | 18.6 | 3.7 | 0.69 | 1398 | 372 | 86 | 11 |
| SP-485 | Ac- | L | T | F | S$8 | E | Y | W | A | Q | L | S | A | A-NH2 | ND | ND | ND | ND | 3.9 | 0.50 | 1604 | 1125 | 208 | 88 |
| SP-604 | Ac- | L | T | F | S$8 | A | Y | W | A | Q | L | S | A | A-NH2 | 115 | 309.5 | <10 | 52.3 | 3.9 | 0.97 | 2183 | 254 | -6 | BDLE |
| SP-685 | Ac- | L | T | F | S$8 | F | Y | W | A | Q | L | S | A | A-NH2 | 97.9 | 491 | <10 | 83 | 4.0 | 2.68 | 1442 | 225 | 12 | 18 |
| SP-698 | Ac- | L | T | F | S$8 | L | Y | W | A | Q | L | S | a | -NH2 | 82.2 | 156.7 | <10 | 26.5 | 4.4 | 0.90 | 1574 | 530 | 88 | 42 |
| SP-586 | Ac- | L | T | F | S$8 | A | Y | W | S | Q | L | S | S | S-NH2 | 111 | 673 | 11 | 113.7 | 4.7 | 1.53 | 2259 | 516 | 0 | BDL |
| SP-585 | Ac- | L | T | F | S$8 | A | Y | W | S | Q | F | S | S | S-NH2 | 92 | 282 | <10 | 47.7 | 5.0 | 1.63 | 2112 | 739±305 | 32 | 51 |
| SP-623 | Ac- | L | T | F | S$8 | A | Y | W | A | Q | Cba | S | S | S-NH2 | 68.3 | 251 | <10 | 42.4 | 5.1 | 1.23 | 2343 | 1701±667 | 41 | 0 |
| SP-673 | Ac- | L | T | F | S$8 | A | Y | W | A | A | L | S | A | A-NH2 | 136.6 | 717 | 11 | 121 | 6.5 | 0.59 | 1693 | 606 | 80 | 0 |
| SP-714 | Ac- | | | F | S$8 | A | Y | 6clW | S | A | L | S | A | A-NH2 | ND | ND | ND | ND | 5.5 | 1.44 | 2064±24 | 1284±155 | 249±46 | 15±21 |
| SP-352 | Ac- | V | V | F | S$8 | A | Y | W | A | Q | L | S | S | S-NH2 | 80.9 | 386 | <10 | 65.3 | 5.8 | 2.58 | 1535±143 | 1028±439 | 55±37 | 0±0 |
| SP-709 | Ac- | E | E | F | S$8 | V | Y | W | A | Q | L | S | A | A-NH2 | 103 | 235 | <10 | 39.7 | 5.8 | 3.05 | 1574±47 | 787±149 | 278±27 | 56±37 |
| SP-643 | Ac- | L | T | F4F | S$8 | A | Y | W | A | Q | L | S | S | S-NH2 | ND | ND | ND | ND | 6.0 | 0.20 | 2137±287 | 1343±303 | 51±44 | 6±8 |
| SP-566 | Ac- | L | T | F | S$8 | A | Y | W | A | Q | L | S | S | S-NH2 | ND | ND | ND | ND | 6.1 | 1.35 | 2243±84 | 1111±29 | 24±3 | 4±6 |
| SP-696 | Ac- | W | T | F | S$8 | L | Y | W | S | Q | L | S | S | S-NH2 | 105 | 379 | <10 | 64 | 6.2 | 0.45 | 2177±162 | 247±365 | 0±0 | 0±0 |

FIG. 7D

| SP# | SEQUENCE | | | | | | | | | | | Fold Caspase Activation relative to DMSO in 10% FBS @ 48h | | | | Cell Viability (10% FBS) EC50 (uM) | | | | % Helicity @ 222 nM vs parent seq | |
|---|---|---|---|---|---|---|---|---|---|---|---|---|---|---|---|---|---|---|---|---|---|
| | | | | | | | | | | | | 30uM | 10uM | 3uM | 1uM | RKO (72h) | HCT-116, 5k/well, (72h) | MCF-7 (7500 cells/well, 5day) | SW-480, 2k/well, 6d | RKO-E6 (72h) | 0% TFE | 50% TFE |
| SP-684 | Ac- | I | T | F | Sr8 | F | Y | W | A | Q | L | S | S | -NH2 | 24 | 9 ± 6.0 | 1 | 1 | 11.26 | 9.37 | ND | 12.14 ± 4.56 | 27.63 | ND | ND |
| SP-681 | Ac- | L | T | F | Sr8 | A | Y | W | V | Q | L | S | S | -NH2 | 23 | 5 | 1 | 1 | 12.89 | 10.83 ± 5.46 | ND | 9.40 ± 3.10 | 24.07 ± 8.49 | ND | ND |
| SP-686 | Ac- | L | T | F | Sr8 | F | Y | W | A | Q | L | S | S | -NH2 | 24 | 2 | 1 | 1 | 11.2 | 2.1 | ND | 11.84 ± 5.19 | >30 | ND | ND |
| SP-688 | Ac- | F | T | F | Sr8 | A | H | W | A | Q | L | S | S | -NH2 | 17 | 6 | 1 | 1 | 23.86 ± 9.66 | 14.55 | ND | >30 | 28.12 | ND | ND |
| SP-671 | Ac- | L | T | F | Sr8 | E | Y | W | A | Q | L | S | S | -NH2 | 19 | 4 | 1 | 1 | >30 | 15.59 | ND | >30 | >30 | ND | ND |
| SP-485 | Ac- | L | T | F | Sr8 | A | Y | W | A | Q | L | S | A | -NH2 | 22 | 19 | 3 | 1 | 5.84 | 4.78 | ND | 13.83 | 29.88 | ND | ND |
| SP-604 | Ac- | L | T | F | Sr8 | F | Y | W | A | Q | L | S | A | -NH2 | 28 | 2 | 1 | 1 | 5.3 ± 4.1 | 5.6 ± 2.6 | ND | 9.3 ± 4 | 14.4 ± 8.1 | ND | ND |
| SP-685 | Ac- | L | T | F | Sr8 | F | Y | W | S | Q | L | S | S | -NH2 | 17 | 2 | 1 | 1 | 30.24 ± 4.25 | 7.32 ± 4.75 | ND | 15.82 | >30 | ND | ND |
| SP-698 | Ac- | L | T | F | Sr8 | A | Y | W | S | Q | Fa | a | S | -NH2 | 21 | 8 | 1 | 1 | 12.08 ± 4.57 | 4.05 | ND | 5.79 | >30 | ND | ND |
| SP-586 | Ac- | L | T | F | Sr8 | A | Y | W | A | Q | L | S | S | -NH2 | 20 | 5 | 1 | 1 | 25.03 ± 4.46 | 11.05 | ND | 17.68 | >30 | ND | ND |
| SP-585 | Ac- | L | T | F | Sr8 | A | Y | W | A | Q | L | S | S | -NH2 | 22 | 7 | 1 | 1 | 9.79 ± 4.47 | 9.55 | ND | 10.51 | 24.2 | ND | ND |
| SP-623 | Ac- | L | T | F | Sr8 | V | Y | W | A | Q | L | S | A | -NH2 | 21 | 15 | 1 | 1 | 7.37 | 7.5 | ND | 16.84 ± 5.95 | 27.98 | ND | ND |
| SP-673 | Ac- | L | T | F | Sr8 | A | Y | W | A | A | L | S | S | -NH2 | 25 | 9 ± 5.3 | 1 | 1 | 8.03 | 6.93 | ND | 13.7 ± 0.9 | >30 | ND | ND |
| SP-714 | | Ac- | F | Sr8 | F | Y | 6clW | S | A | L | S | A | -NH2 | 33 ± 1.3 | 16 ± 1.9 | 2 ± 0.3 | 1 ± 0 | 4.4 ± 1.7 | 7.6 ± 3.6 | ND | 4.6 ± 1.6 | 10.4 ± 1.8 | ND | ND |
| SP-352 | Ac- | V | F | Sr8 | A | Y | W | A | Q | L | S | S | -NH2 | | 13 ± 1.2 | 11 ± 1.6 | 1 ± 0.2 | 1 ± 0 | 5.6 ± 0.3 | 5 ± 0.3 | ND | >30 | >30 | ND | ND |
| SP-709 | Ac- | L | T | F | Sr8 | A | Y | W | A | Q | L | S | S | -NH2 | 25 ± 0.1 | 11 ± 2.3 | 2 ± 0.4 | 1 ± 0.1 | 29.2 ± 3.3 | >30 | ND | 7.1 ± 0.3 | 10.4 ± 1.8 | ND | ND |
| SP-643 | Ac- | E | F | Sr8 | A | Y | W | A | Q | L | S | S | -NH2 | 29 ± 2.2 | 16 ± 7.2 | 1 ± 0.1 | 1 ± 0.1 | 8.6 ± 1.8 | 7.1 ± 0.3 | ND | 17.1 ± 8.5 | >30 | ND | ND |
| SP-566 | Ac- | L | F4F | Sr8 | L | Y | W | S | A | L | S | S | -NH2 | 28 ± 2.6 | 17 ± 2.9 | 1 ± 0.1 | 1 ± 0.1 | 5.6 ± 3.6 | 9.1 ± 0 | ND | 9.8 ± 3.2 | 27.3 ± 3.1 | ND | ND |
| SP-696 | Ac-W | T | F | Sr8 | L | Y | W | S | Q | L | S | S | -NH2 | 26 ± 0.2 | 4 ± 4.8 | 1 ± 0 | 1 ± 0 | 9.1 ± 4.5 | 11.8 ± 4.9 | ND | 10 ± 4.3 | 29.8 ± 0.2 | ND | ND |

SP-142 in the SJSA-1 Xenograft Model in Nude Mice: Tumor Volume

| Group No. | Treatment | Amount/dose (mg/kg) | Schedule | ROA | TGI (%) after 13 days dosing |
|---|---|---|---|---|---|
| 1 | Vehicle control | - | qd | ip | - |
| 2 | Small molecule inhibitor control | 50 | qd | po | > 100% |
| 3 | SP-142 | 5 | qd | ip | 27% |
| 4 | SP-142 | 10 | qd | ip | 4.5% |
| 5 | SP-142 | 20 | qd | ip | 34% |

SP-190 & SP-343 in the SJSA-1 Xenograft Model in Nude Mice: Tumor Volume

| Group No. | Treatment | Amount/dose (mg/kg) | Schedule | ROA | TGI (%) after 13 days dosing |
|---|---|---|---|---|---|
| 1 | Vehicle control | - | qd | ip | - |
| 2 | Small molecule inhibitor control | 25 | qd | po | 97% |
| 3 | SP-190 | 40 | qd | ip | 58% |
| 4 | SP-343 | 40 | qd | ip | 30% |

PEPTIDOMIMETIC MACROCYCLES

CROSS-REFERENCE TO RELATED APPLICATIONS

This application is a continuation of U.S. application Ser. No. 16/126,300, filed Sep. 10, 2018, which is a continuation of U.S. application Ser. No. 14/460,848, filed Aug. 15, 2014, which is a divisional of U.S. application Ser. No. 13/816,880, filed Feb. 13, 2013 (or Apr. 25, 2013, which is the 371 date), now U.S. Pat. No. 8,859,723, which is a national stage entry of PCT/US2011/047692, filed Aug. 13, 2011, which claims the priority benefit of U.S. Provisional Application Nos. 61/373,701 filed Aug. 13, 2010, 61/373,638 filed Aug. 13, 2010, and 61/374,163 filed Aug. 16, 2010, each of which are incorporated by reference in their entirety.

The instant application contains a Sequence Listing, which has been submitted in ASCII format via EFS-Web and is hereby incorporated by reference in its entirety. Said ASCII copy, created on Sep. 6, 2019, is named 35224757303_SL.txt and is 586,442 bytes in size.

BACKGROUND OF THE INVENTION

The human transcription factor protein p53 induces cell cycle arrest and apoptosis in response to DNA damage and cellular stress, and thereby plays a critical role in protecting cells from malignant transformation. The E3 ubiquitin ligase HDM2 negatively regulates p53 function through a direct binding interaction that neutralizes the p53 transactivation activity, leads to export from the nucleus of p53 protein, and targets p53 for degradation via the ubiquitylation-proteasomal pathway. Loss of p53 activity, either by deletion, mutation, or HDM2 overexpression, is the most common defect in human cancers. Tumors that express wild type p53 are vulnerable to pharmacologic agents that stabilize or increase the concentration of active p53. In this context, inhibition of the activities of HDM2 has emerged as a validated approach to restore p53 activity and resensitize cancer cells to apoptosis in vitro and in vivo. HDMX (HDM4) has more recently been identified as a similar negative regulator of p53, and studies have revealed significant structural homology between the p53 binding interfaces of HDM2 and HDMX.

The p53-HDM2 and p53-HDMX protein-protein interactions are mediated by the same 15-residue alpha-helical transactivation domain of p53, which inserts into hydrophobic clefts on the surface of HDM2 and HDMX. Three residues within this domain of p53 (F19, W23, and L26) are essential for binding to HDM2 and HDMX. The present invention provides p53-based peptidomimetic macrocycles that modulate the activities of p53 by inhibiting the interactions between p53 and HDM2, p53 and HDMX, or p53 and both HDM2 and HDMX proteins, and that may be used for treating diseases including but not limited to cancer and other hyperproliferative diseases.

SUMMARY OF THE INVENTION

Described below are stably cross-linked peptides related to a portion of human p53 ("p53 peptidomimetic macrocycles"). These cross-linked peptides contain at least two modified amino acids that together form an intramolecular cross-link that can help to stabilize the alpha-helical secondary structure of a portion of p53 that is thought to be important for binding of p53 to HDM2 and for binding of p53 to HDMX. Accordingly, a cross-linked polypeptide described herein can have improved biological activity relative to a corresponding polypeptide that is not cross-linked. The p53 peptidomimetic macrocycles are thought to interfere with binding of p53 to HDM2 and/or of p53 to HDMX, thereby liberating functional p53 and inhibiting its destruction. The p53 peptidomimetic macrocycles described herein can be used therapeutically, for example to treat cancers and other disorders characterized by an undesirably low level or a low activity of p53, and/or to treat cancers and other disorders characterized by an undesirably high level of activity of HDM2 or HDMX. The p53 peptidomimetic macrocycles may also be useful for treatment of any disorder associated with disrupted regulation of the p53 transcriptional pathway, leading to conditions of excess cell survival and proliferation such as cancer and autoimmunity, in addition to conditions of inappropriate cell cycle arrest and apoptosis such as neurodegeneration and immunedeficiencies. In some instances, the p53 peptidomimetic macrocycles bind to HDM2 (e.g., GenBank® Accession No.: 228952; GI:228952) and/or HDMX (also referred to as HDM4; GenBank® Accession No.: 88702791; GI:88702791).

In one aspect, the present invention provides a peptidomimetic macrocycle comprising an amino acid sequence which is at least about 60%, 80%, 90%, or 95% identical to an amino acid sequence chosen from the group consisting of the amino acid sequences in Table 1, 2, 3, or 4. Alternatively, an amino acid sequence of said peptidomimetic macrocycle is chosen from the group consisting of the amino acid sequences in Table 1. Alternatively, an amino acid sequence of said peptidomimetic macrocycle is chosen as above, and further wherein the macrocycle does not include a thioether or a triazole. In some embodiments, the peptidomimetic macrocycle comprises a helix, such as an α-helix. In other embodiments, the peptidomimetic macrocycle comprises an α,α-disubstituted amino acid. A peptidomimetic macrocycle of the invention may comprise a crosslinker linking the α-positions of at least two amino acids. At least one of said two amino acids may be an α,α-disubstituted amino acid.

In some embodiments, the peptidomimetic macrocycle has the formula:

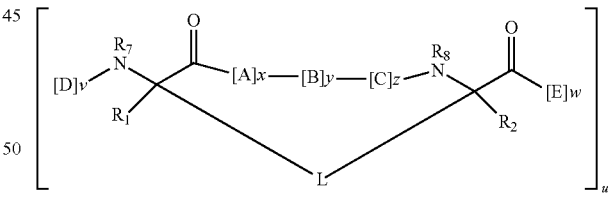

Formula I wherein:

each A, C, D, and E is independently a natural or non-natural amino acid, and the terminal D and E independently optionally include a capping group;

B is a natural or non-natural amino acid, amino acid analog,

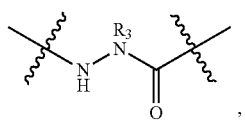

[—NH-L$_3$-CO—], [—NH-L$_3$-SO$_2$—], or [—NH-L$_3$-];

R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-;

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;

L is a macrocycle-forming linker of the formula -L$_1$-L$_2$-;

L$_1$ and L$_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;

R$_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;

v and w are independently integers from 1-1000;

u is an integer from 1-10;

x, y and z are independently integers from 0-10; and n is an integer from 1-5.

In various embodiments, the peptidomimetic macrocycle includes L$_1$ and L$_2$ wherein L$_1$ and L$_2$ either alone or in combination do not include a thioether or a triazole.

In other embodiments, the peptidomimetic macrocycle may comprise a crosslinker linking a backbone amino group of a first amino acid to a second amino acid within the peptidomimetic macrocycle. For example, the invention provides peptidomimetic macrocycles of the formula (IV) or (IVa):

Formula (IV)

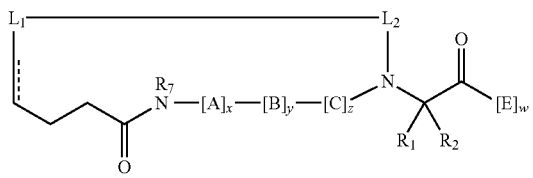

Formula (IVa)

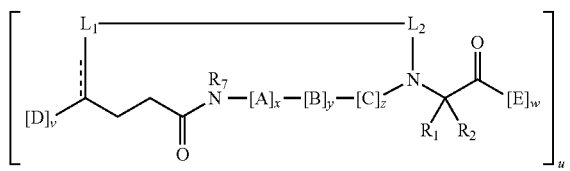

wherein:

each A, C, D, and E is independently a natural or non-natural amino acid, and the terminal D and E independently optionally include a capping group;

B is a natural or non-natural amino acid, amino acid analog,

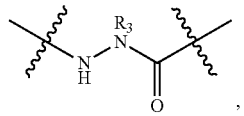

[—NH-L$_3$-CO—], [—NH-L$_3$-SO$_2$—], or [—NH-L$_3$-];

R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;

L$_1$ and L$_2$ are independently alkylene, alkenylene, alkynylene, heteroalkylene, cycloalkylene, heterocycloalkylene, cycloarylene, heterocycloarylene, or [—R$_4$—K—R$_4$—]n, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;

v and w are independently integers from 1-1000;

u is an integer from 1-10;

x, y and z are independently integers from 0-10; and n is an integer from 1-5.

Additionally, the invention provides a method of treating cancer in a subject comprising administering to the subject a peptidomimetic macrocycle of the invention. Also provided is a method of modulating the activity of p53 or HDM2 or HDMX in a subject comprising administering to the subject a peptidomimetic macrocycle of the invention, or a method of antagonizing the interaction between p53 and HDM2 and/or HDMX proteins in a subject comprising administering to the subject such a peptidomimetic macrocycle.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6a-f describe the results of a cell viability assay, a competition ELISA assay, GRIP assay, Kd data, p21 activation assay, fluorescence polarization competition binding and circular helicity data for exemplary peptidomimetic macrocycles of the invention.

FIGS. 7A-D provide data from a variety of macrocycles.

DETAILED DESCRIPTION OF THE INVENTION

Figure 1:
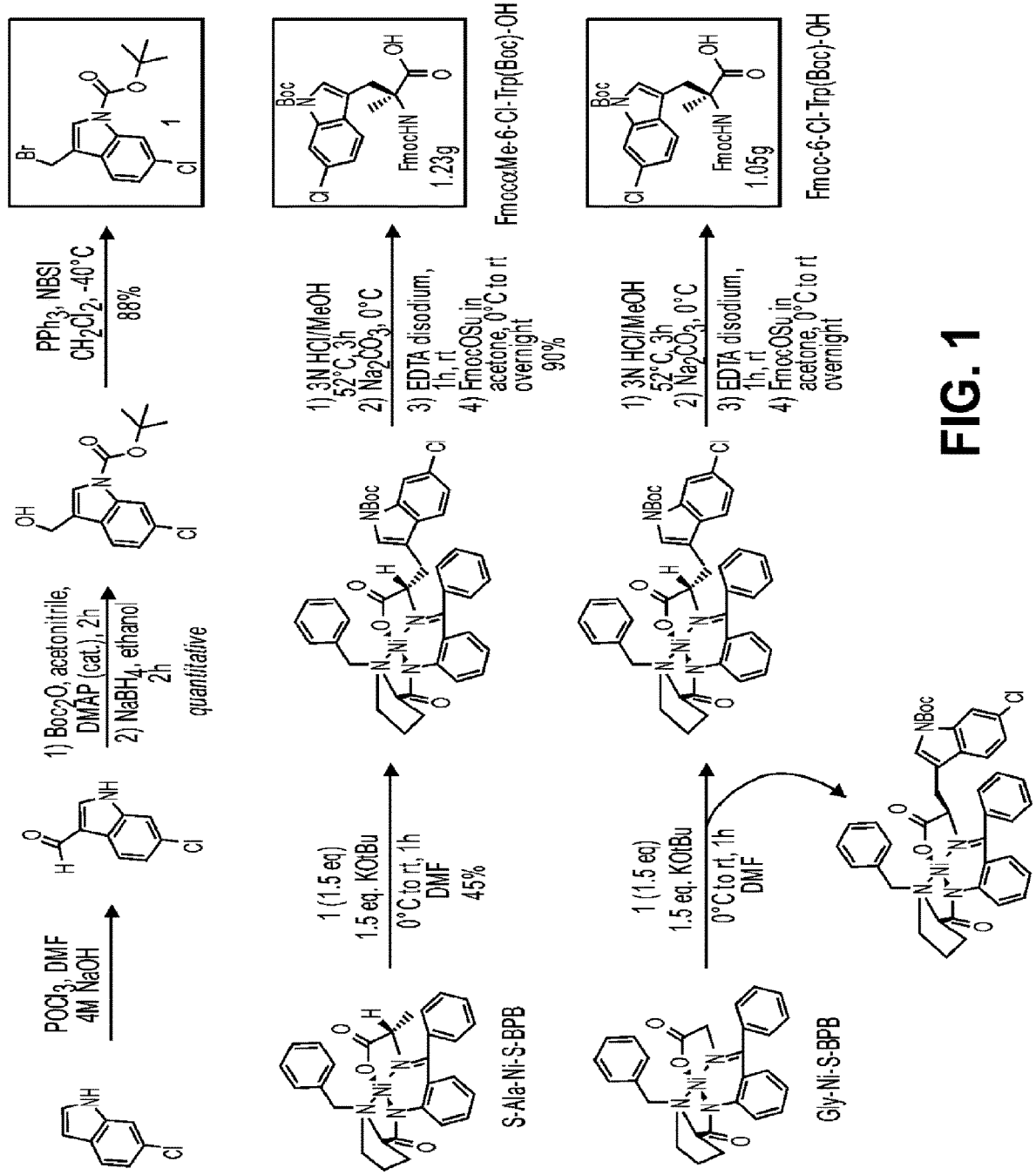
FIG. 1 describes the synthesis of Fmoc-Me-6-Chloro-Tryptophan & Fmoc-6-Chloro-Tryptophan.
Figure 2:
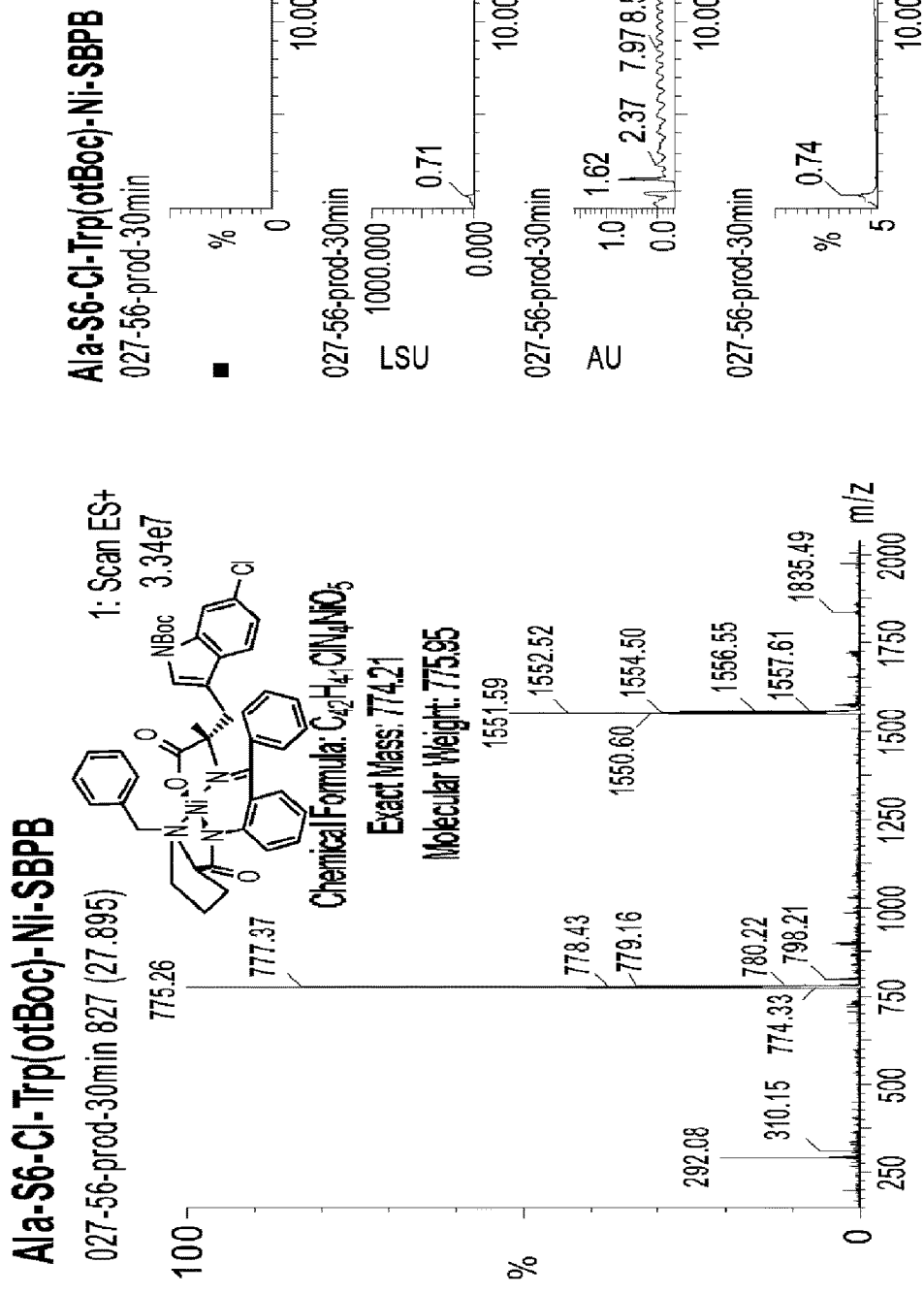
FIG. 2 shows an LC-MS trace of Me-6-Chloro-(Boc)Tryptophan-Ni—S—BPB.
Figure 3:
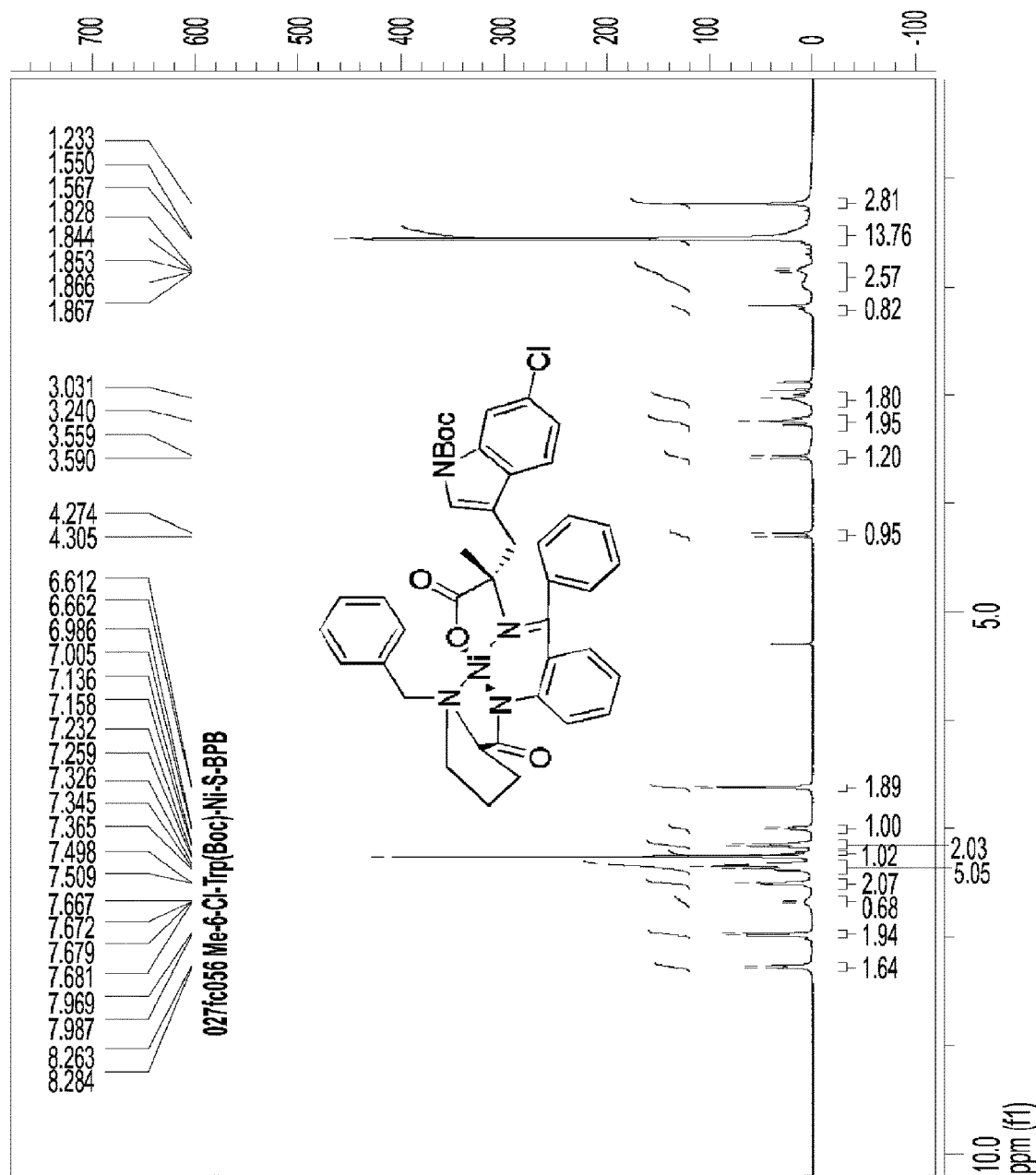
FIG. 3 shows a 1H-NMR spectrum of Me-6-Chloro-(Boc)Tryptophan-Ni—S—BPB.
Figure 4:
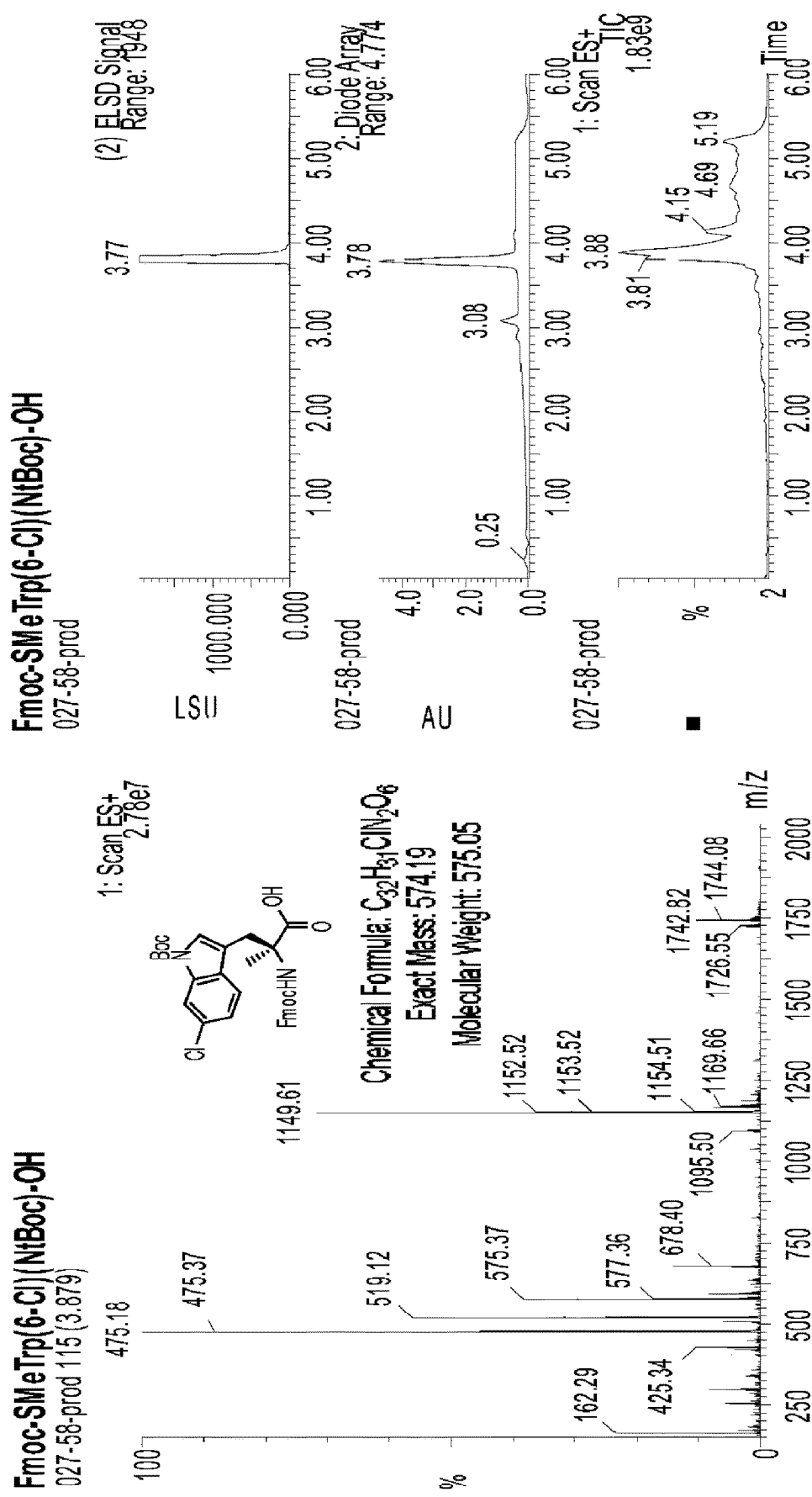
FIG. 4 shows an LC-MS trace of Fmoc-Me-6-Chloro-(Boc)Tryptophan.
Figure 5:
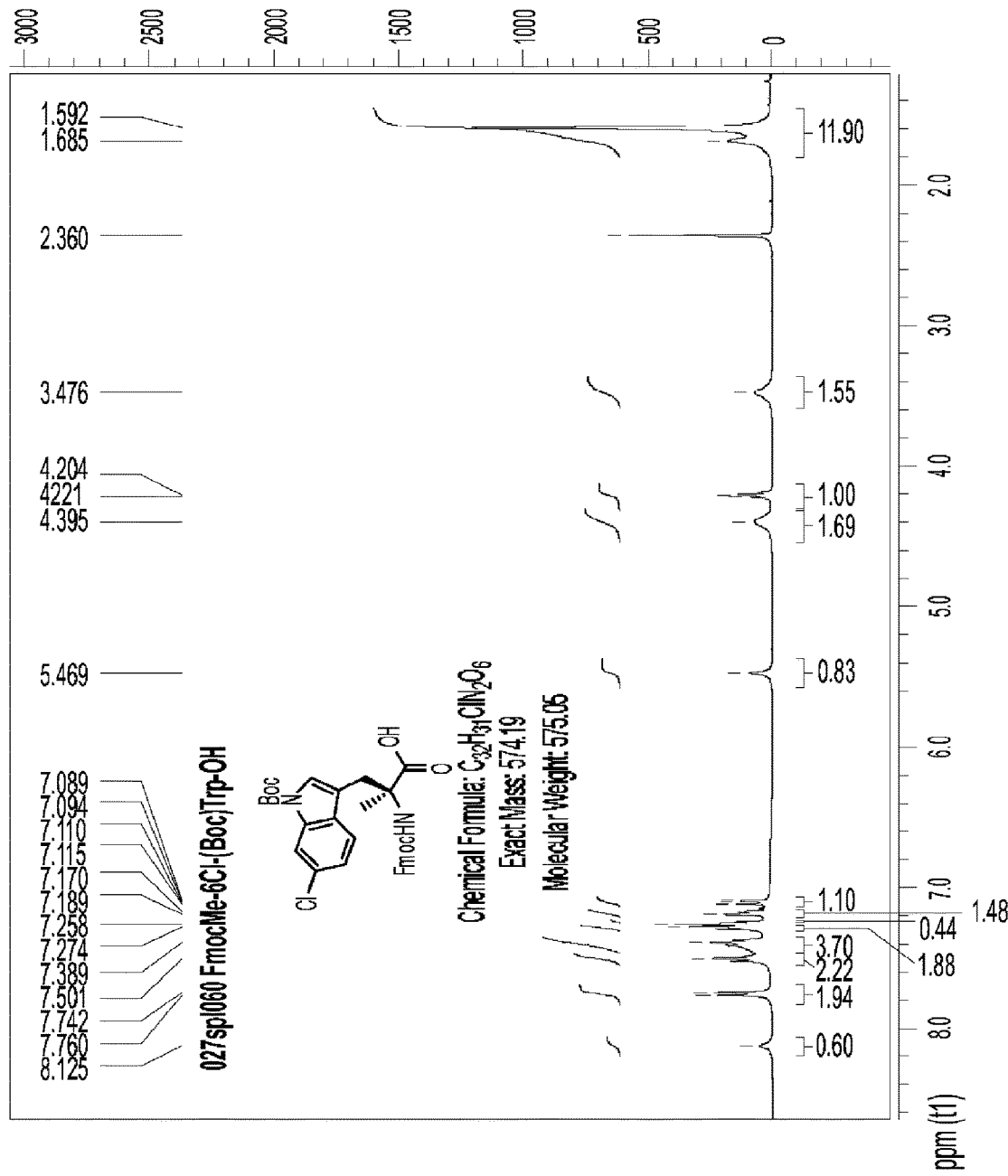
FIG. 5 shows a 1H-NMR spectrum of Fmoc-Me-6-Chloro-(Boc)Tryptophan.
Figure 8A:
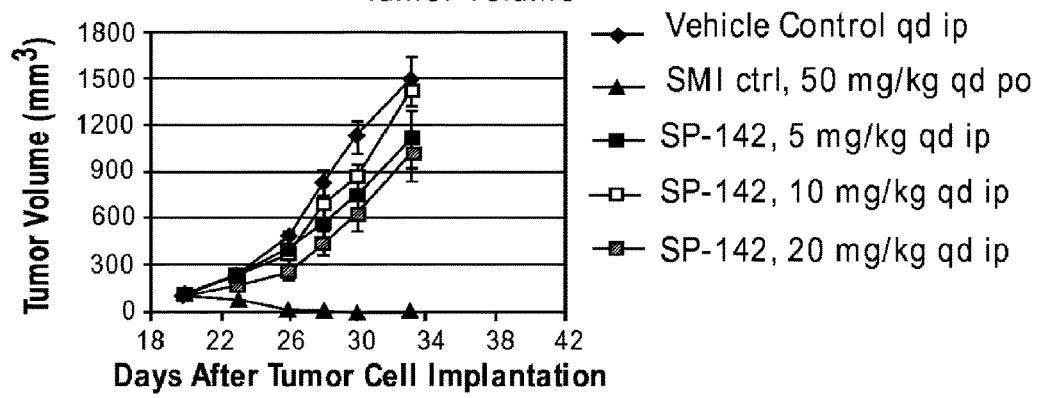
FIGS. 8A-B provide data from a variety of macrocycles.
Figure 8B:
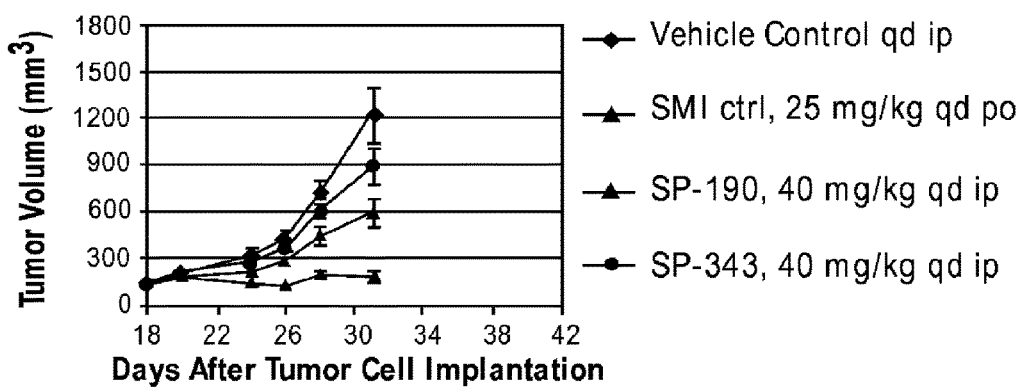

As used herein, the term "macrocycle" refers to a molecule having a chemical structure including a ring or cycle formed by at least 9 covalently bonded atoms.

As used herein, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycle include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle. A "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, the term "stability" refers to the maintenance of a defined secondary structure in solution by a peptidomimetic macrocycle of the invention as measured by circular dichroism, NMR or another biophysical measure, or resistance to proteolytic degradation in vitro or in vivo. Non-limiting examples of secondary structures contemplated in this invention are α-helices, β-turns, and β-pleated sheets.

As used herein, the term "helical stability" refers to the maintenance of a helical structure by a peptidomimetic macrocycle of the invention as measured by circular dichroism or NMR. For example, in some embodiments, the peptidomimetic macrocycles of the invention exhibit at least a 1.25, 1.5, 1.75 or 2-fold increase in α-helicity as determined by circular dichroism compared to a corresponding uncrosslinked macrocycle.

The term "α-amino acid" or simply "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" or "non-natural amino acid" refers to a molecule which is structurally similar to an amino acid and which can be substituted for an amino acid in the formation of a peptidomimetic macrocycle. Amino acid analogs include, without limitation, compounds which are structurally identical to an amino acid, as defined herein, except for the inclusion of one or more additional methylene groups between the amino and carboxyl group (e.g., α-amino β-carboxy acids), or for the substitution of the amino or carboxy group by a similarly reactive group (e.g., substitution of the primary amine with a secondary or tertiary amine, or substitution of the carboxy group with an ester). Non-natural amino acids include structures according to the following:

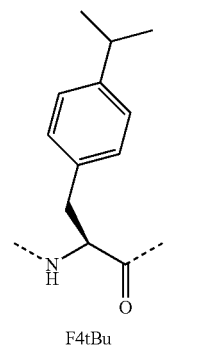

F4tBu

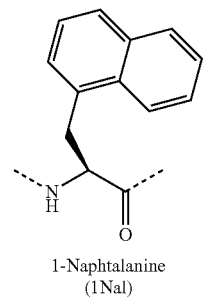

1-Naphtalanine
(1Nal)

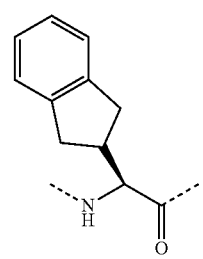

Indanyl glycine
(Igl)

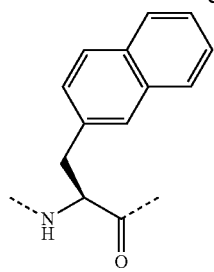
2-Naphtalanine (2Nal)
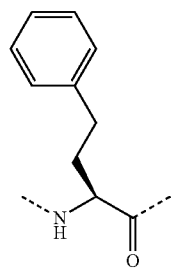
homophenylalanine (hF)
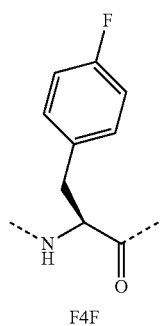
F4F
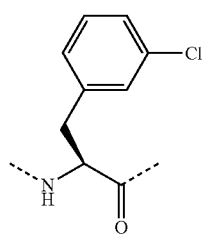
F3Cl = 3cf
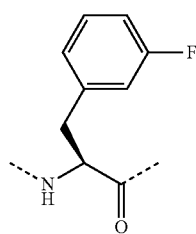
F3F = 3ff
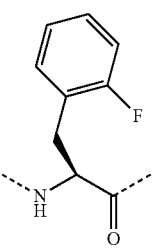
F2F = 2ff
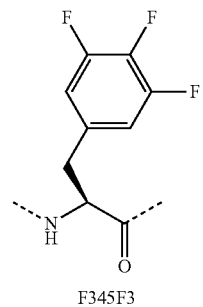
F345F3
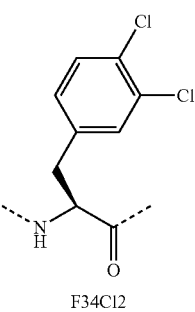
F34Cl2
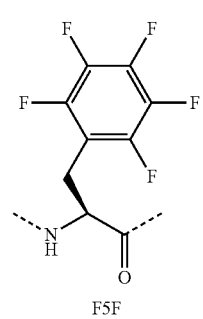
F5F
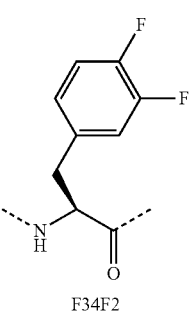
F34F2

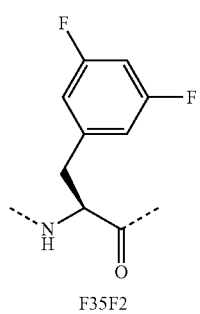
F35F2
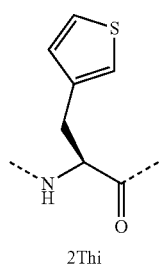
2Thi
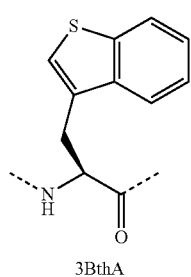
3BthA
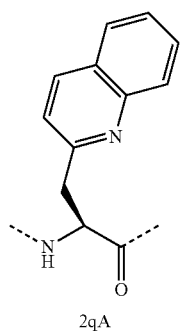
2qA
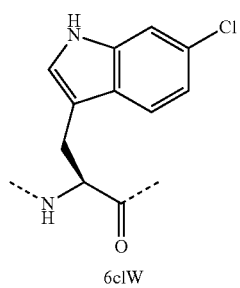
6clW
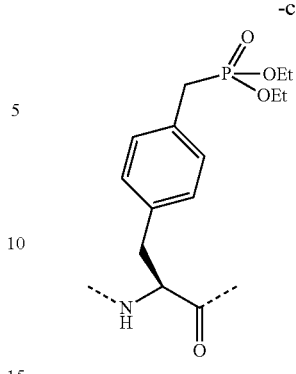
pmpEt
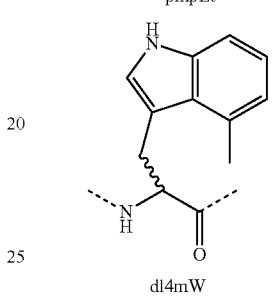
dl4mW
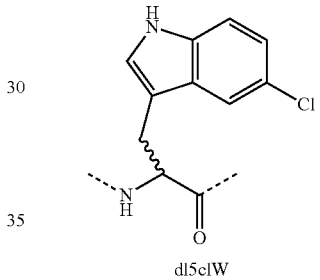
dl5clW
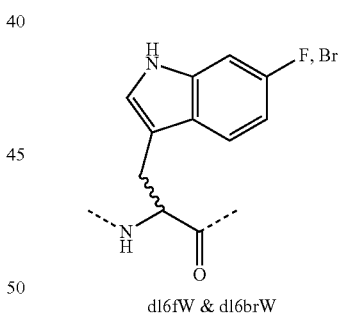
dl6fW & dl6brW
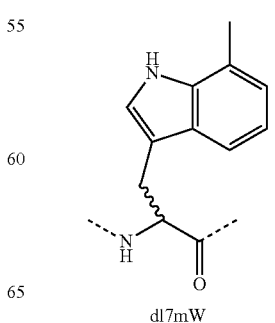
dl7mW -continued
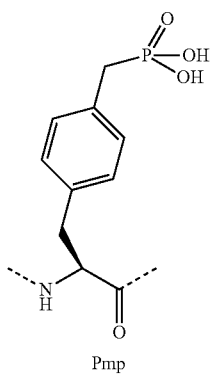
Pmp
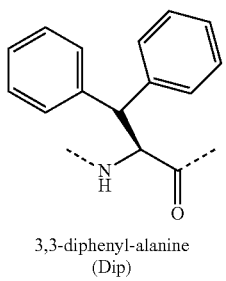
3,3-diphenyl-alanine
(Dip)
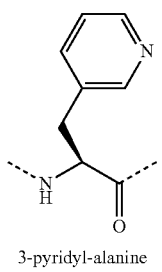
3-pyridyl-alanine
(3Pal)
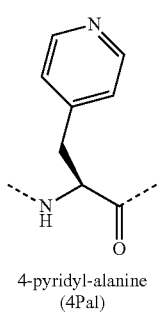
4-pyridyl-alanine
(4Pal)
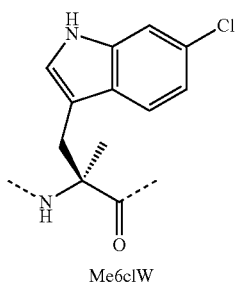
Me6clW
-continued
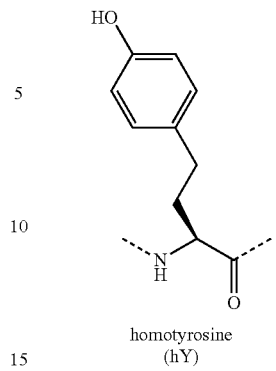
homotyrosine
(hY)
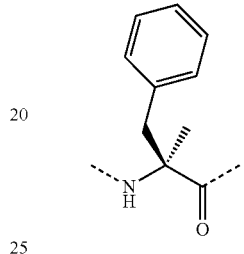
Amf
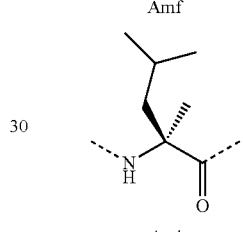
Aml
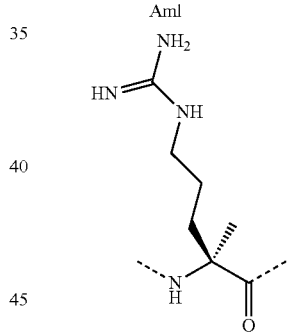
Amr
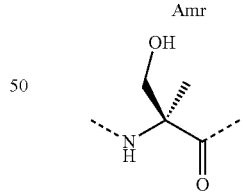
Ams
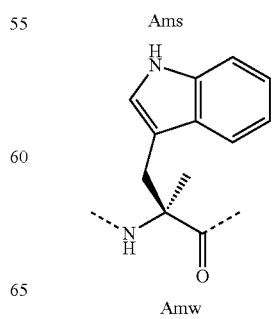
Amw

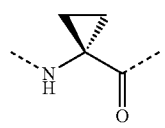
Ac3c
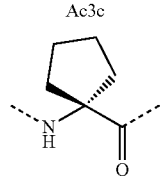
Ac5c
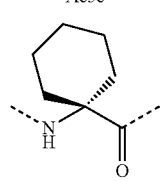
Ac6c
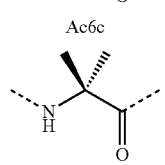
Aib
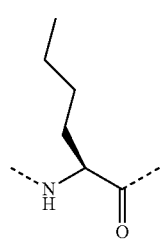
Norleucine
(Nle)
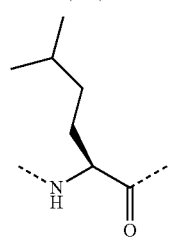
Homoleucine
(hL)
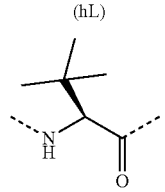
tert-Butyl glycine
(Tle)
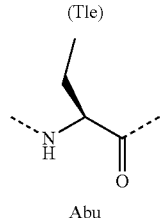
Abu
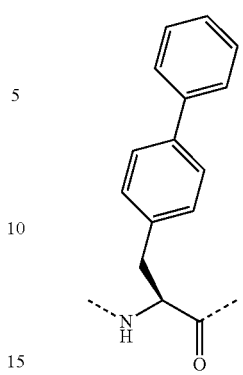
Bip
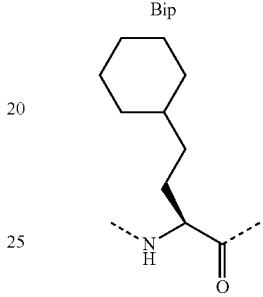
homocyclohexyl alanine
(hCha)
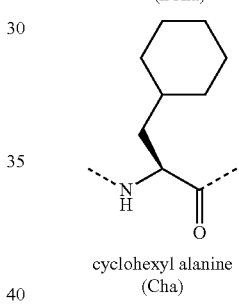
cyclohexyl alanine
(Cha)
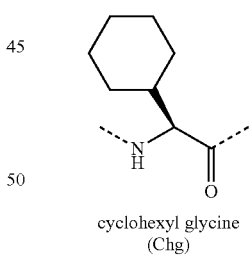
cyclohexyl glycine
(Chg)
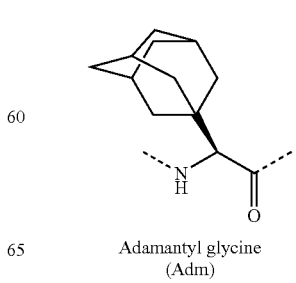
Adamantyl glycine
(Adm)

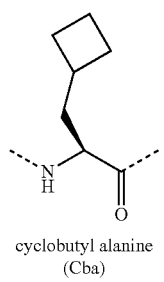
cyclobutyl alanine
(Cba)
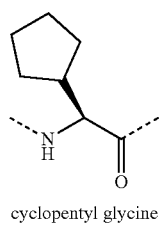
cyclopentyl glycine
(Cpg)
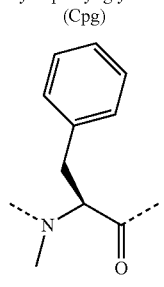
NmF
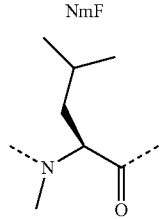
NmL
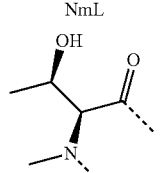
NmT
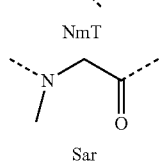
Sar
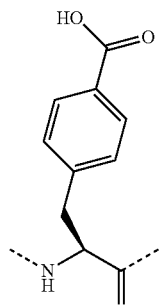
F4cooh
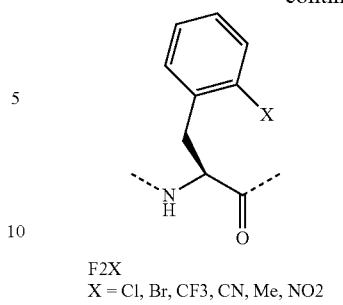
F2X
X = Cl, Br, CF3, CN, Me, NO2
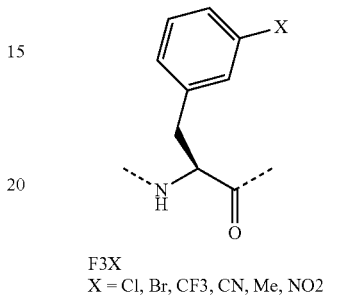
F3X
X = Cl, Br, CF3, CN, Me, NO2
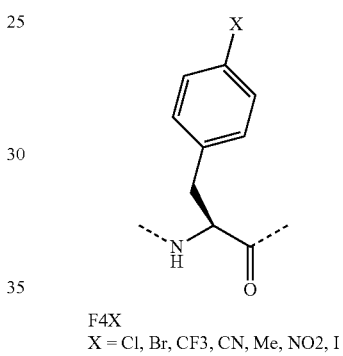
F4X
X = Cl, Br, CF3, CN, Me, NO2, I
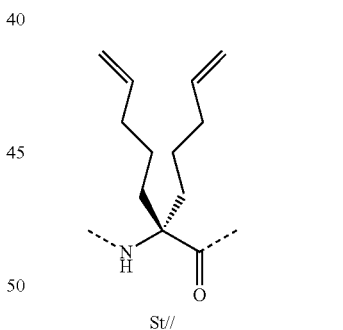
S5//
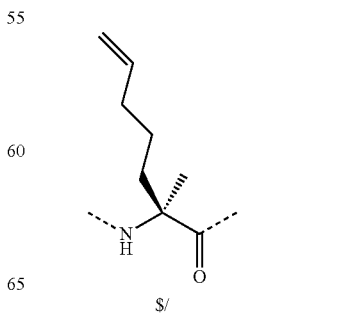
S5

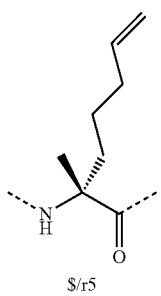

$/r5

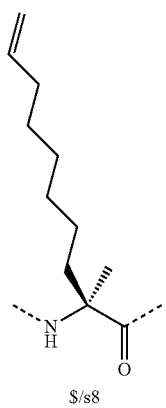

$/s8

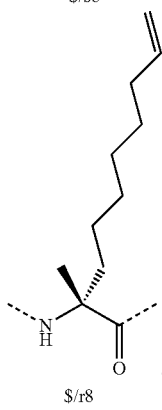

$/r8

A "non-essential" amino acid residue is a residue that can be altered from the wild-type sequence of a polypeptide without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "capping group" refers to the chemical moiety occurring at either the carboxy or amino terminus of the polypeptide chain of the subject peptidomimetic macrocycle. The capping group of a carboxy terminus includes an unmodified carboxylic acid (ie —COOH) or a carboxylic acid with a substituent. For example, the carboxy terminus may be substituted with an amino group to yield a carboxamide at the C-terminus. Various substituents include but are not limited to primary and secondary amines, including pegylated secondary amines. Representative secondary amine capping groups for the C-terminus include:

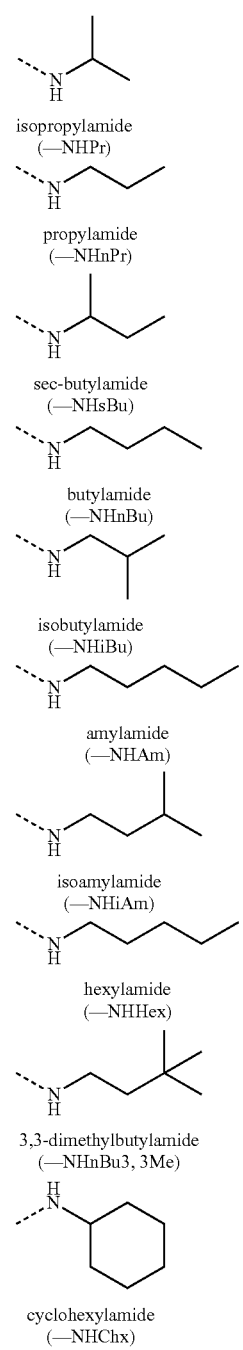

isopropylamide
(—NHPr)

propylamide
(—NHnPr)

sec-butylamide
(—NHsBu)

butylamide
(—NHnBu)

isobutylamide
(—NHiBu)

amylamide
(—NHAm)

isoamylamide
(—NHiAm)

hexylamide
(—NHHex)

3,3-dimethylbutylamide
(—NHnBu3, 3Me)

cyclohexylamide
(—NHChx)

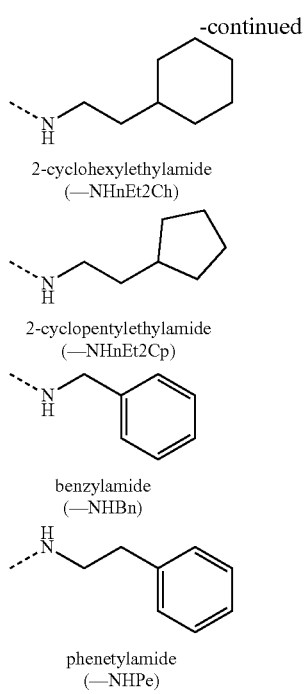

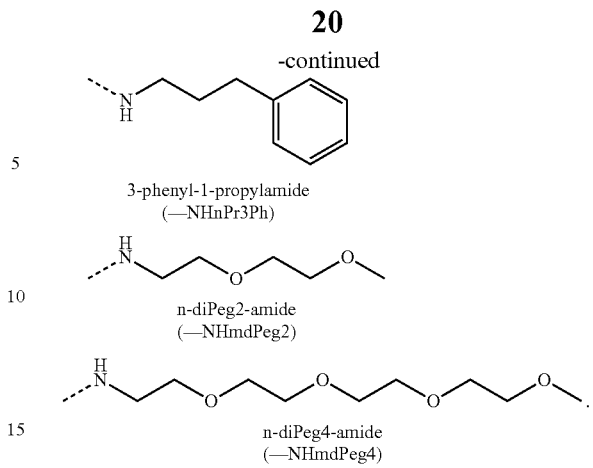

The capping group of an amino terminus includes an unmodified amine (ie —NH$_2$) or an amine with a substituent. For example, the amino terminus may be substituted with an acyl group to yield a carboxamide at the N-terminus. Various substituents include but are not limited to substituted acyl groups, including $C_1$-$C_6$ carbonyls, $C_7$-$C_{30}$ carbonyls, and pegylated carbamates. Representative capping groups for the N-terminus include:

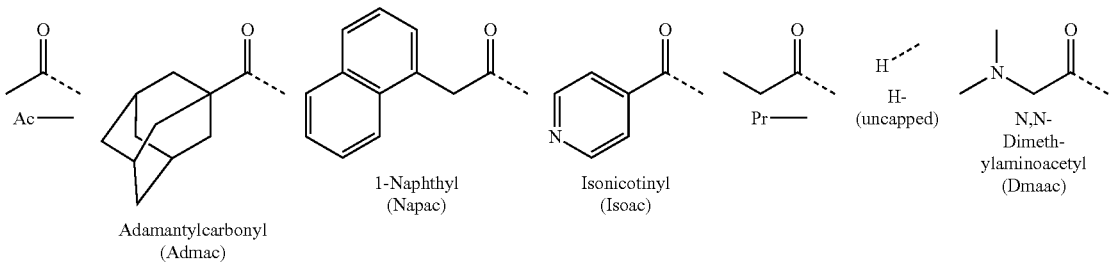

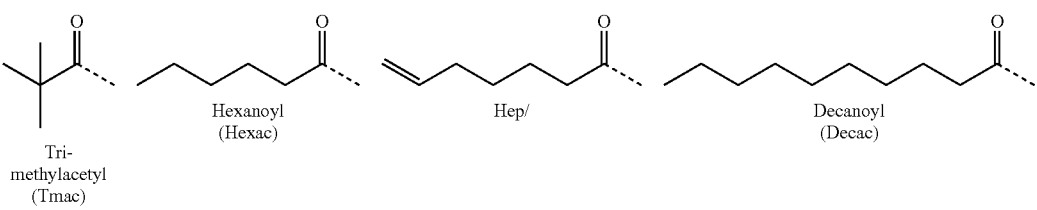

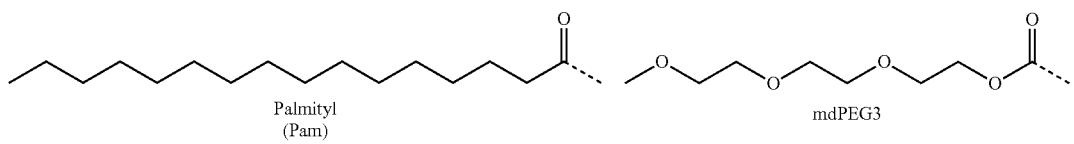

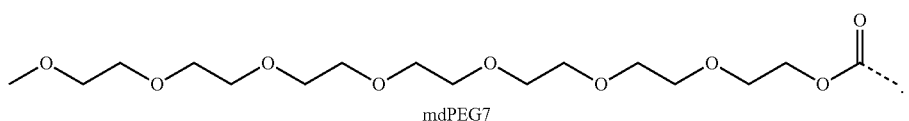

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol " ⫽ " when used as part of a molecular structure refers to a single bond or a trans or cis double bond.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The term "α,α di-substituted amino" acid refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "macrocyclization reagent" or "macrocycle-forming reagent" as used herein refers to any reagent which may be used to prepare a peptidomimetic macrocycle of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as Cu(CO$_2$CH$_3$)$_2$, CuSO$_4$, and CuCl$_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl(PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. Additional catalysts are disclosed in Grubbs et al., "Ring Closing Metathesis and Related Processes in Organic Synthesis" Ace. Chem. Res. 1995, 28, 446-452, and U.S. Pat. No. 5,811,515. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to a $C_1$-$C_5$ alkyl group, as defined above, wherein one of the $C_1$-$C_5$ alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—

C(O)—CH$_3$, —CH$_2$—CH$_2$—NH—C(O)—CH$_3$—CH$_3$, and —CH$_2$—CH$_2$—NH—C(O)—CH═CH$_2$.

"Alkanol" refers to a C$_1$-C$_5$ alkyl group, as defined above, wherein one of the C$_1$-C$_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$ CH$_2$CH$_2$OH, —CH$_2$CH(OH)CH$_3$, —CH$_2$CH(OH)CH$_2$CH$_3$, —CH(OH) CH$_3$ and —C(CH$_3$)$_2$CH$_2$OH.

"Alkylcarboxy" refers to a C$_1$-C$_5$ alkyl group, as defined above, wherein one of the C$_1$-C$_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., $p<0.1$) increase or decrease of at least 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The details of one or more particular embodiments of the invention are set forth in the accompanying drawings and the description below. Other features, objects, and advantages of the invention will be apparent from the description and drawings, and from the claims.

In some embodiments, the peptide sequences are derived from the p53 protein.

A non-limiting exemplary list of suitable p53 peptides for use in the present invention is given below.

TABLE 1

| Sequence (bold = critical residue; $\underline{X}$ = cross-linked amino acid) | | | | | | | | | | | | | | | | | Design Notes |
|---|---|---|---|---|---|---|---|---|---|---|---|---|---|---|---|---|---|
| Ac- | | Gln | Ser | Gln | Gln | Thr | Phe | Ser | Asn | Leu | Trp | Arg | Leu | Leu | Pro | Gln | Asn | —NH2 | linear |
| Ac- | $\underline{X}$ | Gln | Ser | Gln | $\underline{X}$ | Thr | Phe | Ser | Asn | Leu | Trp | Arg | Leu | Leu | Pro | Gln | Asn | —NH2 | i--> i + 4 x-link #1 |

TABLE 1-continued

| Sequence (bold = critical residue; X = cross-linked amino acid) | | | | | | | | | | | | | | | | | Design Notes |
|---|---|---|---|---|---|---|---|---|---|---|---|---|---|---|---|---|---|
| Ac- | X | Ser | Gln | Gln | X | Phe | Ser | Asn | Leu | Trp | Arg | Leu | Leu | Pro | Gln | Asn | —NH2 | i --> i + 4 x-link #2 |
| Ac- | | Gln | Ser | X | Gln | Thr | Phe | X | Asn | Leu | Trp | Arg | Leu | Leu | Pro | Gln | Asn | —NH2 | i --> i + 4 x-link #3 |
| Ac- | | Gln | Ser | Gln | X | Thr | Phe | Ser | X | Leu | Trp | Arg | Leu | Leu | Pro | Gln | Asn | —NH2 | i --> i + 4 x-link #4 |
| Ac- | | Gln | Ser | Gln | Gln | X | Phe | Ser | Asn | X | Trp | Arg | Leu | Leu | Pro | Gln | Asn | —NH2 | i --> i + 4 x-link #5 |
| Ac- | | Gln | Ser | Gln | Gln | Thr | Phe | X | Asn | Leu | Trp | X | Leu | Leu | Pro | Gln | Asn | —NH2 | i --> i + 4 x-link #6 |
| Ac- | | Gln | Ser | Gln | Gln | Thr | Phe | Ser | X | Leu | Trp | Arg | X | Leu | Pro | Gln | Asn | —NH2 | i --> i + 4 x-link #7 |
| Ac- | | Gln | Ser | Gln | Gln | The | Phe | Ser | Asn | Leu | Trp | X | Leu | Leu | Pro | X | Asn | —NH2 | i --> i + 4 x-link #8 |
| Ac- | | Gln | Ser | Gln | Gln | Thr | Phe | Ser | Asn | Leu | Trp | Arg | X | Leu | Pro | Gln | X | —NH2 | i --> i + 4 x-link #9 |
| Ac- | X | Gln | Ser | Gln | Gln | Thr | Phe | X | Asn | Leu | Trp | Arg | Leu | Leu | Pro | Gln | Asn | —NH2 | i --> i + 7 x-link #1 |
| Ac- | | X | Ser | Gln | Gln | Thr | Phe | Ser | X | Leu | Trp | Arg | Leu | Leu | Pro | Gln | Asn | —NH2 | i --> i + 7 x-link #2 |
| Ac- | | Gln | X | Gln | Gln | Thr | Phe | Ser | Asn | X | Trp | Arg | Leu | Leu | Pro | Gln | Asn | —NH2 | i --> i + 7 x-link #3 |
| Ac- | | Gln | Ser | Gln | X | Thr | Phe | Ser | Asn | Leu | Trp | X | Leu | Leu | Pro | Gln | Asn | —NH2 | i --> i + 7 x-link #4 |
| Ac- | | Gln | Ser | Gln | Gln | X | Phe | Ser | Asn | Leu | Trp | Arg | X | Leu | Pro | Gln | Asn | —NH2 | i --> i + 7 x-link #5 |
| Ac- | | Gln | Ser | Gln | Gln | Thr | Phe | X | Asn | Leu | Trp | Arg | Leu | Leu | X | Gln | Asn | —NH2 | i --> i + 7 x-link #6 |
| Ac- | | Gln | Ser | Gln | Gln | Thr | Phe | Ser | X | Leu | Trp | Arg | Leu | Leu | Pro | X | Asn | —NH2 | i --> i + 7 x-link #7 |
| Ac- | | Gln | Ser | Gln | Gln | Thr | Phe | Ser | Asn | X | Trp | Arg | Leu | Leu | Pro | Gln | X | —NH2 | i --> i + 7 x-link #8 |

TABLE 2

| Sequence (bold = critical residue; X = cross-linked amino acid) | | | | | | | | | | | | | Design Notes |
|---|---|---|---|---|---|---|---|---|---|---|---|---|---|
| Ac- | | Leu | Thr | Phe | Glu | His | Tyr | Trp | Ala | Gln | Leu | Thr | Ser | —NH2 | linear |
| Ac- | X | Leu | Thr | Phe | X | His | Tyr | Trp | Ala | Gln | Leu | Thr | Ser | —NH2 | i --> i + 4 x-link #1 |
| Ac- | | X | Thr | Phe | Glu | X | Tyr | Trp | Ala | Gln | Leu | Thr | Ser | —NH2 | i --> i + 4 x-link #2 |
| Ac- | | Leu | X | Phe | Glu | His | X | Trp | Ala | Gln | Leu | Thr | Ser | —NH2 | i --> i + 4 x-link #3 |
| Ac- | | Leu | Thr | Phe | X | His | Tyr | Trp | X | Gln | Leu | Thr | Ser | —NH2 | i --> i + 4 x-link #4 |
| Ac- | | Leu | Thr | Phe | Glu | X | Tyr | Trp | Ala | X | Leu | Thr | Ser | —NH2 | i --> i + 4 x-link #5 |
| Ac- | | Leu | Thr | Phe | Glu | His | Tyr | Trp | X | Gln | Leu | Thr | X | —NH2 | i --> i + 4 x-link #6 |
| Ac- | | Leu | Thr | Phe | Glu | His | Tyr | Trp | Ala | X | Leu | Thr | Ser | X | —NH2 | i --> i + 4 x-link #7 |
| Ac- | X | Thr | Phe | Glu | His | Tyr | Trp | X | Gln | Leu | Thr | Ser | —NH2 | i --> i + 7 x-link #1 |
| Ac- | Gln | X | Phe | Glu | His | Tyr | Trp | Ala | X | Leu | Thr | Ser | —NH2 | i --> i + 7 x-link #2 |
| Ac- | Gln | Thr | Phe | X | His | Tyr | Trp | Ala | Gln | X | Ser | —NH2 | i --> i + 7 x-link #3 |
| Ac- | Gln | Thr | Phe | Glu | X | Tyr | Trp | Ala | Gln | Leu | Thr | X | —NH2 | i --> i + 7 x-link #4 |
| Ac- | Gln | Thr | Phe | Glu | His | X | Trp | Ala | Gln | Leu | Thr | Ser | X | —NH2 | i --> i + 7 x-link #5 |

TABLE 3

| Sequence (bold = critical residue; X = cross-linked amino acid) | | | | | | | | | | | | Design Notes |
|---|---|---|---|---|---|---|---|---|---|---|---|---|
| Ac- |   | Phe | Met | Aib/His/Asn | Tyr | 6-ClTrp | Glu | Ac3c/Gln/Leu | Leu |   | —NH2 | linear |
| Ac- | X | Phe | Met | Aib/His/Asn | X | 6-ClTrp | Glu | Ac3c/Gln/Leu | Leu |   | —NH2 | i --> i + 4 x-link #1 |
| Ac- |   | Phe | X | Aib/His/Asn | Tyr | 6-ClTrp | X | Ac3c/Gln/Leu | Leu |   | —NH2 | i --> i + 4 x-link #2 |
| Ac- |   | Phe | Met | X | Tyr | 6-ClTrp | Glu | X | Leu |   | —NH2 | i --> i + 4 x-link #3 |
| Ac- | X | Phe | Met | Aib/His/Asn | Tyr | 6-ClTrp | Glu | X | Leu |   | —NH2 | i --> i + 7 x-link #1 |
| Ac- |   | Phe | X | Aib/His/Asn | Tyr | 6-ClTrp | Glu | Ac3c/Gln/Leu | Leu | X | —NH2 | i --> i + 7 x-link #2 |

In Table 3 and elsewhere, "Aib" represents a 2-aminoisobutyric acid residue, while "Ac3c" represents a aminocyclopropane carboxylic acid residue.

Peptidomimetic Macrocycles

In some embodiments, a peptidomimetic macrocycle of the invention has the Formula (I):

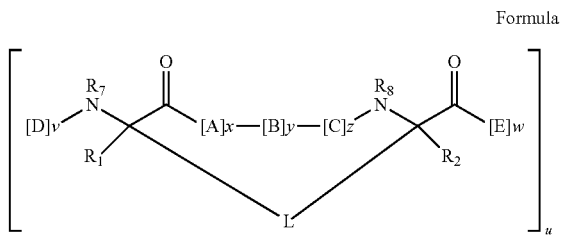

Formula I wherein:

each A, C, D, and E is independently a natural or non-natural amino acid, and the terminal D and E independently optionally include a capping group;

B is a natural or non-natural amino acid, amino acid analog,

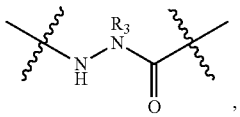

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

v and w are independently integers from 1-1000;

u is an integer from 1-10;

x, y and z are independently integers from 0-10; and n is an integer from 1-5.

In one embodiment, $L_1$ and $L_2$, either alone or in combination, do not form a triazole or a thioether.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges. Similarly, when u is greater than 1, each compound of the invention may encompass peptidomimetic macrocycles which are the same or different. For example, a compound of the invention may comprise peptidomimetic macrocycles comprising different linker lengths or chemical compositions.

In some embodiments, the peptidomimetic macrocycle of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

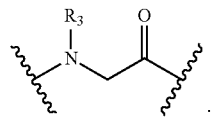

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

In one embodiment, the peptidomimetic macrocycle of Formula (I) is:

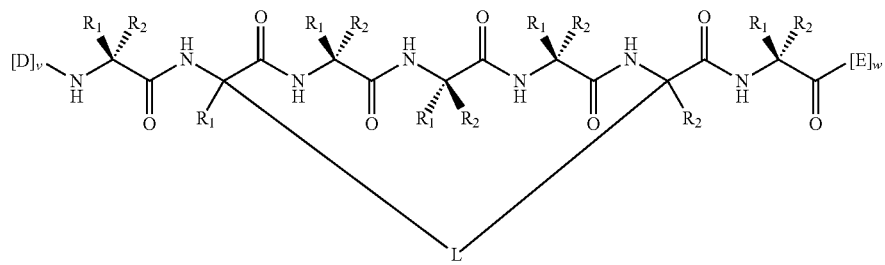

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the peptidomimetic macrocycle of Formula (I) is:

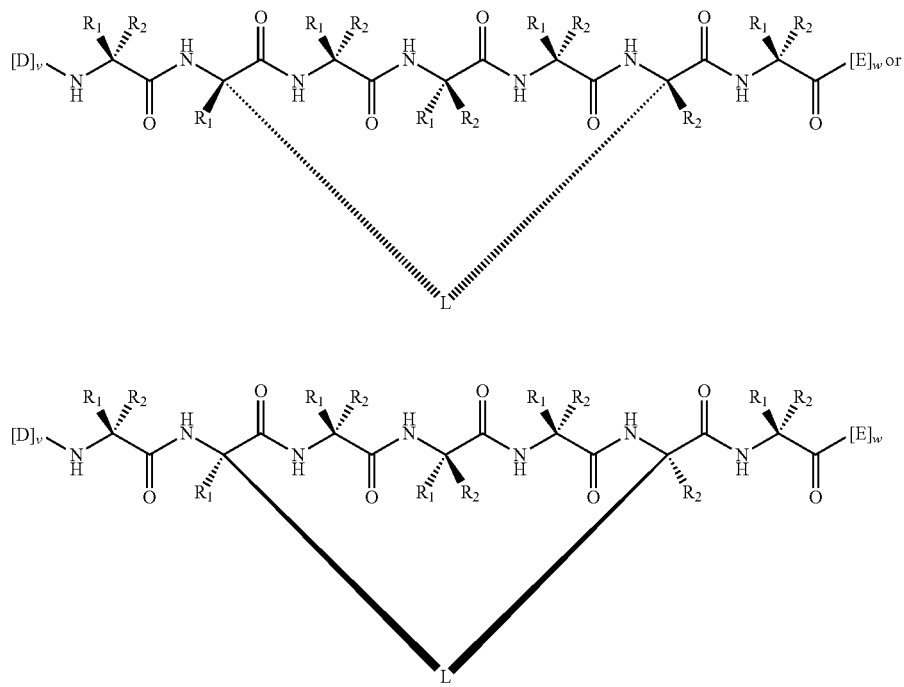

In other embodiments, the peptidomimetic macrocycle of Formula (I) is a compound of any of the formulas shown below:

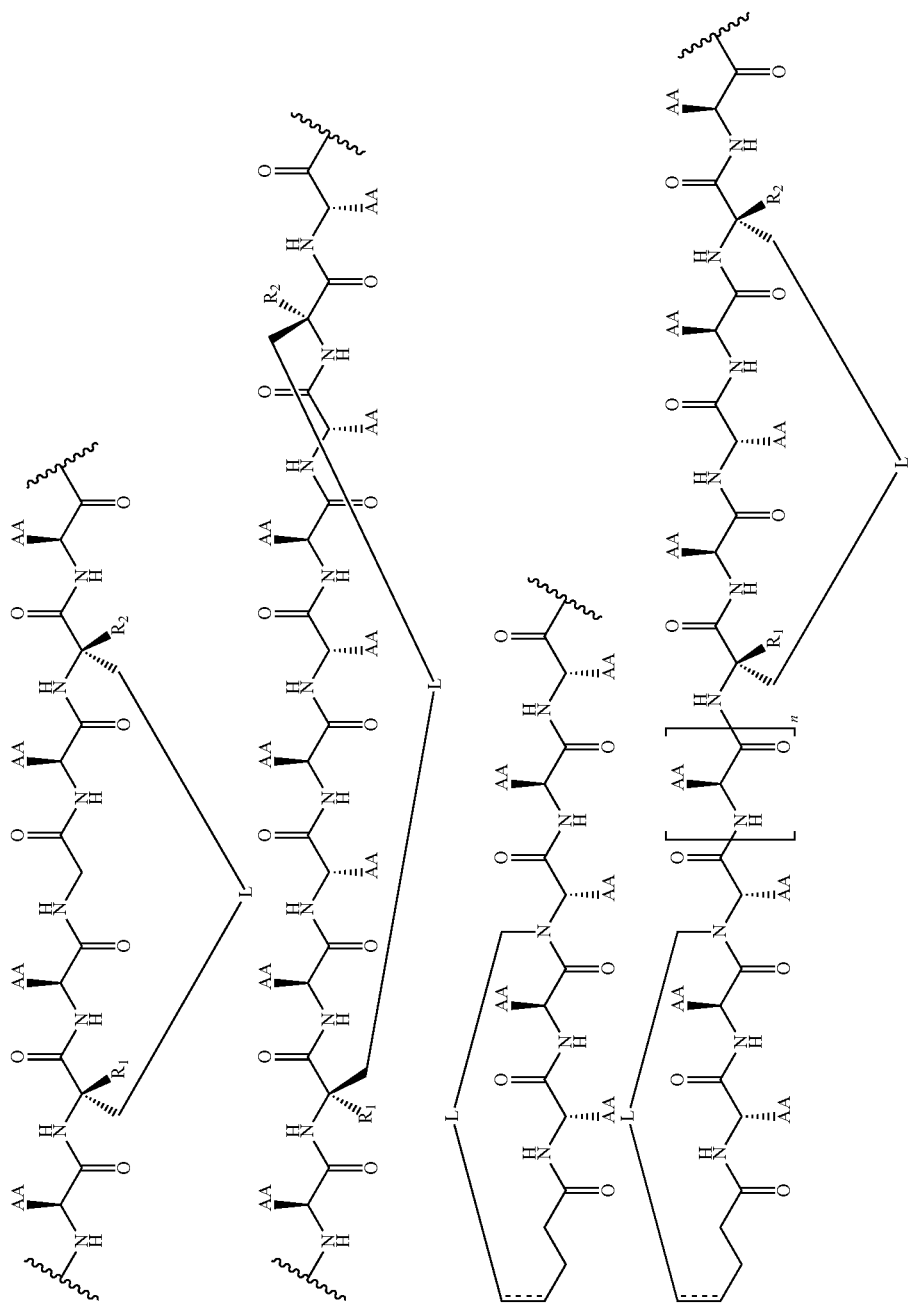

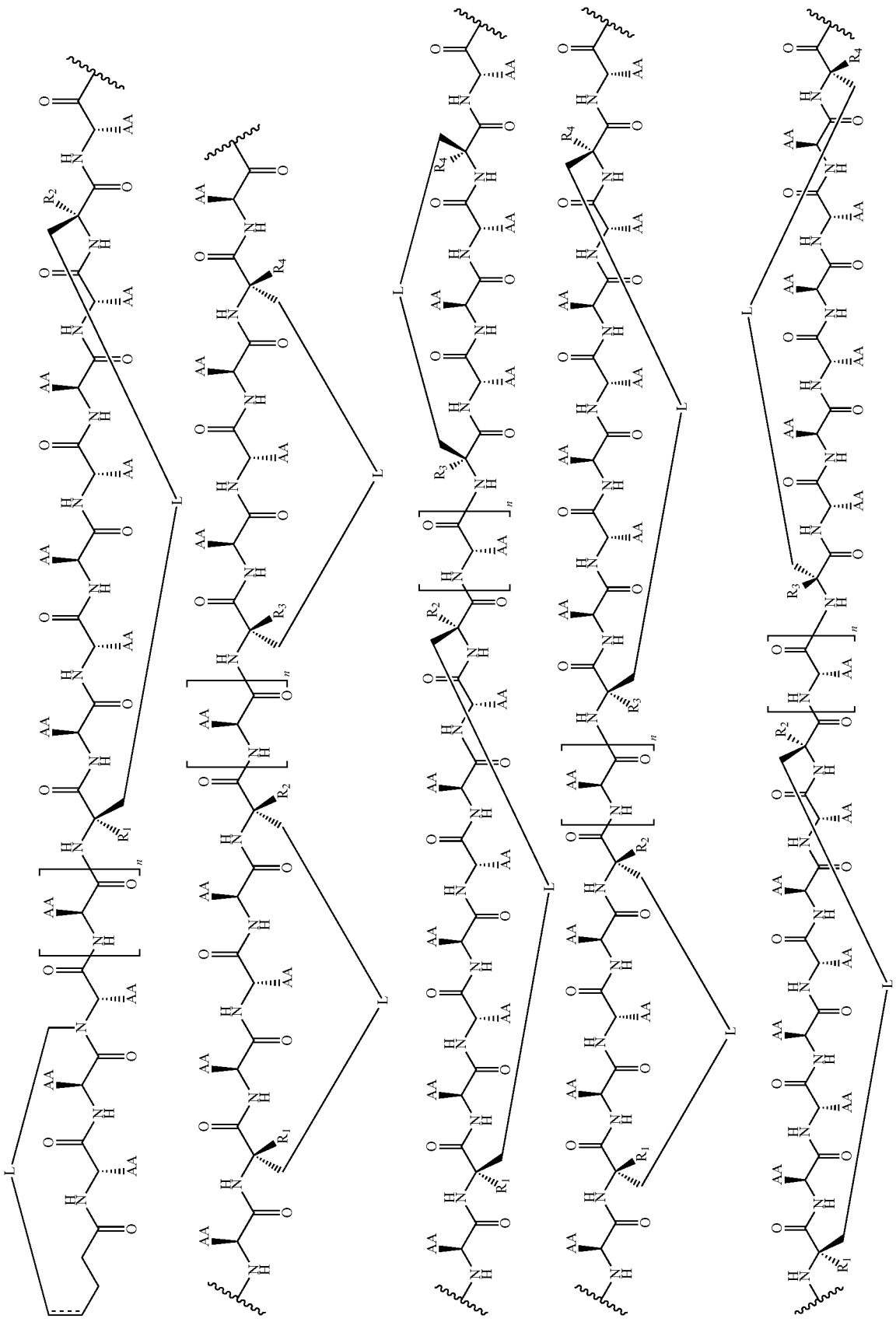

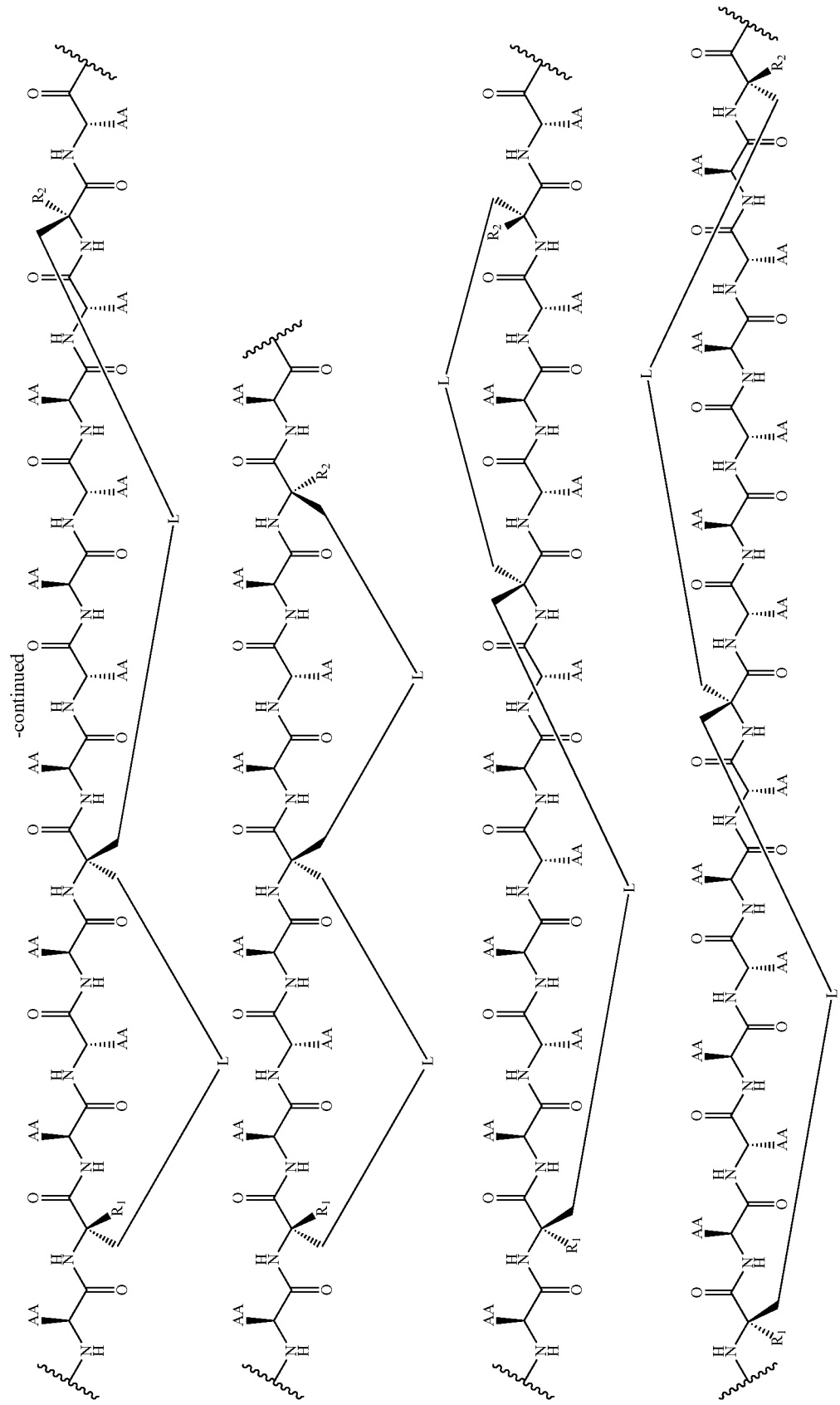

wherein "AA" represents any natural or non-natural amino acid side chain and "⌇" is [D]$_v$, [E]$_w$ as defined above, and n is an integer between 0 and 20, 50, 100, 200, 300, 400 or 500. In some embodiments, n is 0. In other embodiments, n is less than 50.

Exemplary embodiments of the macrocycle-forming linker L are shown below.

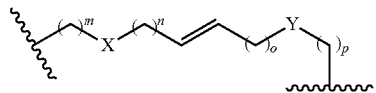

where X, Y = —CH$_2$—, O, S, or NH
m, n, o, p = 0-10

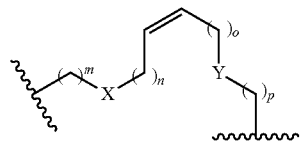

where X, Y = —CH$_2$—,
O, S, or NH
m, n, o, p = 0-10

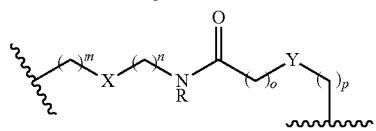

where X, Y = —CH$_2$—, O, S, or NH
m, n, o, p = 0-10
R = H, alkyl, other substituent

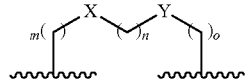

where X, Y = —CH$_2$—,
O, S, or NH
m, n, o = 0-10

In other embodiments, D and/or E in the compound of Formula I are further modified in order to facilitate cellular uptake. In some embodiments, lipidating or PEGylating a peptidomimetic macrocycle facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I represents a moiety comprising an additional macrocycle-forming linker such that the peptidomimetic macrocycle comprises at least two macrocycle-forming linkers. In a specific embodiment, a peptidomimetic macrocycle comprises two macrocycle-forming linkers. In an embodiment, u is 2.

In the peptidomimetic macrocycles of the invention, any of the macrocycle-forming linkers described herein may be used in any combination with any of the sequences shown in Tables 1-4 and also with any of the R— substituents indicated herein.

In some embodiments, the peptidomimetic macrocycle comprises at least one α-helix motif. For example, A, B and/or C in the compound of Formula I include one or more α-helices. As a general matter, α-helices include between 3 and 4 amino acid residues per turn. In some embodiments, the α-helix of the peptidomimetic macrocycle includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the peptidomimetic macrocycle. Thus, in some embodiments, the length of the macrocycle-forming linker L from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In other embodiments, the invention provides peptidomimetic macrocycles of Formula (IV) or (IVa):

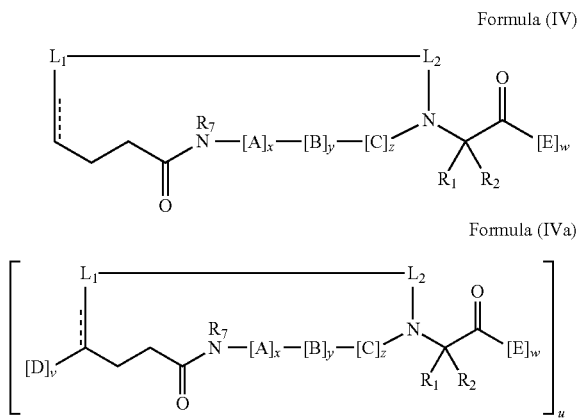

wherein:

each A, C, D, and E is independently a natural or non-natural amino acid, and the terminal D and E independently optionally include a capping group;

B is a natural or non-natural amino acid, amino acid analog,

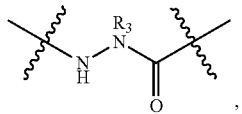

[—NH-L$_3$-CO—], [—NH-L$_3$-SO$_2$—], or [—NH-L$_3$-];

R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;

L is a macrocycle-forming linker of the formula -L$_1$-L$_2$-;

L$_1$ and L$_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;

v and w are independently integers from 1-1000;

u is an integer from 1-10;

x, y and z are independently integers from 0-10; and n is an integer from 1-5.

In one example, L$_1$ and L$_2$, either alone or in combination, do not form a triazole or a thioether.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, x+y+z is at least 1. In other embodiments of the invention, x+y+z is at least 2. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

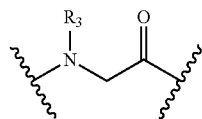

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

Exemplary embodiments of the macrocycle-forming linker -L$_1$-L$_2$- are shown below.

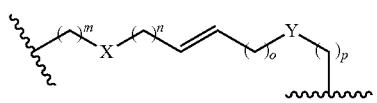

where X, Y = —CH$_2$—, O, S, or NH m, n, o, p = 0-10

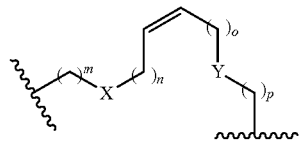

where X, Y = —CH$_2$—,

O, S, or NH m, n, o, p = 0-10

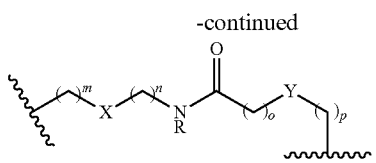

where X, Y = —CH₂—, O, S, or NH
m, n, o, p = 0-10
R = H, alkyl, other substituent

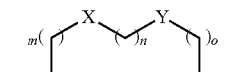

where X, Y = —CH₂—,
O, S, or NH
m, n, o = 0-10

Preparation of Peptidomimetic Macrocycles

Peptidomimetic macrocycles of the invention may be prepared by any of a variety of methods known in the art. For example, any of the residues indicated by "X" in Tables 1, 2, 3, or 4 may be substituted with a residue capable of forming a crosslinker with a second residue in the same molecule or a precursor of such a residue.

Various methods to effect formation of peptidomimetic macrocycles are known in the art. For example, the preparation of peptidomimetic macrocycles of Formula I is described in Schafmeister et al., J. Am. Chem. Soc. 122: 5891-5892 (2000); Schafmeister & Verdine, J. Am. Chem. Soc. 122:5891 (2005); Walensky et al., Science 305:1466-1470 (2004); U.S. Pat. No. 7,192,713 and PCT application WO 2008/121767. The α,α-disubstituted amino acids and amino acid precursors disclosed in the cited references may be employed in synthesis of the peptidomimetic macrocycle precursor polypeptides. For example, the "S5-olefin amino acid" is (S)-α-(2'-pentenyl) alanine and the "R8 olefin amino acid" is (R)-α-(2'-octenyl) alanine. Following incorporation of such amino acids into precursor polypeptides, the terminal olefins are reacted with a metathesis catalyst, leading to the formation of the peptidomimetic macrocycle. In various embodiments, the following amino acids may be employed in the synthesis of the peptidomimetic macrocycle:

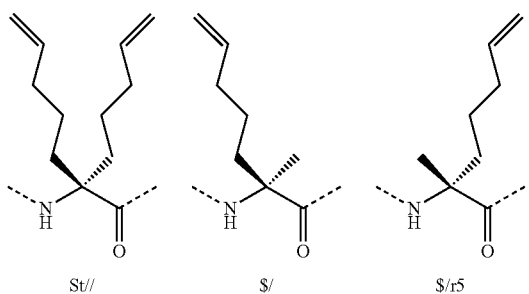

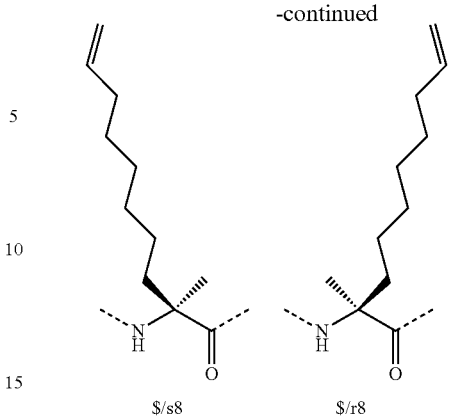

In other embodiments, the peptidomimetic macrocycles of the invention are of Formula IV or IVa. Methods for the preparation of such macrocycles are described, for example, in U.S. Pat. No. 7,202,332.

Additional methods of forming peptidomimetic macrocycles which are envisioned as suitable to perform the present invention include those disclosed by Mustapa, M. Firouz Mohd et al., J. Org. Chem (2003), 68, pp. 8193-8198; Yang, Bin et al. Bioorg Med. Chem. Lett. (2004), 14, pp. 1403-1406; U.S. Pat. Nos. 5,364,851; 5,446,128; 5,824,483; 6,713,280; and 7,202,332. In such embodiments, aminoacid precursors are used containing an additional substituent R— at the alpha position. Such aminoacids are incorporated into the macrocycle precursor at the desired positions, which may be at the positions where the crosslinker is substituted or, alternatively, elsewhere in the sequence of the macrocycle precursor. Cyclization of the precursor is then effected according to the indicated method.

Assays

The properties of the peptidomimetic macrocycles of the invention are assayed, for example, by using the methods described below. In some embodiments, a peptidomimetic macrocycle of the invention has improved biological properties relative to a corresponding polypeptide lacking the substituents described herein.

Assay to Determine α-Helicity.

In solution, the secondary structure of polypeptides with α-helical domains will reach a dynamic equilibrium between random coil structures and α-helical structures, often expressed as a "percent helicity". Thus, for example, alpha-helical domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocycles of the invention, the compounds are dissolved in an aqueous solution (e.g. 50 mM potassium phosphate solution at pH 7, or distilled H₂O, to concentrations of 25-50 μM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/scc; accumulations, 10; response, 1 sec; bandwidth, 1 nm; path length, 0.1 cm). The α-helical content of each peptide is calculated by dividing the mean residue ellipticity (e.g. [Φ]222 obs) by the reported value for a model helical decapeptide (Yang et al. (1986), Methods Enzymol. 130:208)).

Assay to Determine Melting Temperature (Tm).

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on melting temperature, peptidomimetic macrocycles or unmodified peptides are dissolved in distilled $H_2O$ (e.g. at a final concentration of 50 μM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time (k=−1×slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and a corresponding uncrosslinked polypeptide (2 mcg) are incubated with fresh mouse, rat and/or human serum (2 mL) at 37° C. for 0, 1, 2, 4, 8, and 24 hours. To determine the level of intact compound, the following procedure may be used: The samples are extracted by transferring 100 μl of sera to 2 ml centrifuge tubes followed by the addition of 10 μL of 50% formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis.

In Vitro Binding Assays.

To assess the binding and affinity of peptidomimetic macrocycles and peptidomimetic precursors to acceptor proteins, a fluorescence polarization assay (FPA) issued, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LS50B). Kd values may be determined by non-linear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide.

In Vitro Displacement Assays to Characterize Antagonists of Peptide-Protein Interactions.

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.).

Any class of molecule, such as small organic molecules, peptides, oligonucleotides or proteins can be examined as putative antagonists in this assay.

Assay for Protein-Ligand Binding by Affinity Selection-Mass Spectrometry

To assess the binding and affinity of test compounds for proteins, an affinity-selection mass spectrometry assay is used, for example. Protein-ligand binding experiments are conducted according to the following representative procedure outlined for a system-wide control experiment using 1 μM peptidomimetic macrocycle plus 5 μM hMDM2. A 1 μL DMSO aliquot of a 40 μM stock solution of peptidomimetic macrocycle is dissolved in 19 μL of PBS (Phosphate-buffered saline: 50 mM, pH 7.5 Phosphate buffer containing 150 mM NaCl). The resulting solution is mixed by repeated pipetting and clarified by centrifugation at 10 000 g for 10 min. To a 4 μL aliquot of the resulting supernatant is added 4 μL of 10 μM hMDM2 in PBS. Each 8.0 μL experimental sample thus contains 40 pmol (1.5 μg) of protein at 5.0 μM concentration in PBS plus 1 μM peptidomimetic macrocycle and 2.5% DMSO. Duplicate samples thus prepared for each concentration point are incubated for 60 min at room temperature, and then chilled to 4° C. prior to size-exclusion chromatography-LC-MS analysis of 5.0 µL injections. Samples containing a target protein, protein-ligand complexes, and unbound compounds are injected onto an SEC column, where the complexes are separated from non-binding component by a rapid SEC step. The SEC column eluate is monitored using UV detectors to confirm that the early-eluting protein fraction, which elutes in the void volume of the SEC column, is well resolved from unbound components that are retained on the column. After the peak containing the protein and protein-ligand complexes elutes from the primary UV detector, it enters a sample loop where it is excised from the flow stream of the SEC stage and transferred directly to the LC-MS via a valving mechanism. The $(M+3H)^{3+}$ ion of the peptidomimetic macrocycle is observed by ESI-MS at the expected m/z, confirming the detection of the protein-ligand complex.

Assay for Protein-Ligand Kd Titration Experiments.

To assess the binding and affinity of test compounds for proteins, a protein-ligand Kd titration experiment is performed, for example. Protein-ligand $K_d$ titrations experiments are conducted as follows: 2 µL DMSO aliquots of a serially diluted stock solution of titrant peptidomimetic macrocycle (5, 2.5, . . . , 0.098 mM) are prepared then dissolved in 38 µL of PBS. The resulting solutions are mixed by repeated pipetting and clarified by centrifugation at 10 000 g for 10 min. To 4.0 µL aliquots of the resulting supernatants is added 4.0 µL of 10 µM hMDM2 in PBS. Each 8.0 µL experimental sample thus contains 40 pmol (1.5 µg) of protein at 5.0 µM concentration in PBS, varying concentrations (125, 62.5, . . . , 0.24 µM) of the titrant peptide, and 2.5% DMSO. Duplicate samples thus prepared for each concentration point are incubated at room temperature for 30 min, then chilled to 4° C. prior to SEC-LC-MS analysis of 2.0 µL injections. The $(M+H)^{1+}$, $(M+2H)^{2+}$, $(M+3H)^{3+}$, and/or $(M+Na)^{1+}$ ion is observed by ESI-MS; extracted ion chromatograms are quantified, then fit to equations to derive the binding affinity $K_d$ as described in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry, System for the Discovery, and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Assay for Competitive Binding Experiments by Affinity Selection-Mass Spectrometry To determine the ability of test compounds to bind competitively to proteins, an affinity selection mass spectrometry assay is performed, for example. A mixture of ligands at 40 µM per component is prepared by combining 2 µL aliquots of 400 µM stocks of each of the three compounds with 14 µL of DMSO. Then, 1 µL aliquots of this 40 µM per component mixture are combined with 1 µL DMSO aliquots of a serially diluted stock solution of titrant peptidomimetic macrocycle (10, 5, 2.5, . . . , 0.078 mM). These 2 µL samples are dissolved in 38 µL of PBS. The resulting solutions were mixed by repeated pipetting and clarified by centrifugation at 10 000 g for 10 min. To 4.0 µL aliquots of the resulting supernatants is added 4.0 µL of 10 µM hMDM2 protein in PBS. Each 8.0 µL experimental sample thus contains 40 pmol (1.5 µg) of protein at 5.0 µM concentration in PBS plus 0.5 µM ligand, 2.5% DMSO, and varying concentrations (125, 62.5, . . . , 0.98 µM) of the titrant peptidomimetic macrocycle. Duplicate samples thus prepared for each concentration point are incubated at room temperature for 60 min, then chilled to 4° C. prior to SEC-LC-MS analysis of 2.0 µL injections. Additional details on these and other methods are provided in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Binding Assays in Intact Cells.

It is possible to measure binding of peptides or peptidomimetic macrocycles to their natural acceptors in intact cells by immunoprecipitation experiments. For example, intact cells are incubated with fluoresceinated (FITC-labeled) compounds for 4 hrs in the absence of serum, followed by serum replacement and further incubation that ranges from 4-18 hrs. Cells are then pelleted and incubated in lysis buffer (50 mM Tris [pH 7.6], 150 mM NaCl, 1% CHAPS and protease inhibitor cocktail) for 10 minutes at 4° C. Extracts are centrifuged at 14,000 rpm for 15 minutes and supernatants collected and incubated with 10 µl goat anti-FITC antibody for 2 hrs, rotating at 4° C. followed by further 2 hrs incubation at 4° C. with protein A/G Sepharose (50 µl of 50% bead slurry). After quick centrifugation, the pellets are washed in lysis buffer containing increasing salt concentration (e.g., 150, 300, 500 mM). The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the peptidomimetic macrocycle.

Cellular Penetrability Assays.

A peptidomimetic macrocycle is, for example, more cell penetrable compared to a corresponding uncrosslinked macrocycle. Peptidomimetic macrocycles with optimized linkers possess, for example, cell penetrability that is at least two-fold greater than a corresponding uncrosslinked macrocycle, and often 20% or more of the applied peptidomimetic macrocycle will be observed to have penetrated the cell after 4 hours. To measure the cell penetrability of peptidomimetic macrocycles and corresponding uncrosslinked macrocycle, intact cells are incubated with fluoresceinated peptidomimetic macrocycles or corresponding uncrosslinked macrocycle (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

Cellular Efficacy Assays.

The efficacy of certain peptidomimetic macrocycles is determined, for example, in cell-based killing assays using a variety of tumorigenic and non-tumorigenic cell lines and primary cells derived from human or mouse cell populations. Cell viability is monitored, for example, over 24-96 hrs of incubation with peptidomimetic macrocycles (0.5 to 50 μM) to identify those that kill at EC50<10 μM. Several standard assays that measure cell viability are commercially available and are optionally used to assess the efficacy of the peptidomimetic macrocycles. In addition, assays that measure Annexin V and caspase activation are optionally used to assess whether the peptidomimetic macrocycles kill cells by activating the apoptotic machinery. For example, the Cell Titer-glo assay is used which determines cell viability as a function of intracellular ATP concentration.

In Vivo Stability Assay.

To investigate the in vivo stability of the peptidomimetic macrocycles, the compounds are, for example, administered to mice and/or rats by IV, IP, PO or inhalation routes at concentrations ranging from 0.1 to 50 mg/kg and blood specimens withdrawn at 0', 5', 15', 30', 1 hr, 4 hrs, 8 hrs and 24 hours post-injection. Levels of intact compound in 25 μL of fresh serum are then measured by LC-MS/MS as above.

In Vivo Efficacy in Animal Models.

To determine the anti-oncogenic activity of peptidomimetic macrocycles of the invention in vivo, the compounds are, for example, given alone (IP, IV, PO, by inhalation or nasal routes) or in combination with sub-optimal doses of relevant chemotherapy (e.g., cyclophosphamide, doxorubicin, etoposide). In one example, $5 \times 10^6$ RS4; 11 cells (established from the bone marrow of a patient with acute lymphoblastic leukemia) that stably express luciferase are injected by tail vein in NOD-SCID mice 3 hrs after they have been subjected to total body irradiation. If left untreated, this form of leukemia is fatal in 3 weeks in this model. The leukemia is readily monitored, for example, by injecting the mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (10 days after injection/day 1 of experiment, in bioluminescence range of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation into NOD-SCID mice of DoHH2, a cell line derived from human follicular lymphoma, that stably expresses luciferase. These in vivo tests optionally generate preliminary pharmacokinetic, pharmacodynamic and toxicology data.

Clinical Trials.

To determine the suitability of the peptidomimetic macrocycles of the invention for treatment of humans, clinical trials are performed. For example, patients diagnosed with cancer and in need of treatment are selected and separated in treatment and one or more control groups, wherein the treatment group is administered a peptidomimetic macrocycle of the invention, while the control groups receive a placebo or a known anti-cancer drug. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocycle show improved long-term survival compared to a patient control group treated with a placebo.

Pharmaceutical Compositions and Routes of Administration

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, malcate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

Methods of Use

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the p53/HDMX system, labeled peptidomimetic macrocycles based on p53 can be used in a HDMX binding assay along with small molecules that competitively bind to HDMX. Competitive binding studies allow for rapid in vitro evaluation and determination of drug candidates specific for the p53/HDMX system. Such binding studies may be performed with any of the peptidomimetic macrocycles disclosed herein and their binding partners.

The invention further provides for the generation of antibodies against the peptidomimetic macrocycles. In some embodiments, these antibodies specifically bind both the peptidomimetic macrocycle and the precursor peptides, such as p53, to which the peptidomimetic macrocycles are related. Such antibodies, for example, disrupt the native protein-protein interaction, for example, binding between p53 and HDMX.

In other aspects, the present invention provides for both prophylactic and therapeutic methods of treating a subject at risk of (or susceptible to) a disorder or having a disorder associated with aberrant (e.g., insufficient or excessive) expression or activity of the molecules including p53, HDM2 or HDMX.

In another embodiment, a disorder is caused, at least in part, by an abnormal level of p53 or HDM2 or HDMX, (e.g., over or under expression), or by the presence of p53 or HDM2 or HDMX exhibiting abnormal activity. As such, the reduction in the level and/or activity of p53 or HDM2 or HDMX, or the enhancement of the level and/or activity of p53 or HDM2 or HDMX, by peptidomimetic macrocycles derived from p53, is used, for example, to ameliorate or reduce the adverse symptoms of the disorder.

In another aspect, the present invention provides methods for treating or preventing a disease including hyperproliferative disease and inflammatory disorder by interfering with the interaction or binding between binding partners, for example, between p53 and HDM2 or p53 and HDMX. These methods comprise administering an effective amount of a compound of the invention to a warm blooded animal, including a human. In some embodiments, the administration of the compounds of the present invention induces cell growth arrest or apoptosis.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the peptidomimetics macrocycles of the invention is used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetics macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), *Crit Rev. Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In other or further embodiments, the peptidomimetics macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, and myelodysplasia.

In other or further embodiments, the peptidomimetics macrocycles of the invention that act to decrease apoptosis are used to treat disorders associated with an undesirable level of cell death. Thus, in some embodiments, the anti-apoptotic peptidomimetics macrocycles of the invention are used to treat disorders such as those that lead to cell death associated with viral infection, e.g., infection associated with infection with human immunodeficiency virus (HIV). A wide variety of neurological diseases are characterized by the gradual loss of specific sets of neurons. One example is Alzheimer's disease (AD). Alzheimer's disease is characterized by loss of neurons and synapses in the cerebral cortex and certain subcortical regions. This loss results in gross atrophy of the affected regions. Both amyloid plaques and neurofibrillary tangles are visible in brains of those afflicted by AD. Alzheimer's disease has been identified as a protein misfolding disease, due to the accumulation of abnormally folded A-beta and tau proteins in the brain. Plaques are made up of β-amyloid. β-amyloid is a fragment from a larger protein called amyloid precursor protein (APP). APP is critical to neuron growth, survival and post-injury repair. In AD, an unknown process causes APP to be cleaved into smaller fragments by enzymes through proteolysis. One of these fragments is fibrils of β-amyloid, which form clumps that deposit outside neurons in dense formations known as senile plaques. Plaques continue to grow into insoluble twisted fibers within the nerve cell, often called tangles. Disruption of the interaction between β-amyloid and its native receptor is therefore important in the treatment of AD. The anti-apoptotic peptidomimetics macrocycles of the invention are used, in some embodiments, in the treatment of AD and other neurological disorders associated with cell apoptosis. Such neurological disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In other or further embodiments, the anti-apoptotic peptidomimetics macrocycles of the invention are used to treat all such disorders associated with undesirable cell death.

Some examples of neurologic disorders that are treated with the peptidomimetics macrocycles described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

In another embodiment, the peptidomimetics macrocycles described herein are used to treat, prevent or diagnose inflammatory disorders. Numerous types of inflammatory disorders exist. Certain inflammatory diseases are associated with the immune system, for example, autoimmune diseases. Autoimmune diseases arise from an overactive immune response of the body against substances and tissues normally present in the body, i.e. self antigens. In other words, the immune system attacks its own cells. Autoimmune diseases are a major cause of immune-mediated diseases. Rheumatoid arthritis is an example of an autoimmune disease, in which the immune system attacks the joints, where it causes inflammation (i.e. arthritis) and destruction. It can also damage some organs, such as the lungs and skin. Rheumatoid arthritis can lead to substantial loss of functioning and mobility. Rheumatoid arthritis is diagnosed with blood tests especially the rheumatoid factor test. Some examples of autoimmune diseases that are treated with the peptidomimetics macrocycles described herein include, but are not limited to, acute disseminated encephalomyelitis (ADEM), Addison's disease, ankylosing spondylitis, antiphospholipid antibody syndrome (APS), autoimmune hemolytic anemia, autoimmune hepatitis, autoimmune inner ear disease, Bechet's disease, bullous pemphigoid, coeliac disease, Chagas disease, Churg-Strauss syndrome, chronic obstructive pulmonary disease (COPD), Crohn's disease, dermatomyositis, diabetes mellitus type 1, endometriosis, Goodpasture's syndrome, Graves' disease, Guillain-Barré syndrome (GBS), Hashimoto's disease, Hidradenitis suppurativa, idiopathic thrombocytopenic purpura, inflammatory bowel disease (IBD), interstitial cystitis, lupus erythematosus, morphea, multiple sclerosis, myasthenia gravis, narcolepsy, neuromyotonia, pemphigus vulgaris, pernicious anaemia, Polymyositis, polymyalgia rheumatica, primary biliary cirrhosis, psoriasis, rheumatoid arthritis, schizophrenia, scleroderma, Sjögren's syndrome, temporal arteritis (also known as "giant cell arteritis"), Takayasu's arteritis, Vasculitis, Vitiligo, and Wegener's granulomatosis.

Some examples of other types of inflammatory disorders that are treated with the peptidomimetics macrocycles described herein include, but are not limited to, allergy including allergic rhinitis/sinusitis, skin allergies (urticaria/hives, angioedema, atopic dermatitis), food allergies, drug allergies, insect allergies, and rare allergic disorders such as mastocytosis, asthma, arthritis including osteoarthritis, rheumatoid arthritis, and spondyloarthropathies, primary angitis of the CNS, sarcoidosis, organ transplant rejection, fibromyalgia, fibrosis, pancreatitis, and pelvic inflammatory disease.

Examples of cardiovascular disorders (e.g., inflammatory disorders) that are treated or prevented with the peptidomimetics macrocycles of the invention include, but are not limited to, aortic valve stenosis, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Synthesis of 6-Chlorotryptophan Fmoc Amino Acids

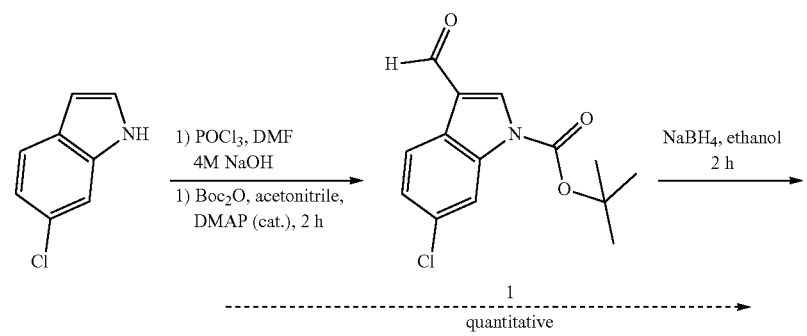

1
--------------------------------→
quantitative

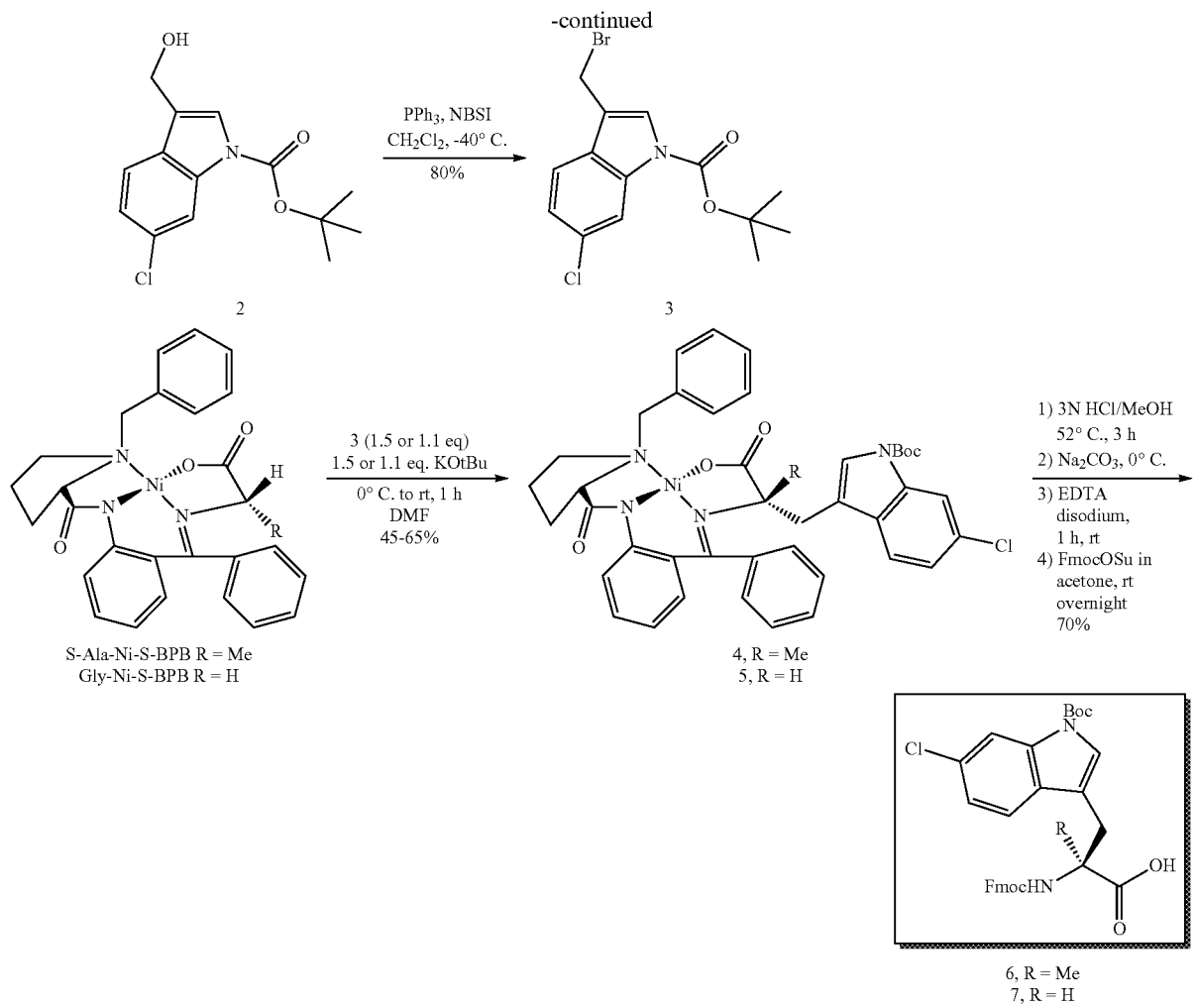

Tert-butyl 6-chloro-3-formyl-1H-indole-1-carboxylate, 1. To a stirred solution of dry DMF (12 mL) was added dropwise POCl$_3$ (3.92 mL, 43 mmol, 1.3 equiv) at 0° C. under Argon. The solution was stirred at the same temperature for 20 min before a solution of 6-chloroindole (5.0 g, 33 mmol, 1 eq.) in dry DMF (30 mL) was added dropwise. The resulting mixture was allowed to warm to room temperature and stirred for an additional 2.5 h. Water (50 mL) was added and the solution was neutralized with 4M aqueous NaOH (pH ~8). The resulting solid was filtered off, washed with water and dried under vacuum. This material was directly used in the next step without additional purification. To a stirred solution of the crude formyl indole (33 mmol, 1 eq.) in THF (150 mL) was added successively Boc$_2$O (7.91 g, 36.3 mmol, 1.1 equiv) and DMAP (0.4 g, 3.3 mmol, 0.1 equiv) at room temperature under N$_2$. The resulting mixture was stirred at room temperature for 1.5 h and the solvent was evaporated under reduced pressure. The residue was taken up in EtOAc and washed with 1N HCl, dried and concentrated to give the formyl indole 1 (9 g, 98% over 2 steps) as a white solid. $^1$H NMR (CDCl$_3$) δ: 1.70 (s, Boc, 9H); 7.35 (dd, 1H); 8.21 (m, 3H); 10.07 (s, 1H).

Tert-butyl 6-chloro-3-(hydroxymethyl)-1H-indole-1-carboxylate, 2. To a solution of compound 1 (8.86 g, 32 mmol, 1 eq.) in ethanol (150 mL) was added NaBH$_4$ (2.4 g, 63 mmol, 2 eq.). The reaction was stirred for 3 h at room temperature. The reaction mixture was concentrated and the residue was poured into diethyl ether and water. The organic layer was separated, dried over magnesium sulfate and concentrated to give a white solid (8.7 g, 98%). This material was directly used in the next step without additional purification. $^1$H NMR (CDCl$_3$) δ: 1.65 (s, Boc, 9H); 4.80 (s, 2H, CH$_2$); 7.21 (dd, 1H); 7.53 (m, 2H); 8.16 (bs, 1H).

Tert-butyl 3-(bromomethyl)-6-chloro-1H-indole-1-carboxylate, 3. To a solution of compound 2 (4.1 g, 14.6 mmol, 1 eq.) in dichloromethane (50 mL) under argon was added a solution of triphenylphosphine (4.59 g, 17.5 mmol, 1.2 eq.) in dichloromethane (50 mL) at −40° C. The reaction solution was stirred an additional 30 min at 40° C. Then NBS (3.38 g, 19 mmol, 1.3 eq.) was added. The resulting mixture was allowed to warm to room temperature and stirred overnight. Dichloromethane was evaporated, Carbon Tetrachloride (100 mL) was added and the mixture was stirred for 1 h and filtrated. The filtrate was concentrated, loaded in a silica plug and quickly eluted with 25% EtOAc in Hexanes. The solution was concentrated to give a white foam (3.84 g, 77%). $^1$H NMR (CDCl$_3$) δ: 1.66 (s, Boc, 9H); 4.63 (s, 2H, CH$_2$); 7.28 (dd, 1H); 7.57 (d, 1H); 7.64 (bs, 1H); 8.18 (bs, 1H).

αMe-6Cl-Trp(Boc)-Ni—S—BPB, 4. To S-Ala-Ni—S—BPB (2.66 g, 5.2 mmol, 1 eq.) and KO-tBu (0.87 g, 7.8 mmol, 1.5 eq.) was added 50 mL of DMF under argon. The bromide derivative compound 3 (2.68 g, 7.8 mmol, 1.5 eq.) in solution of DMF (5.0 mL) was added via syringe. The reaction mixture was stirred at ambient temperature for 1 h. The solution was then quenched with 5% aqueous acetic acid and diluted with water. The desired product was extracted in dichloromethane, dried and concentrated. The oily product 4 was purified by flash chromatography (solid loading) on normal phase using EtOAc and Hexanes as eluents to give a red solid (1.78 g, 45% yield). αMe-6Cl-Trp(Boc)-Ni—S—BPB, 4: M+H calc. 775.21, M+H obs. 775.26; $^1$H NMR (CDCl$_3$) δ: 1.23 (s, 3H, αMe); 1.56 (m, 11H, Boc+CH$_2$); 1.82-2.20 (m, 4H, 2CH$_2$); 3.03 (m, 1H, CH$_α$); 3.24 (m, 2H, CH$_2$); 3.57 and 4.29 (AB system, 2H, CH$_2$ (benzyl), J=12.8 Hz); 6.62 (d, 2H); 6.98 (d, 1H); 7.14 (m, 2H); 7.23 (m, 1H); 7.32-7.36 (m, 5H); 7.50 (m, 2H); 7.67 (bs, 1H); 7.98 (d, 2H); 8.27 (m, 2H).

Fmoc-αMe-6Cl-Trp(Boc)-OH, 6. To a solution of 3N HCl/MeOH (1/3, 15 mL) at 50° C. was added a solution of compound 4 (1.75 g, 2.3 mmol, 1 eq.) in MeOH (5 ml) dropwise. The starting material disappeared within 3-4 h. The acidic solution was then cooled to 0° C. with an ice bath and quenched with an aqueous solution of Na$_2$CO$_3$ (1.21 g, 11.5 mmol, 5 eq.). Methanol was removed and 8 more equivalents of Na$_2$CO$_3$ (1.95 g, 18.4 mmol) were added to the suspension. The Nickel scavenging EDTA disodium salt dihydrate (1.68 g, 4.5 mmol, 2 eq.) was then added and the suspension was stirred for 2 h. A solution of Fmoc-OSu (0.84 g, 2.5 mmol, 1.1 eq.) in acetone (50 mL) was added and the reaction was stirred overnight. Afterwards, the reaction was diluted with diethyl ether and 1N HCl. The organic layer was then dried over magnesium sulfate and concentrated in vacuo. The desired product 6 was purified on normal phase using acetone and dichloromethane as eluents to give a white foam (0.9 g, 70% yield). Fmoc-αMe-6Cl-Trp(Boc)-OH, 6: M+H calc. 575.19, M+H obs. 575.37; $^1$H NMR (CDCl$_3$) 1.59 (s, 9H, Boc); 1.68 (s, 3H, Me); 3.48 (bs, 2H, CH$_2$); 4.22 (m, 1H, CH); 4.39 (bs, 2H, CH$_2$); 5.47 (s, 1H, NH); 7.10 (m, 1H); 7.18 (m, 2H); 7.27 (m, 2H); 7.39 (m, 2H); 7.50 (m, 2H); 7.75 (d, 2H); 8.12 (bs, 1H).

6Cl-Trp(Boc)-Ni—S—BPB, 5. To Gly-Ni—S—BPB (4.6 g, 9.2 mmol, 1 eq.) and KO-tBu (1.14 g, 10.1 mmol, 1.1 eq.) was added 95 mL of DMF under argon. The bromide derivative compound 3 (3.5 g, 4.6 mmol, 1.1 eq.) in solution of DMF (10 mL) was added via syringe. The reaction mixture was stirred at ambient temperature for 1 h. The solution was then quenched with 5% aqueous acetic acid and diluted with water. The desired product was extracted in dichloromethane, dried and concentrated. The oily product 5 was purified by flash chromatography (solid loading) on normal phase using EtOAc and Hexanes as eluents to give a red solid (5 g, 71% yield). 6Cl-Trp(Boc)-Ni—S—BPB, 5: M+H calc. 761.20, M+H obs. 761.34; $^1$H NMR (CDCl$_3$) δ: 1.58 (m, 11H, Boc+CH$_2$); 1.84 (m, 1H); 1.96 (m, 1H); 2.24 (m, 2H, CH$_2$); 3.00 (m, 1H, CH$_α$); 3.22 (m, 2H, CH$_2$); 3.45 and 4.25 (AB system, 2H, CH$_2$ (benzyl), J=12.8 Hz); 4.27 (m, 1H, CH$_α$); 6.65 (d, 2H); 6.88 (d, 1H); 7.07 (m, 2H); 7.14 (m, 2H); 7.28 (m, 3H); 7.35-7.39 (m, 2H); 7.52 (m, 2H); 7.96 (d, 2H); 8.28 (m, 2H).

Fmoc-6Cl-Trp(Boc)-OH, 7. To a solution of 3N HCl/MeOH (1/3, 44 mL) at 50° C. was added a solution of compound 5 (5 g, 6.6 mmol, 1 eq.) in MeOH (10 ml) dropwise. The starting material disappeared within 3-4 h. The acidic solution was then cooled to 0° C. with an ice bath and quenched with an aqueous solution of Na$_2$CO$_3$ (3.48 g, 33 mmol, 5 eq.). Methanol was removed and 8 more equivalents of Na$_2$CO$_3$ (5.57 g, 52 mmol) were added to the suspension. The Nickel scavenging EDTA disodium salt dihydrate (4.89 g, 13.1 mmol, 2 eq.) and the suspension was stirred for 2 h. A solution of Fmoc-OSu (2.21 g, 6.55 mmol, 1.1 eq.) in acetone (100 mL) was added and the reaction was stirred overnight. Afterwards, the reaction was diluted with diethyl ether and 1N HCl. The organic layer was then dried over magnesium sulfate and concentrated in vacuo. The desired product 7 was purified on normal phase using acetone and dichloromethane as eluents to give a white foam (2.6 g, 69% yield). Fmoc-6Cl-Trp(Boc)-OH, 7: M+H calc. 561.17, M+H obs. 561.37; $^1$H NMR (CDCl$_3$) 1.63 (s, 9H, Boc); 3.26 (m, 2H, CH$_2$); 4.19 (m, 1H, CH); 4.39 (m, 2H, CH$_2$); 4.76 (m, 1H); 5.35 (d, 1H, NH); 7.18 (m, 2H); 7.28 (m, 2H); 7.39 (m, 3H); 7.50 (m, 2H); 7.75 (d, 2H); 8.14 (bs, 1H).

Example 2: Peptidomimetic Macrocycles of the Invention

Peptidomimetic macrocycles were synthesized, purified and analyzed as previously described and as described below (Schafmeister et al., J. Am. Chem. Soc. 122:5891-5892 (2000); Schafmeister & Verdine, J. Am. Chem. Soc. 122:5891 (2005); Walensky et al., Science 305:1466-1470 (2004); and U.S. Pat. No. 7,192,713). Peptidomimetic macrocycles were designed by replacing two or more naturally occurring amino acids with the corresponding synthetic amino acids. Substitutions were made at i and i+4, and i and i+7 positions. Peptide synthesis was performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. The N-termini of the synthetic peptides were acetylated, while the C-termini were amidated.

Purification of cross-linked compounds was achieved by high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

Table 4 shows a list of peptidomimetic macrocycles of the invention prepared.

TABLE 4

| SP | Seq | Exact Mass | M + 2 | Observed mass (m/e) |
|---|---|---|---|---|
| SP-1 | Ac-LSQETF$r8DLWKLL$EN-NH2 | 2068.13 | 1035.07 | 1035.36 |
| SP-2 | Ac-LSQETF$r8NLWKLL$QN-NH2 | 2066.16 | 1034.08 | 1034.31 |

TABLE 4-continued

| SP | Seq | Exact Mass | M + 2 | Observed mass (m/e) |
|---|---|---|---|---|
| SP-3 | Ac-LSQQTF$r8NLWRLL$QN-NH2 | 2093.18 | 1047.59 | 1047.73 |
| SP-4 | Ac-QSQQTF$r8NLWKLL$QN-NH2 | 2080.15 | 1041.08 | 1041.31 |
| SP-5 | Ac-QSQQTF$r8NLWRLL$QN-NH2 | 2108.15 | 1055.08 | 1055.32 |
| SP-6 | Ac-QSQQTA$r8NLWRLL$QN-NH2 | 2032.12 | 1017.06 | 1017.24 |
| SP-7 | Ac-QAibQQTF$r8NLWRLL$QN-NH2 | 2106.17 | 1054.09 | 1054.34 |
| SP-8 | Ac-QSQQTFSNLWRLLPQN-NH2 | 2000.02 | 1001.01 | 1001.26 |
| SP-9 | Ac-QSQQTF$/r8NLWRLL$/QN-NH2 | 2136.18 | 1069.09 | 1069.37 |
| SP-10 | Ac-QSQAibTF$r8NLWRLL$QN-NH2 | 2065.15 | 1033.58 | 1033.71 |
| SP-11 | Ac-QSQQTF$r8NLWRLL$AN-NH2 | 2051.13 | 1026.57 | 1026.70 |
| SP-12 | Ac-ASQQTF$r8NLWRLL$QN-NH2 | 2051.13 | 1026.57 | 1026.90 |
| SP-13 | Ac-QSQQTF$r8ALWRLL$QN-NH2 | 2065.15 | 1033.58 | 1033.41 |
| SP-14 | Ac-QSQETF$r8NLWRLL$QN-NH2 | 2109.14 | 1055.57 | 1055.70 |
| SP-15 | Ac-RSQQTF$r8NLWRLL$QN-NH2 | 2136.20 | 1069.10 | 1069.17 |
| SP-16 | Ac-RSQQTF$r8NLWRLL$EN-NH2 | 2137.18 | 1069.59 | 1069.75 |
| SP-17 | Ac-LSQETFSDLWKLLPEN-NH2 | 1959.99 | 981.00 | 981.24 |
| SP-18 | Ac-QSQ$TFS$LWRLLPQN-NH2 | 2008.09 | 1005.05 | 1004.97 |
| SP-19 | Ac-QSQQ$FSN$WRLLPQN-NH2 | 2036.06 | 1019.03 | 1018.86 |
| SP-20 | Ac-QSQQT$SNL$RLLPQN-NH2 | 1917.04 | 959.52 | 959.32 |
| SP-21 | Ac-QSQQTF$NLW$LLPQN-NH2 | 2007.06 | 1004.53 | 1004.97 |
| SP-22 | Ac-RTQATF$r8NQWAibANle$TNAibTR-NH2 | 2310.26 | 1156.13 | 1156.52 |
| SP-23 | Ac-QSQQTF$r8NLWRLL$RN-NH2 | 2136.20 | 1069.10 | 1068.94 |
| SP-24 | Ac-QSQRTF$r8NLWRLL$QN-NH2 | 2136.20 | 1069.10 | 1068.94 |
| SP-25 | Ac-QSQQTF$r8NNleWRLL$QN-NH2 | 2108.15 | 1055.08 | 1055.44 |
| SP-26 | Ac-QSQQTF$r8NLWRNleL$QN-NH2 | 2108.15 | 1055.08 | 1055.84 |
| SP-27 | Ac-QSQQTF$r8NLWRLNle$QN-NH2 | 2108.15 | 1055.08 | 1055.12 |
| SP-28 | Ac-QSQQTY$r8NLWRLL$QN-NH2 | 2124.15 | 1063.08 | 1062.92 |
| SP-29 | Ac-RAibQQTF$r8NLWRLL$QN-NH2 | 2134.22 | 1068.11 | 1068.65 |
| SP-30 | Ac-MPRFMDYWEGLN-NH2 | 1598.70 | 800.35 | 800.45 |
| SP-31 | Ac-RSQQRF$r8NLWRLL$QN-NH2 | 2191.25 | 1096.63 | 1096.83 |
| SP-32 | Ac-QSQQRF$r8NLWRLL$QN-NH2 | 2163.21 | 1082.61 | 1082.87 |
| SP-33 | Ac-RAibQQRF$r8NLWRLL$QN-NH2 | 2189.27 | 1095.64 | 1096.37 |
| SP-34 | Ac-RSQQRF$r8NFWRLL$QN-NH2 | 2225.23 | 1113.62 | 1114.37 |
| SP-35 | Ac-RSQQRF$r8NYWRLL$QN-NH2 | 2241.23 | 1121.62 | 1122.37 |
| SP-36 | Ac-RSQQTF$r8NLWQLL$QN-NH2 | 2108.15 | 1055.08 | 1055.29 |
| SP-37 | Ac-QSQQTF$r8NLWQAmlL$QN-NH2 | 2094.13 | 1048.07 | 1048.32 |
| SP-38 | Ac-QSQQTF$r8NAmIWRLL$QN-NH2 | 2122.17 | 1062.09 | 1062.35 |
| SP-39 | Ac-NlePRF$r8DYWEGL$QN-NH2 | 1869.98 | 935.99 | 936.20 |
| SP-40 | Ac-NlePRF$r8NYWRLL$QN-NH2 | 1952.12 | 977.06 | 977.35 |

TABLE 4-continued

| SP | Seq | Exact Mass | M + 2 | Observed mass (m/e) |
|---|---|---|---|---|
| SP-41 | Ac-RF$r8NLWRLL$Q-NH2 | 1577.96 | 789.98 | 790.18 |
| SP-42 | Ac-QSQQTF$r8N2ffWRLL$QN-NH2 | 2160.13 | 1081.07 | 1081.40 |
| SP-43 | Ac-QSQQTF$r8N3ffWRLL$QN-NH2 | 2160.13 | 1081.07 | 1081.34 |
| SP-44 | Ac-QSQQTF#r8NLWRLL#QN-NH2 | 2080.12 | 1041.06 | 1041.34 |
| SP-45 | Ac-RSQQTA$r8NLWRLL$QN-NH2 | 2060.16 | 1031.08 | 1031.38 |
| SP-46 | Ac-QSQQTF%r8NLWRLL%QN-NH2 | 2110.17 | 1056.09 | 1056.55 |
| SP-47 | HepQSQ$TFSNLWRLLPQN-NH2 | 2051.10 | 1026.55 | 1026.82 |
| SP-48 | HepQSQ$TF$r8NLWRLL$QN-NH2 | 2159.23 | 1080.62 | 1080.89 |
| SP-49 | Ac-QSQQTF$r8NL6cIWRLL$QN-NH2 | 2142.11 | 1072.06 | 1072.35 |
| SP-50 | Ac-QSQQTF$r8NLMe6clwRLL$QN-NH2 | 2156.13 | 1079.07 | 1079.27 |
| SP-51 | Ac-LTFEHYWAQLTS-NH2 | 1535.74 | 768.87 | 768.91 |
| SP-52 | Ac-LTF$HYW$QLTS-NH2 | 1585.83 | 793.92 | 794.17 |
| SP-53 | Ac-LTFE$YWA$LTS-NH2 | 1520.79 | 761.40 | 761.67 |
| SP-54 | Ac-LTF$zr8HYWAQL$zS-NH2 | 1597.87 | 799.94 | 800.06 |
| SP-55 | Ac-LTF$r8HYWRQL$S-NH2 | 1682.93 | 842.47 | 842.72 |
| SP-56 | Ac-QS$QTFStNLWRLL$s8QN-NH2 | 2145.21 | 1073.61 | 1073.90 |
| SP-57 | Ac-QSQQTASNLWRLLPQN-NH2 | 1923.99 | 963.00 | 963.26 |
| SP-58 | Ac-QSQQTA$/r8NLWRLL$/QN-NH2 | 2060.15 | 1031.08 | 1031.24 |
| SP-59 | Ac-ASQQTF$/r8NLWRLL$/QN-NH2 | 2079.16 | 1040.58 | 1040.89 |
| SP-60 | Ac-$SQQ$FSNLWRLLAibQN-NH2 | 2009.09 | 1005.55 | 1005.86 |
| SP-61 | Ac-QS$QTF$NLWRLLAibQN-NH2 | 2023.10 | 1012.55 | 1012.79 |
| SP-62 | Ac-QSQQ$FSN$WRLLAibQN-NH2 | 2024.06 | 1013.03 | 1013.31 |
| SP-63 | Ac-QSQQTF$NLW$LLAibQN-NH2 | 1995.06 | 998.53 | 998.87 |
| SP-64 | Ac-QSQQTFS$LWR$LAibQN-NH2 | 2011.06 | 1006.53 | 1006.83 |
| SP-65 | Ac-QSQQTFSNLW$LLA$N-NH2 | 1940.02 | 971.01 | 971.29 |
| SP-66 | Ac-$/SQQ$/FSNLWRLLAibQN-NH2 | 2037.12 | 1019.56 | 1019.78 |
| SP-67 | Ac-QS$/QTF$/NLWRLLAibQN-NH2 | 2051.13 | 1026.57 | 1026.90 |
| SP-68 | Ac-QSQQ$/FSN$/WRLLAibQN-NH2 | 2052.09 | 1027.05 | 1027.36 |
| SP-69 | Ac-QSQQTF$/NLW$/LLAibQN-NH2 | 2023.09 | 1012.55 | 1013.82 |
| SP-70 | Ac-QS$TFS$LWRLLAibQN-NH2 | 1996.09 | 999.05 | 999.39 |
| SP-71 | Ac-QSQ$/TFS$/LWRLLAibQN-NH2 | 2024.12 | 1013.06 | 1013.37 |
| SP-72 | Ac-QS$/QTFSt//NLWRLL$/s8QN-NH2 | 2201.27 | 1101.64 | 1102.00 |
| SP-73 | Ac-$r8SQQTFS$LWRLLAibQN-NH2 | 2038.14 | 1020.07 | 1020.23 |
| SP-74 | Ac-QS$r8TFSNLW$LLAibQN-NH2 | 1996.08 | 999.04 | 999.32 |
| SP-75 | Ac-QSQQTFS$r8LWRLLA$N-NH2 | 2024.12 | 1013.06 | 1013.37 |
| SP-76 | Ac-QS$r5QTFStNLW$LLAibQN-NH2 | 2032.12 | 1017.06 | 1017.39 |
| SP-77 | Ac-$/r8SQQTFS$/LWRLLAibQN-NH2 | 2066.17 | 1034.09 | 1034.80 |
| SP-78 | Ac-QSQ$/r8TFSNLW$/LLAibQN-NH2 | 2024.11 | 1013.06 | 1014.34 |

TABLE 4-continued

| SP | Seq | Exact Mass | M + 2 | Observed mass (m/e) |
|---|---|---|---|---|
| SP-79 | Ac-QSQQTFS$/r8LWRLLA$/N-NH2 | 2052.15 | 1027.08 | 1027.16 |
| SP-80 | Ac-QS$/r5QTFSt//NLW$/LLAibQN-NH2 | 2088.18 | 1045.09 | 1047.10 |
| SP-81 | Ac-QSQQTFSNLWRLLAibQN-NH2 | 1988.02 | 995.01 | 995.31 |
| SP-82 | Hep/QSQ$/TF$/r8NLWRLL$/QN-NH2 | 2215.29 | 1108.65 | 1108.93 |
| SP-83 | Ac-ASQQTF$r8NLRWLL$QN-NH2 | 2051.13 | 1026.57 | 1026.90 |
| SP-84 | Ac-QSQQTF$/r8NLWRLL$/Q-NH2 | 2022.14 | 1012.07 | 1012.66 |
| SP-85 | Ac-QSQQTF$r8NLWRLL$Q-NH2 | 1994.11 | 998.06 | 998.42 |
| SP-86 | Ac-AAARAA$r8AAARAA$AA-NH2 | 1515.90 | 758.95 | 759.21 |
| SP-87 | Ac-LTFEHYWAQLTSA-NH2 | 1606.78 | 804.39 | 804.59 |
| SP-88 | Ac-LTF$r8HYWAQL$SA-NH2 | 1668.90 | 835.45 | 835.67 |
| SP-89 | Ac-ASQQTFSNLWRLLPQN-NH2 | 1943.00 | 972.50 | 973.27 |
| SP-90 | Ac-QS$QTFStNLW$r5LLAibQN-NH2 | 2032.12 | 1017.06 | 1017.30 |
| SP-91 | Ac-QSQQTFAibNLWRLLAibQN-NH2 | 1986.04 | 994.02 | 994.19 |
| SP-92 | Ac-QSQQTFNleNLWRLLNleQN-NH2 | 2042.11 | 1022.06 | 1022.23 |
| SP-93 | Ac-QSQQTF$/r8NLWRLLAibQN-NH2 | 2082.14 | 1042.07 | 1042.23 |
| SP-94 | Ac-QSQQTF$/r8NLWRLLNleQN-NH2 | 2110.17 | 1056.09 | 1056.29 |
| SP-95 | Ac-QSQQTFAibNLWRLL$/QN-NH2 | 2040.09 | 1021.05 | 1021.25 |
| SP-96 | Ac-QSQQTFNleNLWRLL$/QN-NH2 | 2068.12 | 1035.06 | 1035.31 |
| SP-97 | Ac-QSQQTF%r8NL6cIWRNleL%QN-NH2 | 2144.13 | 1073.07 | 1073.32 |
| SP-98 | Ac-QSQQTF%r8NLMe6cIWRLL%QN-NH2 | 2158.15 | 1080.08 | 1080.31 |
| SP-101 | Ac-FNle$YWE$L-NH2 | 1160.63 | — | 1161.70 |
| SP-102 | Ac-F$r8AYWELL$A-NH2 | 1344.75 | — | 1345.90 |
| SP-103 | Ac-F$r8AYWQLL$A-NH2 | 1343.76 | — | 1344.83 |
| SP-104 | Ac-NlePRF$r8NYWELL$QN-NH2 | 1925.06 | 963.53 | 963.69 |
| SP-105 | Ac-NlePRF$r8DYWRLL$QN-NH2 | 1953.10 | 977.55 | 977.68 |
| SP-106 | Ac-NlePRF$r8NYWRLL$Q-NH2 | 1838.07 | 920.04 | 920.18 |
| SP-107 | Ac-NlePRF$r8NYWRLL$-NH2 | 1710.01 | 856.01 | 856.13 |
| SP-108 | Ac-QSQQTF$r8DLWRLL$QN-NH2 | 2109.14 | 1055.57 | 1055.64 |
| SP-109 | Ac-QSQQTF$r8NLWRLL$EN-NH2 | 2109.14 | 1055.57 | 1055.70 |
| SP-110 | Ac-QSQQTF$r8NLWRLL$QD-NH2 | 2109.14 | 1055.57 | 1055.64 |
| SP-111 | Ac-QSQQTF$r8NLWRLL$S-NH2 | 1953.08 | 977.54 | 977.60 |
| SP-112 | Ac-ESQQTF$r8NLWRLL$QN-NH2 | 2109.14 | 1055.57 | 1055.70 |
| SP-113 | Ac-LTF$r8NLWRNleL$Q-NH2 | 1635.99 | 819.00 | 819.10 |
| SP-114 | Ac-LRF$r8NLWRNleL$Q-NH2 | 1691.04 | 846.52 | 846.68 |
| SP-115 | Ac-QSQQTF$r8NWWRNleL$QN-NH2 | 2181.15 | 1091.58 | 1091.64 |
| SP-116 | Ac-QSQQTF$r8NLWRNleL$Q-NH2 | 1994.11 | 998.06 | 998.07 |
| SP-117 | Ac-QTF$r8NLWRNleL$QN-NH2 | 1765.00 | 883.50 | 883.59 |
| SP-118 | Ac-NlePRF$r8NWWRLL$QN-NH2 | 1975.13 | 988.57 | 988.75 |

TABLE 4-continued

| SP | Seq | Exact Mass | M + 2 | Observed mass (m/e) |
|---|---|---|---|---|
| SP-119 | Ac-NlePRF$r8NWWRLL$A-NH2 | 1804.07 | 903.04 | 903.08 |
| SP-120 | Ac-TSFAEYWNLLSP-NH2 | 1467.70 | 734.85 | 734.90 |
| SP-121 | Ac-QTF$r8HWWSQL$S-NH2 | 1651.85 | 826.93 | 827.12 |
| SP-122 | Ac-FM$YWE$L-NH2 | 1178.58 | — | 1179.64 |
| SP-123 | Ac-QTFEHWWSQLLS-NH2 | 1601.76 | 801.88 | 801.94 |
| SP-124 | Ac-QSQQTF$r8NLAmwRLNle$QN-NH2 | 2122.17 | 1062.09 | 1062.24 |
| SP-125 | Ac-FMAibY6cIWEAc3cL-NH2 | 1130.47 | — | 1131.53 |
| SP-126 | Ac-FNle$Y6cIWE$L-NH2 | 1194.59 | — | 1195.64 |
| SP-127 | Ac-F$zr8AY6cIWEAc3cL$z-NH2 | 1277.63 | 639.82 | 1278.71 |
| SP-128 | Ac-F$r8AY6cIWEAc3cL$A-NH2 | 1348.66 | — | 1350.72 |
| SP-129 | Ac-NlePRF$r8NY6cIWRLL$QN-NH2 | 1986.08 | 994.04 | 994.64 |
| SP-130 | Ac-AF$r8AAWALA$A-NH2 | 1223.71 | — | 1224.71 |
| SP-131 | Ac-TF$r8AAWRLA$Q-NH2 | 1395.80 | 698.90 | 399.04 |
| SP-132 | Pr-TF$r8AAWRLA$Q-NH2 | 1409.82 | 705.91 | 706.04 |
| SP-133 | Ac-QSQQTF%r8NLWRNleL%QN-NH2 | 2110.17 | 1056.09 | 1056.22 |
| SP-134 | Ac-LTF%r8HYWAQL%SA-NH2 | 1670.92 | 836.46 | 836.58 |
| SP-135 | Ac-NlePRF%r8NYWRLL%QN-NH2 | 1954.13 | 978.07 | 978.19 |
| SP-136 | Ac-NlePRF%r8NY6cIWRLL%QN-NH2 | 1988.09 | 995.05 | 995.68 |
| SP-137 | Ac-LTF%r8HY6cIWAQL%S-NH2 | 1633.84 | 817.92 | 817.93 |
| SP-138 | Ac-QS%QTF%StNLWRLL%s8QN-NH2 | 2149.24 | 1075.62 | 1075.65 |
| SP-139 | Ac-LTF%r8HY6cIWRQL%S-NH2 | 1718.91 | 860.46 | 860.54 |
| SP-140 | Ac-QSQQTF%r8NL6cIWRLL%QN-NH2 | 2144.13 | 1073.07 | 1073.64 |
| SP-141 | Ac-%r8SQQTFS%LWRLLAibQN-NH2 | 2040.15 | 1021.08 | 1021.13 |
| SP-142 | Ac-LTF%r8HYWAQL%S-NH2 | 1599.88 | 800.94 | 801.09 |
| SP-143 | Ac-TSF%r8QYWNLL%P-NH2 | 1602.88 | 802.44 | 802.58 |
| SP-147 | Ac-LTFEHYWAQLTS-NH2 | 1535.74 | 768.87 | 769.5 |
| SP-152 | Ac-F$er8AY6cIWEAc3cL$e-NH2 | 1277.63 | 639.82 | 1278.71 |
| SP-153 | Ac-AF$r8AAWALA$A-NH2 | 1277.63 | 639.82 | 1277.84 |
| SP-154 | Ac-TF$r8AAWRLA$Q-NH2 | 1395.80 | 698.90 | 699.04 |
| SP-155 | Pr-TF$r8AAWRLA$Q-NH2 | 1409.82 | 705.91 | 706.04 |
| SP-156 | Ac-LTF$er8HYWAQL$eS-NH2 | 1597.87 | 799.94 | 800.44 |
| SP-159 | Ac-CCPGCCBaQSQQTF$r8NLWRLL$QN-NH2 | 2745.30 | 1373.65 | 1372.99 |
| SP-160 | Ac-CCPGCCBaQSQQTA$r8NLWRLL$QN-NH2 | 2669.27 | 1335.64 | 1336.09 |
| SP-161 | Ac-CCPGCCBaNlePRF$r8NYWRLL$QN-NH2 | 2589.26 | 1295.63 | 1296.2 |
| SP-162 | Ac-LTF$/r8HYWAQL$/S-NH2 | 1625.90 | 813.95 | 814.18 |
| SP-163 | Ac-F%r8HY6cIWRAc3cL%-NH2 | 1372.72 | 687.36 | 687.59 |
| SP-164 | Ac-QTF%r8HWWSQL%S-NH2 | 1653.87 | 827.94 | 827.94 |

TABLE 4-continued

| SP | Seq | Exact Mass | M + 2 | Observed mass (m/e) |
|---|---|---|---|---|
| SP-165 | Ac-LTA$r8HYWRQL$S-NH2 | 1606.90 | 804.45 | 804.66 |
| SP-166 | Ac-Q$r8QQTFSN$WRLLAibQN-NH2 | 2080.12 | 1041.06 | 1041.61 |
| SP-167 | Ac-QSQQ$r8FSNLWR$LAibQN-NH2 | 2066.11 | 1034.06 | 1034.58 |
| SP-168 | Ac-F$r8AYWEAc3cL$A-NH2 | 1314.70 | 658.35 | 1315.88 |
| SP-169 | Ac-F$r8AYWEAc3cL$S-NH2 | 1330.70 | 666.35 | 1331.87 |
| SP-170 | Ac-F$r8AYWEAc3cL$Q-NH2 | 1371.72 | 686.86 | 1372.72 |
| SP-171 | Ac-F$r8AYWEAibL$S-NH2 | 1332.71 | 667.36 | 1334.83 |
| SP-172 | Ac-F$r8AYWEAL$S-NH2 | 1318.70 | 660.35 | 1319.73 |
| SP-173 | Ac-F$r8AYWEQL$S-NH2 | 1375.72 | 688.86 | 1377.53 |
| SP-174 | Ac-F$r8HYWEQL$S-NH2 | 1441.74 | 721.87 | 1443.48 |
| SP-175 | Ac-F$r8HYWAQL$S-NH2 | 1383.73 | 692.87 | 1385.38 |
| SP-176 | Ac-F$r8HYWAAc3cL$S-NH2 | 1338.71 | 670.36 | 1340.82 |
| SP-177 | Ac-F$r8HYWRAc3cL$S-NH2 | 1423.78 | 712.89 | 713.04 |
| SP-178 | Ac-F$r8AYWEAc3cL#A-NH2 | 1300.69 | 651.35 | 1302.78 |
| SP-179 | Ac-NlePTF%r8NYWRLL%QN-NH2 | 1899.08 | 950.54 | 950.56 |
| SP-180 | Ac-TF$r8AAWRAL$Q-NH2 | 1395.80 | 698.90 | 699.13 |
| SP-181 | Ac-TSF%r8HYWAQL%S-NH2 | 1573.83 | 787.92 | 787.98 |
| SP-184 | Ac-F%r8AY6cIWEAc3cL%A-NH2 | 1350.68 | 676.34 | 676.91 |
| SP-185 | Ac-LTF$r8HYWAQI$S-NH2 | 1597.87 | 799.94 | 800.07 |
| SP-186 | Ac-LTF$r8HYWAQNle$S-NH2 | 1597.87 | 799.94 | 800.07 |
| SP-187 | Ac-LTF$r8HYWAQL$A-NH2 | 1581.87 | 791.94 | 792.45 |
| SP-188 | Ac-LTF$r8HYWAQL$Abu-NH2 | 1595.89 | 798.95 | 799.03 |
| SP-189 | Ac-LTF$r8HYWAbuQL$S-NH2 | 1611.88 | 806.94 | 807.47 |
| SP-190 | Ac-LTF$er8AYWAQL$eS-NH2 | 1531.84 | 766.92 | 766.96 |
| SP-191 | Ac-LAF$r8HYWAQL$S-NH2 | 1567.86 | 784.93 | 785.49 |
| SP-192 | Ac-LAF$r8AYWAQL$S-NH2 | 1501.83 | 751.92 | 752.01 |
| SP-193 | Ac-LTF$er8AYWAQL$eA-NH2 | 1515.85 | 758.93 | 758.97 |
| SP-194 | Ac-LAF$r8AYWAQL$A-NH2 | 1485.84 | 743.92 | 744.05 |
| SP-195 | Ac-LTF$r8NLWANleL$Q-NH2 | 1550.92 | 776.46 | 776.61 |
| SP-196 | Ac-LTF$r8NLWANleL$A-NH2 | 1493.90 | 747.95 | 1495.6 |
| SP-197 | Ac-LTF$r8ALWANleL$Q-NH2 | 1507.92 | 754.96 | 755 |
| SP-198 | Ac-LAF$r8NLWANleL$Q-NH2 | 1520.91 | 761.46 | 761.96 |
| SP-199 | Ac-LAF$r8ALWANleL$A-NH2 | 1420.89 | 711.45 | 1421.74 |
| SP-200 | Ac-A$r8AYWEAc3cL$A-NH2 | 1238.67 | 620.34 | 1239.65 |
| SP-201 | Ac-F$r8AYWEAc3cL$AA-NH2 | 1385.74 | 693.87 | 1386.64 |
| SP-202 | Ac-F$r8AYWEAc3cL$Abu-NH2 | 1328.72 | 665.36 | 1330.17 |
| SP-203 | Ac-F$r8AYWEAc3cL$Nle-NH2 | 1356.75 | 679.38 | 1358.22 |
| SP-204 | Ac-F$r5AYWEAc3cL$s8A-NH2 | 1314.70 | 658.35 | 1315.51 |

TABLE 4-continued

| SP | Seq | Exact Mass | M + 2 | Observed mass (m/e) |
|---|---|---|---|---|
| SP-205 | Ac-F$AYWEAc3cL$r8A-NH2 | 1314.70 | 658.35 | 1315.66 |
| SP-206 | Ac-F$r8AYWEAc3cI$A-NH2 | 1314.70 | 658.35 | 1316.18 |
| SP-207 | Ac-F$r8AYWEAc3cNle$A-NH2 | 1314.70 | 658.35 | 1315.66 |
| SP-208 | Ac-F$r8AYWEAmlL$A-NH2 | 1358.76 | 680.38 | 1360.21 |
| SP-209 | Ac-F$r8AYWENleL$A-NH2 | 1344.75 | 673.38 | 1345.71 |
| SP-210 | Ac-F$r8AYWQAc3cL$A-NH2 | 1313.72 | 657.86 | 1314.7 |
| SP-211 | Ac-F$r8AYWAAc3cL$A-NH2 | 1256.70 | 629.35 | 1257.56 |
| SP-212 | Ac-F$r8AYWAbuAc3cL$A-NH2 | 1270.71 | 636.36 | 1272.14 |
| SP-213 | Ac-F$r8AYWNleAc3cL$A-NH2 | 1298.74 | 650.37 | 1299.67 |
| SP-214 | Ac-F$r8AbuYWEAc3cL$A-NH2 | 1328.72 | 665.36 | 1329.65 |
| SP-215 | Ac-F$r8NleYWEAc3cL$A-NH2 | 1356.75 | 679.38 | 1358.66 |
| SP-216 | 5-FAM-BaLTFEHYWAQLTS-NH2 | 1922.82 | 962.41 | 962.87 |
| SP-217 | 5-FAM-BaLTF%r8HYWAQL%S-NH2 | 1986.96 | 994.48 | 994.97 |
| SP-218 | Ac-LTF$r8HYWAQhL$S-NH2 | 1611.88 | 806.94 | 807 |
| SP-219 | Ac-LTF$r8HYWAQTle$S-NH2 | 1597.87 | 799.94 | 799.97 |
| SP-220 | Ac-LTF$r8HYWAQAdm$S-NH2 | 1675.91 | 838.96 | 839.09 |
| SP-221 | Ac-LTF$r8HYWAQhCha$S-NH2 | 1651.91 | 826.96 | 826.98 |
| SP-222 | Ac-LTF$r8HYWAQCha$S-NH2 | 1637.90 | 819.95 | 820.02 |
| SP-223 | Ac-LTF$r8HYWAc6cQL$S-NH2 | 1651.91 | 826.96 | 826.98 |
| SP-224 | Ac-LTF$r8HYWAc5cQL$S-NH2 | 1637.90 | 819.95 | 820.02 |
| SP-225 | Ac-LThF$r8HYWAQL$S-NH2 | 1611.88 | 806.94 | 807 |
| SP-226 | Ac-LTIgl$r8HYWAQL$S-NH2 | 1625.90 | 813.95 | 812.99 |
| SP-227 | Ac-LTF$r8HYWAQChg$S-NH2 | 1623.88 | 812.94 | 812.99 |
| SP-228 | Ac-LTF$r8HYWAQF$S-NH2 | 1631.85 | 816.93 | 816.99 |
| SP-229 | Ac-LTF$r8HYWAQIgl$S-NH2 | 1659.88 | 830.94 | 829.94 |
| SP-230 | Ac-LTF$r8HYWAQCba$S-NH2 | 1609.87 | 805.94 | 805.96 |
| SP-231 | Ac-LTF$r8HYWAQCpg$S-NH2 | 1609.87 | 805.94 | 805.96 |
| SP-232 | Ac-LTF$r8HhYWAQL$S-NH2 | 1611.88 | 806.94 | 807 |
| SP-233 | Ac-F$r8AYWEAc3chL$A-NH2 | 1328.72 | 665.36 | 665.43 |
| SP-234 | Ac-F$r8AYWEAc3cTle$A-NH2 | 1314.70 | 658.35 | 1315.62 |
| SP-235 | Ac-F$r8AYWEAc3cAdm$A-NH2 | 1392.75 | 697.38 | 697.47 |
| SP-236 | Ac-F$r8AYWEAc3chCha$A-NH2 | 1368.75 | 685.38 | 685.34 |
| SP-237 | Ac-F$r8AYWEAc3cCha$A-NH2 | 1354.73 | 678.37 | 678.38 |
| SP-238 | Ac-F$r8AYWEAc6cL$A-NH2 | 1356.75 | 679.38 | 679.42 |
| SP-239 | Ac-F$r8AYWEAc5cL$A-NH2 | 1342.73 | 672.37 | 672.46 |
| SP-240 | Ac-hF$r8AYWEAc3cL$A-NH2 | 1328.72 | 665.36 | 665.43 |
| SP-241 | Ac-Igl$r8AYWEAc3cL$A-NH2 | 1342.73 | 672.37 | 671.5 |
| SP-243 | Ac-F$r8AYWEAc3cF$A-NH2 | 1348.69 | 675.35 | 675.35 |

TABLE 4-continued

| SP | Seq | Exact Mass | M + 2 | Observed mass (m/e) |
|---|---|---|---|---|
| SP-244 | Ac-F$r8AYWEAc3cIgl$A-NH2 | 1376.72 | 689.36 | 688.37 |
| SP-245 | Ac-F$r8AYWEAc3cCba$A-NH2 | 1326.70 | 664.35 | 664.47 |
| SP-246 | Ac-F$r8AYWEAc3cCpg$A-NH2 | 1326.70 | 664.35 | 664.39 |
| SP-247 | Ac-F$r8AhYWEAc3cL$A-NH2 | 1328.72 | 665.36 | 665.43 |
| SP-248 | Ac-F$r8AYWEAc3cL$Q-NH2 | 1371.72 | 686.86 | 1372.87 |
| SP-249 | Ac-F$r8AYWEAibL$A-NH2 | 1316.72 | 659.36 | 1318.18 |
| SP-250 | Ac-F$r8AYWEAL$A-NH2 | 1302.70 | 652.35 | 1303.75 |
| SP-251 | Ac-LAF$r8AYWAAL$A-NH2 | 1428.82 | 715.41 | 715.49 |
| SP-252 | Ac-LTF$r8HYWAAc3cL$S-NH2 | 1552.84 | 777.42 | 777.5 |
| SP-253 | Ac-NleTF$r8HYWAQL$S-NH2 | 1597.87 | 799.94 | 800.04 |
| SP-254 | Ac-VTF$r8HYWAQL$S-NH2 | 1583.85 | 792.93 | 793.04 |
| SP-255 | Ac-FTF$r8HYWAQL$S-NH2 | 1631.85 | 816.93 | 817.02 |
| SP-256 | Ac-WTF$r8HYWAQL$S-NH2 | 1670.86 | 836.43 | 836.85 |
| SP-257 | Ac-RTF$r8HYWAQL$S-NH2 | 1640.88 | 821.44 | 821.9 |
| SP-258 | Ac-KTF$r8HYWAQL$S-NH2 | 1612.88 | 807.44 | 807.91 |
| SP-259 | Ac-LNleF$r8HYWAQL$S-NH2 | 1609.90 | 805.95 | 806.43 |
| SP-260 | Ac-LVF$r8HYWAQL$S-NH2 | 1595.89 | 798.95 | 798.93 |
| SP-261 | Ac-LFF$r8HYWAQL$S-NH2 | 1643.89 | 822.95 | 823.38 |
| SP-262 | Ac-LWF$r8HYWAQL$S-NH2 | 1682.90 | 842.45 | 842.55 |
| SP-263 | Ac-LRF$r8HYWAQL$S-NH2 | 1652.92 | 827.46 | 827.52 |
| SP-264 | Ac-LKF$r8HYWAQL$S-NH2 | 1624.91 | 813.46 | 813.51 |
| SP-265 | Ac-LTF$r8NleYWAQL$S-NH2 | 1573.89 | 787.95 | 788.05 |
| SP-266 | Ac-LTF$r8VYWAQL$S-NH2 | 1559.88 | 780.94 | 780.98 |
| SP-267 | Ac-LTF$r8FYWAQL$S-NH2 | 1607.88 | 804.94 | 805.32 |
| SP-268 | Ac-LTF$r8WYWAQL$S-NH2 | 1646.89 | 824.45 | 824.86 |
| SP-269 | Ac-LTF$r8RYWAQL$S-NH2 | 1616.91 | 809.46 | 809.51 |
| SP-270 | Ac-LTF$r8KYWAQL$S-NH2 | 1588.90 | 795.45 | 795.48 |
| SP-271 | Ac-LTF$r8HNleWAQL$S-NH2 | 1547.89 | 774.95 | 774.98 |
| SP-272 | Ac-LTF$r8HVWAQL$S-NH2 | 1533.87 | 767.94 | 767.95 |
| SP-273 | Ac-LTF$r8HFWAQL$S-NH2 | 1581.87 | 791.94 | 792.3 |
| SP-274 | Ac-LTF$r8HWWAQL$S-NH2 | 1620.88 | 811.44 | 811.54 |
| SP-275 | Ac-LTF$r8HRWAQL$S-NH2 | 1590.90 | 796.45 | 796.52 |
| SP-276 | Ac-LTF$r8HKWAQL$S-NH2 | 1562.90 | 782.45 | 782.53 |
| SP-277 | Ac-LTF$r8HYWNleQL$S-NH2 | 1639.91 | 820.96 | 820.98 |
| SP-278 | Ac-LTF$r8HYWVQL$S-NH2 | 1625.90 | 813.95 | 814.03 |
| SP-279 | Ac-LTF$r8HYWFQL$S-NH2 | 1673.90 | 837.95 | 838.03 |
| SP-280 | Ac-LTF$r8HYWWQL$S-NH2 | 1712.91 | 857.46 | 857.5 |
| SP-281 | Ac-LTF$r8HYWKQL$S-NH2 | 1654.92 | 828.46 | 828.49 |

TABLE 4-continued

| SP | Seq | Exact Mass | M + 2 | Observed mass (m/e) |
|---|---|---|---|---|
| SP-282 | Ac-LTF$r8HYWANleL$S-NH2 | 1582.89 | 792.45 | 792.52 |
| SP-283 | Ac-LTF$r8HYWAVL$S-NH2 | 1568.88 | 785.44 | 785.49 |
| SP-284 | Ac-LTF$r8HYWAFL$S-NH2 | 1616.88 | 809.44 | 809.47 |
| SP-285 | Ac-LTF$r8HYWAWL$S-NH2 | 1655.89 | 828.95 | 829 |
| SP-286 | Ac-LTF$r8HYWARL$S-NH2 | 1625.91 | 813.96 | 813.98 |
| SP-287 | Ac-LTF$r8HYWAQL$Nle-NH2 | 1623.92 | 812.96 | 813.39 |
| SP-288 | Ac-LTF$r8HYWAQL$V-NH2 | 1609.90 | 805.95 | 805.99 |
| SP-289 | Ac-LTF$r8HYWAQL$F-NH2 | 1657.90 | 829.95 | 830.26 |
| SP-290 | Ac-LTF$r8HYWAQL$W-NH2 | 1696.91 | 849.46 | 849.5 |
| SP-291 | Ac-LTF$r8HYWAQL$R-NH2 | 1666.94 | 834.47 | 834.56 |
| SP-292 | Ac-LTF$r8HYWAQL$K-NH2 | 1638.93 | 820.47 | 820.49 |
| SP-293 | Ac-Q$r8QQTFSN$WRLLAibQN-NH2 | 2080.12 | 1041.06 | 1041.54 |
| SP-294 | Ac-QSQQ$r8FSNLWR$LAibQN-NH2 | 2066.11 | 1034.06 | 1034.58 |
| SP-295 | Ac-LT2Pal$r8HYWAQL$S-NH2 | 1598.86 | 800.43 | 800.49 |
| SP-296 | Ac-LT3Pal$r8HYWAQL$S-NH2 | 1598.86 | 800.43 | 800.49 |
| SP-297 | Ac-LT4Pal$r8HYWAQL$S-NH2 | 1598.86 | 800.43 | 800.49 |
| SP-298 | Ac-LTF2CF3$r8HYWAQL$S-NH2 | 1665.85 | 833.93 | 834.01 |
| SP-299 | Ac-LTF2CN$r8HYWAQL$S-NH2 | 1622.86 | 812.43 | 812.47 |
| SP-300 | Ac-LTF2Me$r8HYWAQL$S-NH2 | 1611.88 | 806.94 | 807 |
| SP-301 | Ac-LTF3CI$r8HYWAQL$S-NH2 | 1631.83 | 816.92 | 816.99 |
| SP-302 | Ac-LTF4CF3$r8HYWAQL$S-NH2 | 1665.85 | 833.93 | 833.94 |
| SP-303 | Ac-LTF4tBu$r8HYWAQL$S-NH2 | 1653.93 | 827.97 | 828.02 |
| SP-304 | Ac-LTF5F$r8HYWAQL$S-NH2 | 1687.82 | 844.91 | 844.96 |
| SP-305 | Ac-LTF$r8HY3BthAAQL$S-NH2 | 1614.83 | 808.42 | 808.48 |
| SP-306 | Ac-LTF2Br$r8HYWAQL$S-NH2 | 1675.78 | 838.89 | 838.97 |
| SP-307 | Ac-LTF4Br$r8HYWAQL$S-NH2 | 1675.78 | 838.89 | 839.86 |
| SP-308 | Ac-LTF2CI$r8HYWAQL$S-NH2 | 1631.83 | 816.92 | 816.99 |
| SP-309 | Ac-LTF4CI$r8HYWAQL$S-NH2 | 1631.83 | 816.92 | 817.36 |
| SP-310 | Ac-LTF3CN$r8HYWAQL$S-NH2 | 1622.86 | 812.43 | 812.47 |
| SP-311 | Ac-LTF4CN$r8HYWAQL$S-NH2 | 1622.86 | 812.43 | 812.47 |
| SP-312 | Ac-LTF34CI2$r8HYWAQL$S-NH2 | 1665.79 | 833.90 | 833.94 |
| SP-313 | Ac-LTF34F2$r8HYWAQL$S-NH2 | 1633.85 | 817.93 | 817.95 |
| SP-314 | Ac-LTF35F2$r8HYWAQL$S-NH2 | 1633.85 | 817.93 | 817.95 |
| SP-315 | Ac-LTDip$r8HYWAQL$S-NH2 | 1673.90 | 837.95 | 838.01 |
| SP-316 | Ac-LTF2F$r8HYWAQL$S-NH2 | 1615.86 | 808.93 | 809 |
| SP-317 | Ac-LTF3F$r8HYWAQL$S-NH2 | 1615.86 | 808.93 | 809 |
| SP-318 | Ac-LTF4F$r8HYWAQL$S-NH2 | 1615.86 | 808.93 | 809 |
| SP-319 | Ac-LTF4I$r8HYWAQL$S-NH2 | 1723.76 | 862.88 | 862.94 |

TABLE 4-continued

| SP | Seq | Exact Mass | M + 2 | Observed mass (m/e) |
|---|---|---|---|---|
| SP-320 | Ac-LTF3Me$r8HYWAQL$S-NH2 | 1611.88 | 806.94 | 807.07 |
| SP-321 | Ac-LTF4Me$r8HYWAQL$S-NH2 | 1611.88 | 806.94 | 807 |
| SP-322 | Ac-LT1Nal$r8HYWAQL$S-NH2 | 1647.88 | 824.94 | 824.98 |
| SP-323 | Ac-LT2Nal$r8HYWAQL$S-NH2 | 1647.88 | 824.94 | 825.06 |
| SP-324 | Ac-LTF3CF3$r8HYWAQL$S-NH2 | 1665.85 | 833.93 | 834.01 |
| SP-325 | Ac-LTF4NO2$r8HYWAQL$S-NH2 | 1642.85 | 822.43 | 822.46 |
| SP-326 | Ac-LTF3NO2$r8HYWAQL$S-NH2 | 1642.85 | 822.43 | 822.46 |
| SP-327 | Ac-LTF$r82ThiYWAQL$S-NH2 | 1613.83 | 807.92 | 807.96 |
| SP-328 | Ac-LTF$r8HBipWAQL$S-NH2 | 1657.90 | 829.95 | 830.01 |
| SP-329 | Ac-LTF$r8HF4tBuWAQL$S-NH2 | 1637.93 | 819.97 | 820.02 |
| SP-330 | Ac-LTF$r8HF4CF3WAQL$S-NH2 | 1649.86 | 825.93 | 826.02 |
| SP-331 | Ac-LTF$r8HF4ClWAQL$S-NH2 | 1615.83 | 808.92 | 809.37 |
| SP-332 | Ac-LTF$r8HF4MeWAQL$S-NH2 | 1595.89 | 798.95 | 799.01 |
| SP-333 | Ac-LTF$r8HF4BrWAQL$S-NH2 | 1659.78 | 830.89 | 830.98 |
| SP-334 | Ac-LTF$r8HF4CNWAQL$S-NH2 | 1606.87 | 804.44 | 804.56 |
| SP-335 | Ac-LTF$r8HF4NO2WAQL$S-NH2 | 1626.86 | 814.43 | 814.55 |
| SP-336 | Ac-LTF$r8H1NalWAQL$S-NH2 | 1631.89 | 816.95 | 817.06 |
| SP-337 | Ac-LTF$r8H2NalWAQL$S-NH2 | 1631.89 | 816.95 | 816.99 |
| SP-338 | Ac-LTF$r8HWAQL$S-NH2 | 1434.80 | 718.40 | 718.49 |
| SP-339 | Ac-LTF$r8HY1NalAQL$S-NH2 | 1608.87 | 805.44 | 805.52 |
| SP-340 | Ac-LTF$r8HY2NalAQL$S-NH2 | 1608.87 | 805.44 | 805.52 |
| SP-341 | Ac-LTF$r8HYWAQI$S-NH2 | 1597.87 | 799.94 | 800.07 |
| SP-342 | Ac-LTF$r8HYWAQNle$S-NH2 | 1597.87 | 799.94 | 800.44 |
| SP-343 | Ac-LTF$er8HYWAQL$eA-NH2 | 1581.87 | 791.94 | 791.98 |
| SP-344 | Ac-LTF$r8HYWAQL$Abu-NH2 | 1595.89 | 798.95 | 799.03 |
| SP-345 | Ac-LTF$r8HYWAbuQL$S-NH2 | 1611.88 | 806.94 | 804.47 |
| SP-346 | Ac-LAF$r8HYWAQL$S-NH2 | 1567.86 | 784.93 | 785.49 |
| SP-347 | Ac-LTF$r8NLWANleL$Q-NH2 | 1550.92 | 776.46 | 777.5 |
| SP-348 | Ac-LTF$r8ALWANleL$Q-NH2 | 1507.92 | 754.96 | 755.52 |
| SP-349 | Ac-LAF$r8NLWANleL$Q-NH2 | 1520.91 | 761.46 | 762.48 |
| SP-350 | Ac-F$r8AYWAAc3cL$A-NH2 | 1256.70 | 629.35 | 1257.56 |
| SP-351 | Ac-LTF$r8AYWAAL$S-NH2 | 1474.82 | 738.41 | 738.55 |
| SP-352 | Ac-LVF$r8AYWAQL$S-NH2 | 1529.87 | 765.94 | 766 |
| SP-353 | Ac-LTF$r8AYWAbuQL$S-NH2 | 1545.86 | 773.93 | 773.92 |
| SP-354 | Ac-LTF$r8AYWNleQL$S-NH2 | 1573.89 | 787.95 | 788.17 |
| SP-355 | Ac-LTF$r8AbuYWAQL$S-NH2 | 1545.86 | 773.93 | 773.99 |
| SP-356 | Ac-LTF$r8AYWHQL$S-NH2 | 1597.87 | 799.94 | 799.97 |
| SP-357 | Ac-LTF$r8AYWKQL$S-NH2 | 1588.90 | 795.45 | 795.53 |

TABLE 4-continued

| SP | Seq | Exact Mass | M + 2 | Observed mass (m/e) |
|---|---|---|---|---|
| SP-358 | Ac-LTF$r8AYWOQL$S-NH2 | 1574.89 | 788.45 | 788.5 |
| SP-359 | Ac-LTF$r8AYWRQL$S-NH2 | 1616.91 | 809.46 | 809.51 |
| SP-360 | Ac-LTF$r8AYWSQL$S-NH2 | 1547.84 | 774.92 | 774.96 |
| SP-361 | Ac-LTF$r8AYWRAL$S-NH2 | 1559.89 | 780.95 | 780.95 |
| SP-362 | Ac-LTF$r8AYWRQL$A-NH2 | 1600.91 | 801.46 | 801.52 |
| SP-363 | Ac-LTF$r8AYWRAL$A-NH2 | 1543.89 | 772.95 | 773.03 |
| SP-364 | Ac-LTF$r5HYWAQL$s8S-NH2 | 1597.87 | 799.94 | 799.97 |
| SP-365 | Ac-LTF$HYWAQL$r8S-NH2 | 1597.87 | 799.94 | 799.97 |
| SP-366 | Ac-LTF$r8HYWAAL$S-NH2 | 1540.84 | 771.42 | 771.48 |
| SP-367 | Ac-LTF$r8HYWAAbuL$S-NH2 | 1554.86 | 778.43 | 778.51 |
| SP-368 | Ac-LTF$r8HYWALL$S-NH2 | 1582.89 | 792.45 | 792.49 |
| SP-369 | Ac-F$r8AYWHAL$A-NH2 | 1310.72 | 656.36 | 656.4 |
| SP-370 | Ac-F$r8AYWAAL$A-NH2 | 1244.70 | 623.35 | 1245.61 |
| SP-371 | Ac-F$r8AYWSAL$A-NH2 | 1260.69 | 631.35 | 1261.6 |
| SP-372 | Ac-F$r8AYWRAL$A-NH2 | 1329.76 | 665.88 | 1330.72 |
| SP-373 | Ac-F$r8AYWKAL$A-NH2 | 1301.75 | 651.88 | 1302.67 |
| SP-374 | Ac-F$r8AYWOAL$A-NH2 | 1287.74 | 644.87 | 1289.13 |
| SP-375 | Ac-F$r8VYWEAc3cL$A-NH2 | 1342.73 | 672.37 | 1343.67 |
| SP-376 | Ac-F$r8FYWEAc3cL$A-NH2 | 1390.73 | 696.37 | 1392.14 |
| SP-377 | Ac-F$r8WYWEAc3cL$A-NH2 | 1429.74 | 715.87 | 1431.44 |
| SP-378 | Ac-F$r8RYWEAc3cL$A-NH2 | 1399.77 | 700.89 | 700.95 |
| SP-379 | Ac-F$r8KYWEAc3cL$A-NH2 | 1371.76 | 686.88 | 686.97 |
| SP-380 | Ac-F$r8ANleWEAc3cL$A-NH2 | 1264.72 | 633.36 | 1265.59 |
| SP-381 | Ac-F$r8AVWEAc3cL$A-NH2 | 1250.71 | 626.36 | 1252.2 |
| SP-382 | Ac-F$r8AFWEAc3cL$A-NH2 | 1298.71 | 650.36 | 1299.64 |
| SP-383 | Ac-F$r8AWWEAc3cL$A-NH2 | 1337.72 | 669.86 | 1338.64 |
| SP-384 | Ac-F$r8ARWEAc3cL$A-NH2 | 1307.74 | 654.87 | 655 |
| SP-385 | Ac-F$r8AKWEAc3cL$A-NH2 | 1279.73 | 640.87 | 641.01 |
| SP-386 | Ac-F$r8AYWVAc3cL$A-NH2 | 1284.73 | 643.37 | 643.38 |
| SP-387 | Ac-F$r8AYWFAc3cL$A-NH2 | 1332.73 | 667.37 | 667.43 |
| SP-388 | Ac-F$r8AYWWAc3cL$A-NH2 | 1371.74 | 686.87 | 686.97 |
| SP-389 | Ac-F$r8AYWRAc3cL$A-NH2 | 1341.76 | 671.88 | 671.94 |
| SP-390 | Ac-F$r8AYWKAc3cL$A-NH2 | 1313.75 | 657.88 | 657.88 |
| SP-391 | Ac-F$r8AYWEVL$A-NH2 | 1330.73 | 666.37 | 666.47 |
| SP-392 | Ac-F$r8AYWEFL$A-NH2 | 1378.73 | 690.37 | 690.44 |
| SP-393 | Ac-F$r8AYWEWL$A-NH2 | 1417.74 | 709.87 | 709.91 |
| SP-394 | Ac-F$r8AYWERL$A-NH2 | 1387.77 | 694.89 | 1388.66 |
| SP-395 | Ac-F$r8AYWEKL$A-NH2 | 1359.76 | 680.88 | 1361.21 |

TABLE 4-continued

| SP | Seq | Exact Mass | M + 2 | Observed mass (m/e) |
|---|---|---|---|---|
| SP-396 | Ac-F$r8AYWEAc3cL$V-NH2 | 1342.73 | 672.37 | 1343.59 |
| SP-397 | Ac-F$r8AYWEAc3cL$F-NH2 | 1390.73 | 696.37 | 1392.58 |
| SP-398 | Ac-F$r8AYWEAc3cL$W-NH2 | 1429.74 | 715.87 | 1431.29 |
| SP-399 | Ac-F$r8AYWEAc3cL$R-NH2 | 1399.77 | 700.89 | 700.95 |
| SP-400 | Ac-F$r8AYWEAc3cL$K-NH2 | 1371.76 | 686.88 | 686.97 |
| SP-401 | Ac-F$r8AYWEAc3cL$AV-NH2 | 1413.77 | 707.89 | 707.91 |
| SP-402 | Ac-F$r8AYWEAc3cL$AF-NH2 | 1461.77 | 731.89 | 731.96 |
| SP-403 | Ac-F$r8AYWEAc3cL$AW-NH2 | 1500.78 | 751.39 | 751.5 |
| SP-404 | Ac-F$r8AYWEAc3cL$AR-NH2 | 1470.80 | 736.40 | 736.47 |
| SP-405 | Ac-F$r8AYWEAc3cL$AK-NH2 | 1442.80 | 722.40 | 722.41 |
| SP-406 | Ac-F$r8AYWEAc3cL$AH-NH2 | 1451.76 | 726.88 | 726.93 |
| SP-407 | Ac-LTF2NO2$r8HYWAQL$S-NH2 | 1642.85 | 822.43 | 822.54 |
| SP-408 | Ac-LTA$r8HYAAQL$S-NH2 | 1406.79 | 704.40 | 704.5 |
| SP-409 | Ac-LTF$r8HYAAQL$S-NH2 | 1482.82 | 742.41 | 742.47 |
| SP-410 | Ac-QSQQTF$r8NLWALL$AN-NH2 | 1966.07 | 984.04 | 984.38 |
| SP-411 | Ac-QAibQQTF$r8NLWALL$AN-NH2 | 1964.09 | 983.05 | 983.42 |
| SP-412 | Ac-QAibQQTF$r8ALWALL$AN-NH2 | 1921.08 | 961.54 | 961.59 |
| SP-413 | Ac-AAAATF$r8AAWAAL$AA-NH2 | 1608.90 | 805.45 | 805.52 |
| SP-414 | Ac-F$r8AAWRAL$Q-NH2 | 1294.76 | 648.38 | 648.48 |
| SP-415 | Ac-TF$r8AAWAAL$Q-NH2 | 1310.74 | 656.37 | 1311.62 |
| SP-416 | Ac-TF$r8AAWRAL$A-NH2 | 1338.78 | 670.39 | 670.46 |
| SP-417 | Ac-VF$r8AAWRAL$Q-NH2 | 1393.82 | 697.91 | 697.99 |
| SP-418 | Ac-AF$r8AAWAAL$A-NH2 | 1223.71 | 612.86 | 1224.67 |
| SP-420 | Ac-TF$r8AAWKAL$Q-NH2 | 1367.80 | 684.90 | 684.97 |
| SP-421 | Ac-TF$r8AAWOAL$Q-NH2 | 1353.78 | 677.89 | 678.01 |
| SP-422 | Ac-TF$r8AAWSAL$Q-NH2 | 1326.73 | 664.37 | 664.47 |
| SP-423 | Ac-LTF$r8AAWRAL$Q-NH2 | 1508.89 | 755.45 | 755.49 |
| SP-424 | Ac-F$r8AYWAQL$A-NH2 | 1301.72 | 651.86 | 651.96 |
| SP-425 | Ac-F$r8AWWAAL$A-NH2 | 1267.71 | 634.86 | 634.87 |
| SP-426 | Ac-F$r8AWWAQL$A-NH2 | 1324.73 | 663.37 | 663.43 |
| SP-427 | Ac-F$r8AYWEAL$-NH2 | 1231.66 | 616.83 | 1232.93 |
| SP-428 | Ac-F$r8AYWAAL$-NH2 | 1173.66 | 587.83 | 1175.09 |
| SP-429 | Ac-F$r8AYWKAL$-NH2 | 1230.72 | 616.36 | 616.44 |
| SP-430 | Ac-F$r8AYWOAL$-NH2 | 1216.70 | 609.35 | 609.48 |
| SP-431 | Ac-F$r8AYWQAL$-NH2 | 1230.68 | 616.34 | 616.44 |
| SP-432 | Ac-F$r8AYWAQL$-NH2 | 1230.68 | 616.34 | 616.37 |
| SP-433 | Ac-F$r8HYWDQL$S-NH2 | 1427.72 | 714.86 | 714.86 |
| SP-434 | Ac-F$r8HFWEQL$S-NH2 | 1425.74 | 713.87 | 713.98 |

TABLE 4-continued

| SP | Seq | Exact Mass | M + 2 | Observed mass (m/e) |
|---|---|---|---|---|
| SP-435 | Ac-F$r8AYWHQL$S-NH2 | 1383.73 | 692.87 | 692.96 |
| SP-436 | Ac-F$r8AYWKQL$S-NH2 | 1374.77 | 688.39 | 688.45 |
| SP-437 | Ac-F$r8AYWOQL$S-NH2 | 1360.75 | 681.38 | 681.49 |
| SP-438 | Ac-F$r8HYWSQL$S-NH2 | 1399.73 | 700.87 | 700.95 |
| SP-439 | Ac-F$r8HWWEQL$S-NH2 | 1464.76 | 733.38 | 733.44 |
| SP-440 | Ac-F$r8HWWAQL$S-NH2 | 1406.75 | 704.38 | 704.43 |
| SP-441 | Ac-F$r8AWWHQL$S-NH2 | 1406.75 | 704.38 | 704.43 |
| SP-442 | Ac-F$r8AWWKQL$S-NH2 | 1397.79 | 699.90 | 699.92 |
| SP-443 | Ac-F$r8AWWOQL$S-NH2 | 1383.77 | 692.89 | 692.96 |
| SP-444 | Ac-F$r8HWWSQL$S-NH2 | 1422.75 | 712.38 | 712.42 |
| SP-445 | Ac-LTF$r8NYWANleL$Q-NH2 | 1600.90 | 801.45 | 801.52 |
| SP-446 | Ac-LTF$r8NLWAQL$Q-NH2 | 1565.90 | 783.95 | 784.06 |
| SP-447 | Ac-LTF$r8NYWANleL$A-NH2 | 1543.88 | 772.94 | 773.03 |
| SP-448 | Ac-LTF$r8NLWAQL$A-NH2 | 1508.88 | 755.44 | 755.49 |
| SP-449 | Ac-LTF$r8AYWANleL$Q-NH2 | 1557.90 | 779.95 | 780.06 |
| SP-450 | Ac-LTF$r8ALWAQL$Q-NH2 | 1522.89 | 762.45 | 762.45 |
| SP-451 | Ac-LAF$r8NYWANleL$Q-NH2 | 1570.89 | 786.45 | 786.5 |
| SP-452 | Ac-LAF$r8NLWAQL$Q-NH2 | 1535.89 | 768.95 | 769.03 |
| SP-453 | Ac-LAF$r8AYWANleL$A-NH2 | 1470.86 | 736.43 | 736.47 |
| SP-454 | Ac-LAF$r8ALWAQL$A-NH2 | 1435.86 | 718.93 | 719.01 |
| SP-455 | Ac-LAF$r8AYWAAL$A-NH2 | 1428.82 | 715.41 | 715.41 |
| SP-456 | Ac-F$r8AYWEAc3cL$AAib-NH2 | 1399.75 | 700.88 | 700.95 |
| SP-457 | Ac-F$r8AYWAQL$AA-NH2 | 1372.75 | 687.38 | 687.78 |
| SP-458 | Ac-F$r8AYWAAc3cL$AA-NH2 | 1327.73 | 664.87 | 664.84 |
| SP-459 | Ac-F$r8AYWSAc3cL$AA-NH2 | 1343.73 | 672.87 | 672.9 |
| SP-460 | Ac-F$r8AYWEAc3cL$AS-NH2 | 1401.73 | 701.87 | 701.84 |
| SP-461 | Ac-F$r8AYWEAc3cL$AT-NH2 | 1415.75 | 708.88 | 708.87 |
| SP-462 | Ac-F$r8AYWEAc3cL$AL-NH2 | 1427.79 | 714.90 | 714.94 |
| SP-463 | Ac-F$r8AYWEAc3cL$AQ-NH2 | 1442.76 | 722.38 | 722.41 |
| SP-464 | Ac-F$r8AFWEAc3cL$AA-NH2 | 1369.74 | 685.87 | 685.93 |
| SP-465 | Ac-F$r8AWWEAc3cL$AA-NH2 | 1408.75 | 705.38 | 705.39 |
| SP-466 | Ac-F$r8AYWEAc3cL$SA-NH2 | 1401.73 | 701.87 | 701.99 |
| SP-467 | Ac-F$r8AYWEAL$AA-NH2 | 1373.74 | 687.87 | 687.93 |
| SP-468 | Ac-F$r8AYWENleL$AA-NH2 | 1415.79 | 708.90 | 708.94 |
| SP-469 | Ac-F$r8AYWEAc3cL$AbuA-NH2 | 1399.75 | 700.88 | 700.95 |
| SP-470 | Ac-F$r8AYWEAc3cL$NleA-NH2 | 1427.79 | 714.90 | 714.86 |
| SP-471 | Ac-F$r8AYWEAibL$NleA-NH2 | 1429.80 | 715.90 | 715.97 |
| SP-472 | Ac-F$r8AYWEAL$NleA-NH2 | 1415.79 | 708.90 | 708.94 |

TABLE 4-continued

| SP | Seq | Exact Mass | M + 2 | Observed mass (m/e) |
|---|---|---|---|---|
| SP-473 | Ac-F$r8AYWENleL$NleA-NH2 | 1457.83 | 729.92 | 729.96 |
| SP-474 | Ac-F$r8AYWEAibL$Abu-NH2 | 1330.73 | 666.37 | 666.39 |
| SP-475 | Ac-F$r8AYWENleL$Abu-NH2 | 1358.76 | 680.38 | 680.39 |
| SP-476 | Ac-F$r8AYWEAL$Abu-NH2 | 1316.72 | 659.36 | 659.36 |
| SP-477 | Ac-LTF$r8AFWAQL$S-NH2 | 1515.85 | 758.93 | 759.12 |
| SP-478 | Ac-LTF$r8AWWAQL$S-NH2 | 1554.86 | 778.43 | 778.51 |
| SP-479 | Ac-LTF$r8AYWAQI$S-NH2 | 1531.84 | 766.92 | 766.96 |
| SP-480 | Ac-LTF$r8AYWAQNle$S-NH2 | 1531.84 | 766.92 | 766.96 |
| SP-481 | Ac-LTF$r8AYWAQL$SA-NH2 | 1602.88 | 802.44 | 802.48 |
| SP-482 | Ac-LTF$r8AWWAQL$A-NH2 | 1538.87 | 770.44 | 770.89 |
| SP-483 | Ac-LTF$r8AYWAQI$A-NH2 | 1515.85 | 758.93 | 759.42 |
| SP-484 | Ac-LTF$r8AYWAQNle$A-NH2 | 1515.85 | 758.93 | 759.42 |
| SP-485 | Ac-LTF$r8AYWAQL$AA-NH2 | 1586.89 | 794.45 | 794.94 |
| SP-486 | Ac-LTF$r8HWWAQL$S-NH2 | 1620.88 | 811.44 | 811.47 |
| SP-487 | Ac-LTF$r8HRWAQL$S-NH2 | 1590.90 | 796.45 | 796.52 |
| SP-488 | Ac-LTF$r8HKWAQL$S-NH2 | 1562.90 | 782.45 | 782.53 |
| SP-489 | Ac-LTF$r8HYWAQL$W-NH2 | 1696.91 | 849.46 | 849.5 |
| SP-491 | Ac-F$r8AYWAbuAL$A-NH2 | 1258.71 | 630.36 | 630.5 |
| SP-492 | Ac-F$r8AbuYWEAL$A-NH2 | 1316.72 | 659.36 | 659.51 |
| SP-493 | Ac-NlePRF%r8NYWRLL%QN-NH2 | 1954.13 | 978.07 | 978.54 |
| SP-494 | Ac-TSF%r8HYWAQL%S-NH2 | 1573.83 | 787.92 | 787.98 |
| SP-495 | Ac-LTF%r8AYWAQL%S-NH2 | 1533.86 | 767.93 | 768 |
| SP-496 | Ac-HTF$r8HYWAQL$S-NH2 | 1621.84 | 811.92 | 811.96 |
| SP-497 | Ac-LHF$r8HYWAQL$S-NH2 | 1633.88 | 817.94 | 818.02 |
| SP-498 | Ac-LTF$r8HHWAQL$S-NH2 | 1571.86 | 786.93 | 786.94 |
| SP-499 | Ac-LTF$r8HYWHQL$S-NH2 | 1663.89 | 832.95 | 832.38 |
| SP-500 | Ac-LTF$r8HYWAHL$S-NH2 | 1606.87 | 804.44 | 804.48 |
| SP-501 | Ac-LTF$r8HYWAQL$H-NH2 | 1647.89 | 824.95 | 824.98 |
| SP-502 | Ac-LTF$r8HYWAQL$S-NHPr | 1639.91 | 820.96 | 820.98 |
| SP-503 | Ac-LTF$r8HYWAQL$S-NHsBu | 1653.93 | 827.97 | 828.02 |
| SP-504 | Ac-LTF$r8HYWAQL$S-NHiBu | 1653.93 | 827.97 | 828.02 |
| SP-505 | Ac-LTF$r8HYWAQL$S-NHBn | 1687.91 | 844.96 | 844.44 |
| SP-506 | Ac-LTF$r8HYWAQL$S-NHPe | 1700.92 | 851.46 | 851.99 |
| SP-507 | Ac-LTF$r8HYWAQL$S-NHChx | 1679.94 | 840.97 | 841.04 |
| SP-508 | Ac-ETF$r8AYWAQL$S-NH2 | 1547.80 | 774.90 | 774.96 |
| SP-509 | Ac-STF$r8AYWAQL$S-NH2 | 1505.79 | 753.90 | 753.94 |
| SP-510 | Ac-LEF$r8AYWAQL$S-NH2 | 1559.84 | 780.92 | 781.25 |
| SP-511 | Ac-LSF$r8AYWAQL$S-NH2 | 1517.83 | 759.92 | 759.93 |

TABLE 4-continued

| SP | Seq | Exact Mass | M + 2 | Observed mass (m/e) |
|---|---|---|---|---|
| SP-512 | Ac-LTF$r8EYWAQL$S-NH2 | 1589.85 | 795.93 | 795.97 |
| SP-513 | Ac-LTF$r8SYWAQL$S-NH2 | 1547.84 | 774.92 | 774.96 |
| SP-514 | Ac-LTF$r8AYWEQL$S-NH2 | 1589.85 | 795.93 | 795.9 |
| SP-515 | Ac-LTF$r8AYWAEL$S-NH2 | 1532.83 | 767.42 | 766.96 |
| SP-516 | Ac-LTF$r8AYWASL$S-NH2 | 1490.82 | 746.41 | 746.46 |
| SP-517 | Ac-LTF$r8AYWAQL$E-NH2 | 1573.85 | 787.93 | 787.98 |
| SP-518 | Ac-LTF2CN$r8HYWAQL$S-NH2 | 1622.86 | 812.43 | 812.47 |
| SP-519 | Ac-LTF3CI$r8HYWAQL$S-NH2 | 1631.83 | 816.92 | 816.99 |
| SP-520 | Ac-LTDip$r8HYWAQL$S-NH2 | 1673.90 | 837.95 | 838.01 |
| SP-521 | Ac-LTF$r8HYWAQTle$S-NH2 | 1597.87 | 799.94 | 800.04 |
| SP-522 | Ac-F$r8AY6clWEAL$A-NH2 | 1336.66 | 669.33 | 1338.56 |
| SP-523 | Ac-F$r8AYdl6brWEAL$A-NH2 | 1380.61 | 691.31 | 692.2 |
| SP-524 | Ac-F$r8AYdl6fWEAL$A-NH2 | 1320.69 | 661.35 | 1321.61 |
| SP-525 | Ac-F$r8AYdl4mWEAL$A-NH2 | 1316.72 | 659.36 | 659.36 |
| SP-526 | Ac-F$r8AYdl5clWEAL$A-NH2 | 1336.66 | 669.33 | 669.35 |
| SP-527 | Ac-F$r8AYdl7mWEAL$A-NH2 | 1316.72 | 659.36 | 659.36 |
| SP-528 | Ac-LTF%r8HYWAQL%A-NH2 | 1583.89 | 792.95 | 793.01 |
| SP-529 | Ac-LTF$r8HCouWAQL$S-NH2 | 1679.87 | 840.94 | 841.38 |
| SP-530 | Ac-LTFEHCouWAQLTS-NH2 | 1617.75 | 809.88 | 809.96 |
| SP-531 | Ac-LTA$r8HCouWAQL$S-NH2 | 1603.84 | 802.92 | 803.36 |
| SP-532 | Ac-F$r8AYWEAL$AbuA-NH2 | 1387.75 | 694.88 | 694.88 |
| SP-533 | Ac-F$r8AYWEAI$AA-NH2 | 1373.74 | 687.87 | 687.93 |
| SP-534 | Ac-F$r8AYWEANle$AA-NH2 | 1373.74 | 687.87 | 687.93 |
| SP-535 | Ac-F$r8AYWEAmIL$AA-NH2 | 1429.80 | 715.90 | 715.97 |
| SP-536 | Ac-F$r8AYWQAL$AA-NH2 | 1372.75 | 687.38 | 687.48 |
| SP-537 | Ac-F$r8AYWAAL$AA-NH2 | 1315.73 | 658.87 | 658.92 |
| SP-538 | Ac-F$r8AYWAbuAL$AA-NH2 | 1329.75 | 665.88 | 665.95 |
| SP-539 | Ac-F$r8AYWNleAL$AA-NH2 | 1357.78 | 679.89 | 679.94 |
| SP-540 | Ac-F$r8AbuYWEAL$AA-NH2 | 1387.75 | 694.88 | 694.96 |
| SP-541 | Ac-F$r8NleYWEAL$AA-NH2 | 1415.79 | 708.90 | 708.94 |
| SP-542 | Ac-F$r8FYWEAL$AA-NH2 | 1449.77 | 725.89 | 725.97 |
| SP-543 | Ac-LTF$r8HYWAQhL$S-NH2 | 1611.88 | 806.94 | 807 |
| SP-544 | Ac-LTF$r8HYWAQAdm$S-NH2 | 1675.91 | 838.96 | 839.04 |
| SP-545 | Ac-LTF$r8HYWAQIgl$S-NH2 | 1659.88 | 830.94 | 829.94 |
| SP-546 | Ac-F$r8AYWAQL$AA-NH2 | 1372.75 | 687.38 | 687.48 |
| SP-547 | Ac-LTF$r8ALWAQL$Q-NH2 | 1522.89 | 762.45 | 762.52 |
| SP-548 | Ac-F$r8AYWEAL$AA-NH2 | 1373.74 | 687.87 | 687.93 |
| SP-549 | Ac-F$r8AYWENleL$AA-NH2 | 1415.79 | 708.90 | 708.94 |

TABLE 4-continued

| SP | Seq | Exact Mass | M + 2 | Observed mass (m/e) |
|---|---|---|---|---|
| SP-550 | Ac-F$r8AYWEAibL$Abu-NH2 | 1330.73 | 666.37 | 666.39 |
| SP-551 | Ac-F$r8AYWENleL$Abu-NH2 | 1358.76 | 680.38 | 680.38 |
| SP-552 | Ac-F$r8AYWEAL$Abu-NH2 | 1316.72 | 659.36 | 659.36 |
| SP-553 | Ac-F$r8AYWEAc3cL$AbuA-NH2 | 1399.75 | 700.88 | 700.95 |
| SP-554 | Ac-F$r8AYWEAc3cL$NleA-NH2 | 1427.79 | 714.90 | 715.01 |
| SP-555 | H-LTF$r8AYWAQL$S-NH2 | 1489.83 | 745.92 | 745.95 |
| SP-556 | mdPEG3-LTF$r8AYWAQL$S-NH2 | 1679.92 | 840.96 | 840.97 |
| SP-557 | mdPEG7-LTF$r8AYWAQL$S-NH2 | 1856.02 | 929.01 | 929.03 |
| SP-558 | Ac-F$r8ApmpEt6cIWEAL$A-NH2 | 1470.71 | 736.36 | 788.17 |
| SP-559 | Ac-LTF3CI$r8AYWAQL$S-NH2 | 1565.81 | 783.91 | 809.18 |
| SP-560 | Ac-LTF3CI$r8HYWAQL$A-NH2 | 1615.83 | 808.92 | 875.24 |
| SP-561 | Ac-LTF3CI$r8HYWWQL$S-NH2 | 1746.87 | 874.44 | 841.65 |
| SP-562 | Ac-LTF3CI$r8AYWWQL$S-NH2 | 1680.85 | 841.43 | 824.63 |
| SP-563 | Ac-LTF$r8AYWWQL$S-NH2 | 1646.89 | 824.45 | 849.98 |
| SP-564 | Ac-LTF$r8HYWWQL$A-NH2 | 1696.91 | 849.46 | 816.67 |
| SP-565 | Ac-LTF$r8AYWWQL$A-NH2 | 1630.89 | 816.45 | 776.15 |
| SP-566 | Ac-LTF4F$r8AYWAQL$S-NH2 | 1549.83 | 775.92 | 776.15 |
| SP-567 | Ac-LTF2F$r8AYWAQL$S-NH2 | 1549.83 | 775.92 | 776.15 |
| SP-568 | Ac-LTF3F$r8AYWAQL$S-NH2 | 1549.83 | 775.92 | 785.12 |
| SP-569 | Ac-LTF34F2$r8AYWAQL$S-NH2 | 1567.83 | 784.92 | 785.12 |
| SP-570 | Ac-LTF35F2$r8AYWAQL$S-NH2 | 1567.83 | 784.92 | 1338.74 |
| SP-571 | Ac-F3CI$r8AYWEAL$A-NH2 | 1336.66 | 669.33 | 705.28 |
| SP-572 | Ac-F3CI$r8AYWEAL$AA-NH2 | 1407.70 | 704.85 | 680.11 |
| SP-573 | Ac-F$r8AY6cIWEAL$AA-NH2 | 1407.70 | 704.85 | 736.83 |
| SP-574 | Ac-F$r8AY6cIWEAL$-NH2 | 1265.63 | 633.82 | 784.1 |
| SP-575 | Ac-LTF$r8HYWAQLSt/S-NH2 | 16.03 | 9.02 | 826.98 |
| SP-576 | Ac-LTF$r8HYWAQL$S-NHsBu | 1653.93 | 827.97 | 828.02 |
| SP-577 | Ac-STF$r8AYWAQL$S-NH2 | 1505.79 | 753.90 | 753.94 |
| SP-578 | Ac-LTF$r8AYWAEL$S-NH2 | 1532.83 | 767.42 | 767.41 |
| SP-579 | Ac-LTF$r8AYWAQL$E-NH2 | 1573.85 | 787.93 | 787.98 |
| SP-580 | mdPEG3-LTF$r8AYWAQL$S-NH2 | 1679.92 | 840.96 | 840.97 |
| SP-581 | Ac-LTF$r8AYWAQhL$S-NH2 | 1545.86 | 773.93 | 774.31 |
| SP-583 | Ac-LTF$r8AYWAQCha$S-NH2 | 1571.88 | 786.94 | 787.3 |
| SP-584 | Ac-LTF$r8AYWAQChg$S-NH2 | 1557.86 | 779.93 | 780.4 |
| SP-585 | Ac-LTF$r8AYWAQCba$S-NH2 | 1543.84 | 772.92 | 780.13 |
| SP-586 | Ac-LTF$r8AYWAQF$S-NH2 | 1565.83 | 783.92 | 784.2 |
| SP-587 | Ac-LTF4F$r8HYWAQhL$S-NH2 | 1629.87 | 815.94 | 815.36 |
| SP-588 | Ac-LTF4F$r8HYWAQCha$S-NH2 | 1655.89 | 828.95 | 828.39 |

TABLE 4-continued

| SP | Seq | Exact Mass | M + 2 | Observed mass (m/e) |
|---|---|---|---|---|
| SP-589 | Ac-LTF4F$r8HYWAQChg$S-NH2 | 1641.87 | 821.94 | 821.35 |
| SP-590 | Ac-LTF4F$r8HYWAQCba$S-NH2 | 1627.86 | 814.93 | 814.32 |
| SP-591 | Ac-LTF4F$r8AYWAQhL$S-NH2 | 1563.85 | 782.93 | 782.36 |
| SP-592 | Ac-LTF4F$r8AYWAQCha$S-NH2 | 1589.87 | 795.94 | 795.38 |
| SP-593 | Ac-LTF4F$r8AYWAQChg$S-NH2 | 1575.85 | 788.93 | 788.35 |
| SP-594 | Ac-LTF4F$r8AYWAQCba$S-NH2 | 1561.83 | 781.92 | 781.39 |
| SP-595 | Ac-LTF3CI$r8AYWAQhL$S-NH2 | 1579.82 | 790.91 | 790.35 |
| SP-596 | Ac-LTF3CI$r8AYWAQCha$S-NH2 | 1605.84 | 803.92 | 803.67 |
| SP-597 | Ac-LTF3CI$r8AYWAQChg$S-NH2 | 1591.82 | 796.91 | 796.34 |
| SP-598 | Ac-LTF3CI$r8AYWAQCba$S-NH2 | 1577.81 | 789.91 | 789.39 |
| SP-599 | Ac-LTF$r8AYWAQhF$S-NH2 | 1579.84 | 790.92 | 791.14 |
| SP-600 | Ac-LTF$r8AYWAQF3CF3$S-NH2 | 1633.82 | 817.91 | 818.15 |
| SP-601 | Ac-LTF$r8AYWAQF3Me$S-NH2 | 1581.86 | 791.93 | 791.32 |
| SP-602 | Ac-LTF$r8AYWAQ1Nal$S-NH2 | 1615.84 | 808.92 | 809.18 |
| SP-603 | Ac-LTF$r8AYWAQBip$S-NH2 | 1641.86 | 821.93 | 822.13 |
| SP-604 | Ac-LTF$r8FYWAQL$A-NH2 | 1591.88 | 796.94 | 797.33 |
| SP-605 | Ac-LTF$r8HYWAQL$S-NHAm | 1667.94 | 834.97 | 835.92 |
| SP-606 | Ac-LTF$r8HYWAQL$S-NHiAm | 1667.94 | 834.97 | 835.55 |
| SP-607 | Ac-LTF$r8HYWAQL$S-NHnPr3Ph | 1715.94 | 858.97 | 859.79 |
| SP-608 | Ac-LTF$r8HYWAQL$S-NHnBu3,3Me | 1681.96 | 841.98 | 842.49 |
| SP-610 | Ac-LTF$r8HYWAQL$S-NHnPr | 1639.91 | 820.96 | 821.58 |
| SP-611 | Ac-LTF$r8HYWAQL$S-NHnEt2Ch | 1707.98 | 854.99 | 855.35 |
| SP-612 | Ac-LTF$r8HYWAQL$S-NHHex | 1681.96 | 841.98 | 842.4 |
| SP-613 | Ac-LTF$r8AYWAQL$S-NHmdPeg2 | 1633.91 | 817.96 | 818.35 |
| SP-614 | Ac-LTF$r8AYWAQL$A-NHmdPeg2 | 1617.92 | 809.96 | 810.3 |
| SP-615 | Ac-LTF$r8AYWAQL$A-NHmdPeg4 | 1705.97 | 853.99 | 854.33 |
| SP-616 | Ac-F$r8AYdI4mWEAL$A-NH2 | 1316.72 | 659.36 | 659.44 |
| SP-617 | Ac-F$r8AYdI5cIWEAL$A-NH2 | 1336.66 | 669.33 | 669.43 |
| SP-618 | Ac-LThF$r8AYWAQL$S-NH2 | 1545.86 | 773.93 | 774.11 |
| SP-619 | Ac-LT2Nal$r8AYWAQL$S-NH2 | 1581.86 | 791.93 | 792.43 |
| SP-620 | Ac-LTA$r8AYWAQL$S-NH2 | 1455.81 | 728.91 | 729.15 |
| SP-621 | Ac-LTF$r8AYWVQL$S-NH2 | 1559.88 | 780.94 | 781.24 |
| SP-622 | Ac-LTF$r8HYWAAL$A-NH2 | 1524.85 | 763.43 | 763.86 |
| SP-623 | Ac-LTF$r8VYWAQL$A-NH2 | 1543.88 | 772.94 | 773.37 |
| SP-624 | Ac-LTF$r8IYWAQL$S-NH2 | 1573.89 | 787.95 | 788.17 |
| SP-625 | Ac-FTF$r8VYWSQL$S-NH2 | 1609.85 | 805.93 | 806.22 |
| SP-626 | Ac-ITF$r8FYWAQL$S-NH2 | 1607.88 | 804.94 | 805.2 |
| SP-627 | Ac-2NalTF$r8VYWSQL$S-NH2 | 1659.87 | 830.94 | 831.2 |

TABLE 4-continued

| SP | Seq | Exact Mass | M + 2 | Observed mass (m/e) |
|---|---|---|---|---|
| SP-628 | Ac-ITF$r8LYWSQL$S-NH2 | 1589.89 | 795.95 | 796.13 |
| SP-629 | Ac-FTF$r8FYWAQL$S-NH2 | 1641.86 | 821.93 | 822.13 |
| SP-630 | Ac-WTF$r8VYWAQL$S-NH2 | 1632.87 | 817.44 | 817.69 |
| SP-631 | Ac-WTF$r8WYWAQL$S-NH2 | 1719.88 | 860.94 | 861.36 |
| SP-632 | Ac-VTF$r8AYWSQL$S-NH2 | 1533.82 | 767.91 | 768.19 |
| SP-633 | Ac-WTF$r8FYWSQL$S-NH2 | 1696.87 | 849.44 | 849.7 |
| SP-634 | Ac-FTF$r8IYWAQL$S-NH2 | 1607.88 | 804.94 | 805.2 |
| SP-635 | Ac-WTF$r8VYWSQL$S-NH2 | 1648.87 | 825.44 | 824.8 |
| SP-636 | Ac-FTF$r8LYWSQL$S-NH2 | 1623.87 | 812.94 | 812.8 |
| SP-637 | Ac-YTF$r8FYWSQL$S-NH2 | 1673.85 | 837.93 | 837.8 |
| SP-638 | Ac-LTF$r8AY6cIWEAL$A-NH2 | 1550.79 | 776.40 | 776.14 |
| SP-639 | Ac-LTF$r8AY6cIWSQL$S-NH2 | 1581.80 | 791.90 | 791.68 |
| SP-640 | Ac-F$r8AY6cIWSAL$A-NH2 | 1294.65 | 648.33 | 647.67 |
| SP-641 | Ac-F$r8AY6cIWQAL$AA-NH2 | 1406.72 | 704.36 | 703.84 |
| SP-642 | Ac-LHF$r8AYWAQL$S-NH2 | 1567.86 | 784.93 | 785.21 |
| SP-643 | Ac-LTF$r8AYWAQL$S-NH2 | 1531.84 | 766.92 | 767.17 |
| SP-644 | Ac-LTF$r8AHWAQL$S-NH2 | 1505.84 | 753.92 | 754.13 |
| SP-645 | Ac-LTF$r8AYWAHL$S-NH2 | 1540.84 | 771.42 | 771.61 |
| SP-646 | Ac-LTF$r8AYWAQL$H-NH2 | 1581.87 | 791.94 | 792.15 |
| SP-647 | H-LTF$r8AYWAQL$A-NH2 | 1473.84 | 737.92 | 737.29 |
| SP-648 | Ac-HHF$r8AYWAQL$S-NH2 | 1591.83 | 796.92 | 797.35 |
| SP-649 | Ac-aAibWTF$r8VYWSQL$S-NH2 | 1804.96 | 903.48 | 903.64 |
| SP-650 | Ac-AibWTF$r8HYWAQL$S-NH2 | 1755.91 | 878.96 | 879.4 |
| SP-651 | Ac-AibAWTF$r8HYWAQL$S-NH2 | 1826.95 | 914.48 | 914.7 |
| SP-652 | Ac-fWTF$r8HYWAQL$S-NH2 | 1817.93 | 909.97 | 910.1 |
| SP-653 | Ac-AibWWTF$r8HYWAQL$S-NH2 | 1941.99 | 972.00 | 972.2 |
| SP-654 | Ac-WTF$r8LYWSQL$S-NH2 | 1662.88 | 832.44 | 832.8 |
| SP-655 | Ac-WTF$r8NleYWSQL$S-NH2 | 1662.88 | 832.44 | 832.6 |
| SP-656 | Ac-LTF$r8AYWSQL$a-NH2 | 1531.84 | 766.92 | 767.2 |
| SP-657 | Ac-LTF$r8EYWARL$A-NH2 | 1601.90 | 801.95 | 802.1 |
| SP-658 | Ac-LTF$r8EYWAHL$A-NH2 | 1582.86 | 792.43 | 792.6 |
| SP-659 | Ac-aTF$r8AYWAQL$S-NH2 | 1489.80 | 745.90 | 746.08 |
| SP-660 | Ac-AibTF$r8AYWAQL$S-NH2 | 1503.81 | 752.91 | 753.11 |
| SP-661 | Ac-AmfTF$r8AYWAQL$S-NH2 | 1579.84 | 790.92 | 791.14 |
| SP-662 | Ac-AmwTF$r8AYWAQL$S-NH2 | 1618.86 | 810.43 | 810.66 |
| SP-663 | Ac-NmLTF$r8AYWAQL$S-NH2 | 1545.86 | 773.93 | 774.11 |
| SP-664 | Ac-LNmTF$r8AYWAQL$S-NH2 | 1545.86 | 773.93 | 774.11 |
| SP-665 | Ac-LSarF$r8AYWAQL$S-NH2 | 1501.83 | 751.92 | 752.18 |

TABLE 4-continued

| SP | Seq | Exact Mass | M + 2 | Observed mass (m/e) |
|---|---|---|---|---|
| SP-667 | Ac-LGF$r8AYWAQL$S-NH2 | 1487.82 | 744.91 | 745.15 |
| SP-668 | Ac-LTNmF$r8AYWAQL$S-NH2 | 1545.86 | 773.93 | 774.2 |
| SP-669 | Ac-TF$r8AYWAQL$S-NH2 | 1418.76 | 710.38 | 710.64 |
| SP-670 | Ac-ETF$r8AYWAQL$A-NH2 | 1531.81 | 766.91 | 767.2 |
| SP-671 | Ac-LTF$r8EYWAQL$A-NH2 | 1573.85 | 787.93 | 788.1 |
| SP-672 | Ac-LT2Nal$r8AYWSQL$S-NH2 | 1597.85 | 799.93 | 800.4 |
| SP-673 | Ac-LTF$r8AYWAAL$S-NH2 | 1474.82 | 738.41 | 738.68 |
| SP-674 | Ac-LTF$r8AYWAQhCha$S-NH2 | 1585.89 | 793.95 | 794.19 |
| SP-675 | Ac-LTF$r8AYWAQChg$S-NH2 | 1557.86 | 779.93 | 780.97 |
| SP-676 | Ac-LTF$r8AYWAQCba$S-NH2 | 1543.84 | 772.92 | 773.19 |
| SP-677 | Ac-LTF$r8AYWAQF3CF3$S-NH2 | 1633.82 | 817.91 | 818.15 |
| SP-678 | Ac-LTF$r8AYWAQ1Nal$S-NH2 | 1615.84 | 808.92 | 809.18 |
| SP-679 | Ac-LTF$r8AYWAQBip$S-NH2 | 1641.86 | 821.93 | 822.32 |
| SP-680 | Ac-LT2Nal$r8AYWAQL$S-NH2 | 1581.86 | 791.93 | 792.15 |
| SP-681 | Ac-LTF$r8AYWVQL$S-NH2 | 1559.88 | 780.94 | 781.62 |
| SP-682 | Ac-LTF$r8AWWAQL$S-NH2 | 1554.86 | 778.43 | 778.65 |
| SP-683 | Ac-FTF$r8VYWSQL$S-NH2 | 1609.85 | 805.93 | 806.12 |
| SP-684 | Ac-ITF$r8FYWAQL$S-NH2 | 1607.88 | 804.94 | 805.2 |
| SP-685 | Ac-ITF$r8LYWSQL$S-NH2 | 1589.89 | 795.95 | 796.22 |
| SP-686 | Ac-FTF$r8FYWAQL$S-NH2 | 1641.86 | 821.93 | 822.41 |
| SP-687 | Ac-VTF$r8AYWSQL$S-NH2 | 1533.82 | 767.91 | 768.19 |
| SP-688 | Ac-LTF$r8AHWAQL$S-NH2 | 1505.84 | 753.92 | 754.31 |
| SP-689 | Ac-LTF$r8AYWAQL$H-NH2 | 1581.87 | 791.94 | 791.94 |
| SP-690 | Ac-LTF$r8AYWAHL$S-NH2 | 1540.84 | 771.42 | 771.61 |
| SP-691 | Ac-aAibWTF$r8VYWSQL$S-NH2 | 1804.96 | 903.48 | 903.9 |
| SP-692 | Ac-AibWTF$r8HYWAQL$S-NH2 | 1755.91 | 878.96 | 879.5 |
| SP-693 | Ac-AibAWTF$r8HYWAQL$S-NH2 | 1826.95 | 914.48 | 914.7 |
| SP-694 | Ac-fWTF$r8HYWAQL$S-NH2 | 1817.93 | 909.97 | 910.2 |
| SP-695 | Ac-AibWWTF$r8HYWAQL$S-NH2 | 1941.99 | 972.00 | 972.7 |
| SP-696 | Ac-WTF$r8LYWSQL$S-NH2 | 1662.88 | 832.44 | 832.7 |
| SP-697 | Ac-WTF$r8NleYWSQL$S-NH2 | 1662.88 | 832.44 | 832.7 |
| SP-698 | Ac-LTF$r8AYWSQL$a-NH2 | 1531.84 | 766.92 | 767.2 |
| SP-699 | Ac-LTF$r8EYWARL$A-NH2 | 1601.90 | 801.95 | 802.2 |
| SP-700 | Ac-LTF$r8EYWAHL$A-NH2 | 1582.86 | 792.43 | 792.6 |
| SP-701 | Ac-aTF$r8AYWAQL$S-NH2 | 1489.80 | 745.90 | 746.1 |
| SP-702 | Ac-AibTF$r8AYWAQL$S-NH2 | 1503.81 | 752.91 | 753.2 |
| SP-703 | Ac-AmfTF$r8AYWAQL$S-NH2 | 1579.84 | 790.92 | 791.2 |
| SP-704 | Ac-AmwTF$r8AYWAQL$S-NH2 | 1618.86 | 810.43 | 810.7 |

TABLE 4-continued

| SP | Seq | Exact Mass | M + 2 | Observed mass (m/e) |
|---|---|---|---|---|
| SP-705 | Ac-NmLTF$r8AYWAQL$S-NH2 | 1545.86 | 773.93 | 774.1 |
| SP-706 | Ac-LNmTF$r8AYWAQL$S-NH2 | 1545.86 | 773.93 | 774.4 |
| SP-707 | Ac-LSarF$r8AYWAQL$S-NH2 | 1501.83 | 751.92 | 752.1 |
| SP-708 | Ac-TF$r8AYWAQL$S-NH2 | 1418.76 | 710.38 | 710.8 |
| SP-709 | Ac-ETF$r8AYWAQL$A-NH2 | 1531.81 | 766.91 | 767.4 |
| SP-710 | Ac-LTF$r8EYWAQL$A-NH2 | 1573.85 | 787.93 | 788.2 |
| SP-711 | Ac-WTF$r8VYWSQL$S-NH2 | 1648.87 | 825.44 | 825.2 |
| SP-713 | Ac-YTF$r8FYWSQL$S-NH2 | 1673.85 | 837.93 | 837.3 |
| SP-714 | Ac-F$r8AY6cIWSAL$A-NH2 | 1294.65 | 648.33 | 647.74 |
| SP-715 | Ac-ETF$r8EYWVQL$S-NH2 | 1633.84 | 817.92 | 817.36 |
| SP-716 | Ac-ETF$r8EHWAQL$A-NH2 | 1563.81 | 782.91 | 782.36 |
| SP-717 | Ac-ITF$r8EYWAQL$S-NH2 | 1589.85 | 795.93 | 795.38 |
| SP-718 | Ac-ITF$r8EHWVQL$A-NH2 | 1575.88 | 788.94 | 788.42 |
| SP-719 | Ac-ITF$r8EHWAQL$S-NH2 | 1563.85 | 782.93 | 782.43 |
| SP-720 | Ac-LTF4F$r8AYWAQCba$S-NH2 | 1561.83 | 781.92 | 781.32 |
| SP-721 | Ac-LTF3CI$r8AYWAQhL$S-NH2 | 1579.82 | 790.91 | 790.64 |
| SP-722 | Ac-LTF3CI$r8AYWAQCha$S-NH2 | 1605.84 | 803.92 | 803.37 |
| SP-723 | Ac-LTF3CI$r8AYWAQChg$S-NH2 | 1591.82 | 796.91 | 796.27 |
| SP-724 | Ac-LTF3CI$r8AYWAQCba$S-NH2 | 1577.81 | 789.91 | 789.83 |
| SP-725 | Ac-LTF$r8AY6cIWSQL$S-NH2 | 1581.80 | 791.90 | 791.75 |
| SP-726 | Ac-LTF4F$r8HYWAQhL$S-NH2 | 1629.87 | 815.94 | 815.36 |
| SP-727 | Ac-LTF4F$r8HYWAQCba$S-NH2 | 1627.86 | 814.93 | 814.32 |
| SP-728 | Ac-LTF4F$r8AYWAQhL$S-NH2 | 1563.85 | 782.93 | 782.36 |
| SP-729 | Ac-LTF4F$r8AYWAQChg$S-NH2 | 1575.85 | 788.93 | 788.35 |
| SP-730 | Ac-ETF$r8EYWVAL$S-NH2 | 1576.82 | 789.41 | 788.79 |
| SP-731 | Ac-ETF$r8EHWAAL$A-NH2 | 1506.79 | 754.40 | 754.8 |
| SP-732 | Ac-ITF$r8EYWAAL$S-NH2 | 1532.83 | 767.42 | 767.75 |
| SP-733 | Ac-ITF$r8EHWVAL$A-NH2 | 1518.86 | 760.43 | 760.81 |
| SP-734 | Ac-ITF$r8EHWAAL$S-NH2 | 1506.82 | 754.41 | 754.8 |
| SP-735 | Pam-LTF$r8EYWAQL$S-NH2 | 1786.07 | 894.04 | 894.48 |
| SP-736 | Pam-ETF$r8EYWAQL$S-NH2 | 1802.03 | 902.02 | 902.34 |
| SP-737 | Ac-LTF$r8AYWLQL$S-NH2 | 1573.89 | 787.95 | 787.39 |
| SP-738 | Ac-LTF$r8EYWLQL$S-NH2 | 1631.90 | 816.95 | 817.33 |
| SP-739 | Ac-LTF$r8EHWLQL$S-NH2 | 1605.89 | 803.95 | 804.29 |
| SP-740 | Ac-LTF$r8VYWAQL$S-NH2 | 1559.88 | 780.94 | 781.34 |
| SP-741 | Ac-LTF$r8AYWSQL$S-NH2 | 1547.84 | 774.92 | 775.33 |
| SP-742 | Ac-ETF$r8AYWAQL$S-NH2 | 1547.80 | 774.90 | 775.7 |
| SP-743 | Ac-LTF$r8EYWAQL$S-NH2 | 1589.85 | 795.93 | 796.33 |

TABLE 4-continued

| SP | Seq | Exact Mass | M + 2 | Observed mass (m/e) |
|---|---|---|---|---|
| SP-744 | Ac-LTF$r8HYWAQL$S-NHAm | 1667.94 | 834.97 | 835.37 |
| SP-745 | Ac-LTF$r8HYWAQL$S-NHiAm | 1667.94 | 834.97 | 835.27 |
| SP-746 | Ac-LTF$r8HYWAQL$S-NHnPr3Ph | 1715.94 | 858.97 | 859.42 |
| SP-747 | Ac-LTF$r8HYWAQL$S-NHnBu3,3Me | 1681.96 | 841.98 | 842.67 |
| SP-748 | Ac-LTF$r8HYWAQL$S-NHnBu | 1653.93 | 827.97 | 828.24 |
| SP-749 | Ac-LTF$r8HYWAQL$S-NHnPr | 1639.91 | 820.96 | 821.31 |
| SP-750 | Ac-LTF$r8HYWAQL$S-NHnEt2Ch | 1707.98 | 854.99 | 855.35 |
| SP-751 | Ac-LTF$r8HYWAQL$S-NHHex | 1681.96 | 841.98 | 842.4 |
| SP-752 | Ac-LTF$r8AYWAQL$S-NHmdPeg2 | 1633.91 | 817.96 | 855.35 |
| SP-753 | Ac-LTF$r8AYWAQL$A-NHmdPeg2 | 1617.92 | 809.96 | 810.58 |
| SP-754 | Ac-LTF$r5AYWAAL$s8S-NH2 | 1474.82 | 738.41 | 738.79 |
| SP-755 | Ac-LTF$r8AYWCouQL$S-NH2 | 1705.88 | 853.94 | 854.61 |
| SP-756 | Ac-LTF$r8CouYWAQL$S-NH2 | 1705.88 | 853.94 | 854.7 |
| SP-757 | Ac-CouTF$r8AYWAQL$S-NH2 | 1663.83 | 832.92 | 833.33 |
| SP-758 | H-LTF$r8AYWAQL$A-NH2 | 1473.84 | 737.92 | 737.29 |
| SP-759 | Ac-HHF$r8AYWAQL$S-NH2 | 1591.83 | 796.92 | 797.72 |
| SP-760 | Ac-LT2Nal$r8AYWSQL$S-NH2 | 1597.85 | 799.93 | 800.68 |
| SP-761 | Ac-LTF$r8HCouWAQL$S-NH2 | 1679.87 | 840.94 | 841.38 |
| SP-762 | Ac-LTF$r8AYWCou2QL$S-NH2 | 1789.94 | 895.97 | 896.51 |
| SP-763 | Ac-LTF$r8Cou2YWAQL$S-NH2 | 1789.94 | 895.97 | 896.5 |
| SP-764 | Ac-Cou2TF$r8AYWAQL$S-NH2 | 1747.90 | 874.95 | 875.42 |
| SP-765 | Ac-LTF$r8ACou2WAQL$S-NH2 | 1697.92 | 849.96 | 850.82 |
| SP-766 | Dmaac-LTF$r8AYWAQL$S-NH2 | 1574.89 | 788.45 | 788.82 |
| SP-767 | Hexac-LTF$r8AYWAQL$S-NH2 | 1587.91 | 794.96 | 795.11 |
| SP-768 | Napac-LTF$r8AYWAQL$S-NH2 | 1657.89 | 829.95 | 830.36 |
| SP-769 | Pam-LTF$r8AYWAQL$S-NH2 | 1728.06 | 865.03 | 865.45 |
| SP-770 | Ac-LT2Nal$r8HYAAQL$S-NH2 | 1532.84 | 767.42 | 767.61 |
| SP-771 | Ac-LT2Nal$/r8HYWAQL$/S-NH2 | 1675.91 | 838.96 | 839.1 |
| SP-772 | Ac-LT2Nal$r8HYFAQL$S-NH2 | 1608.87 | 805.44 | 805.9 |
| SP-773 | Ac-LT2Nal$r8HWAAQL$S-NH2 | 1555.86 | 778.93 | 779.08 |
| SP-774 | Ac-LT2Nal$r8HYAWQL$S-NH2 | 1647.88 | 824.94 | 825.04 |
| SP-775 | Ac-LT2Nal$r8HYAAQW$S-NH2 | 1605.83 | 803.92 | 804.05 |
| SP-776 | Ac-LTW$r8HYWAQL$S-NH2 | 1636.88 | 819.44 | 819.95 |
| SP-777 | Ac-LT1Nal$r8HYWAQL$S-NH2 | 1647.88 | 824.94 | 825.41 |

In the sequences shown above and elsewhere, the following abbreviations are used: "Nle" represents norleucine, "Aib" represents 2-aminoisobutyric acid, "Ac" represents acetyl, and "Pr" represents propionyl. Amino acids represented as "$" are alpha-Me S5-pentenyl-alanine olefin amino acids connected by an all-carbon i to i+4 crosslinker comprising one double bond. Amino acids represented as "$r5" are alpha-Me R5-pentenyl-alanine olefin amino acids connected by an all-carbon i to i+4 crosslinker comprising one double bond. Amino acids represented as "$s8" are alpha-Me S8-octenyl-alanine olefin amino acids connected by an all-carbon i to i+7 crosslinker comprising one double bond. Amino acids represented as "$r8" are alpha-Me R8-octenyl-alanine olefin amino acids connected by an all-carbon i to i+7 crosslinker comprising one double bond. "Ahx" represents an aminocyclohexyl linker. The crosslinkers are linear all-carbon crosslinker comprising eight or eleven carbon atoms between the alpha carbons of each amino acid. Amino acids represented as "$/" are alpha-Me S5-pentenyl-alanine olefin amino acids that are not connected by any crosslinker. Amino acids represented as "$/r5" are alpha-Me R5-pentenyl-alanine olefin amino acids that are not connected by any crosslinker. Amino acids represented as "$/s8" are alpha-Me S8-octenyl-alanine olefin amino acids that are not connected by any crosslinker. Amino acids represented as "$/r8" are alpha-Me R8-octenyl-alanine olefin amino acids that are not connected by any crosslinker. Amino acids represented as "Amw" are alpha-Me tryptophan amino acids. Amino acids represented as "Aml" are alpha-Me leucine amino acids. Amino acids represented as "2ff" are 2-fluoro-phenylalanine amino acids. Amino acids represented as "3ff" are 3-fluoro-phenylalanine amino acids. Amino acids represented as "St" are amino acids comprising two pentenyl-alanine olefin side chains, each of which is crosslinked to another amino acid as indicated. Amino acids represented as "St//" are amino acids comprising two pentenyl-alanine olefin side chains that are not crosslinked. Amino acids represented as "% St" are amino acids comprising two pentenyl-alanine olefin side chains, each of which is crosslinked to another amino acid as indicated via fully saturated hydrocarbon crosslinks.

For example, the compounds represented as SP-72, SP-56 and SP-138 have the following structures:

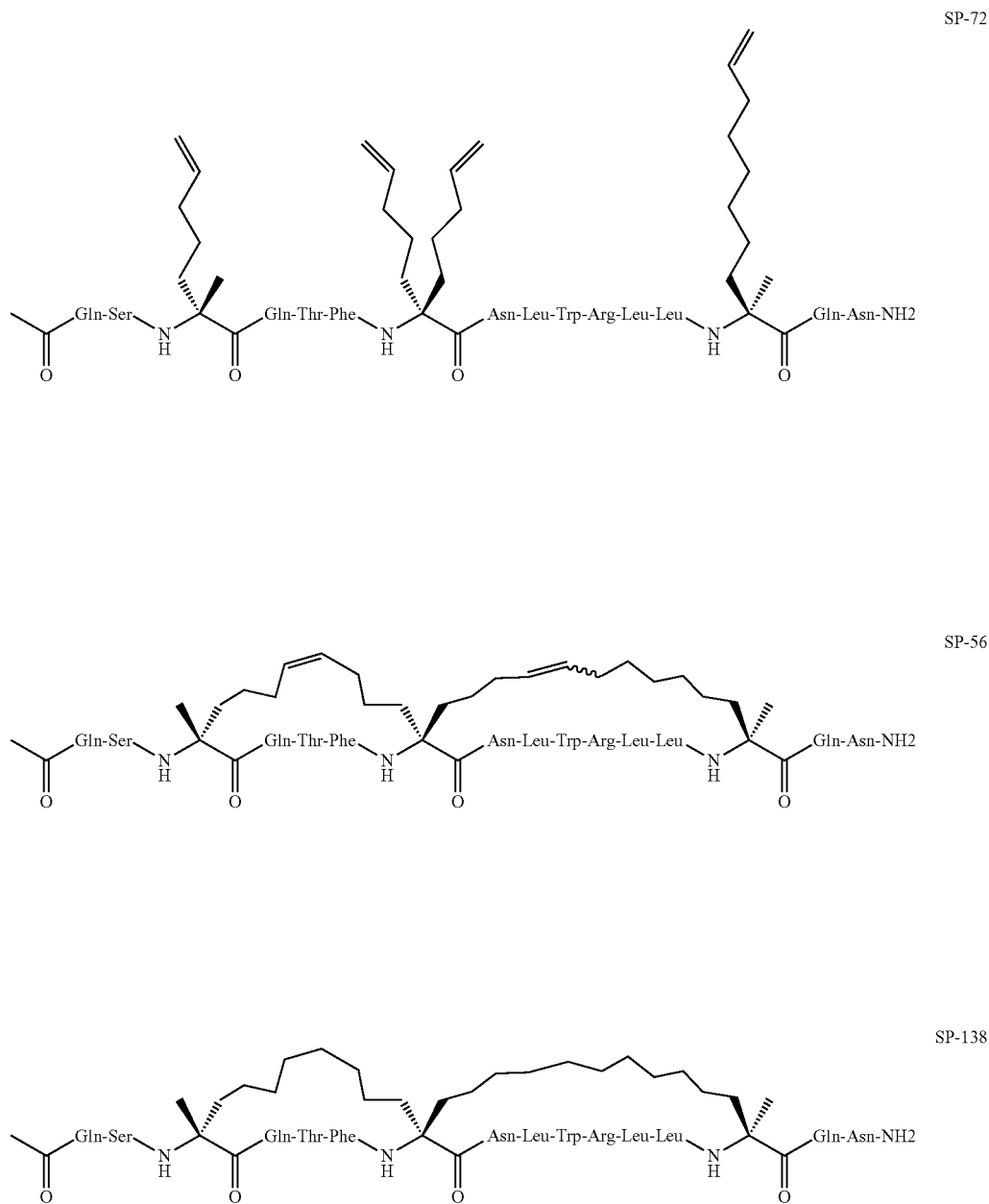

For example, additional compounds have the following structures:
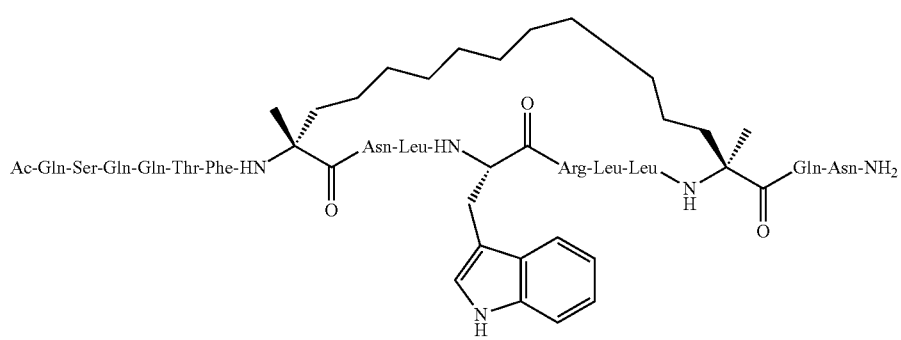
SP-46
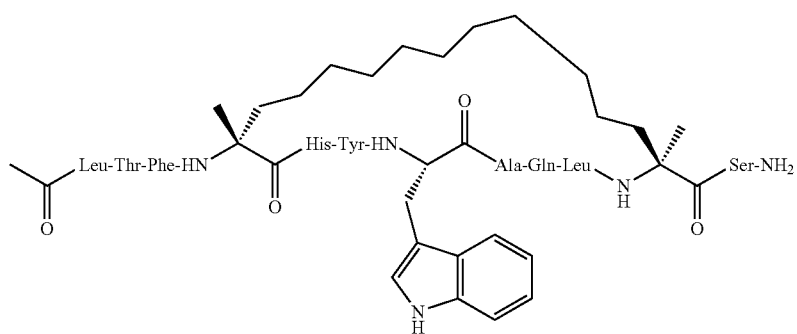
SP-142
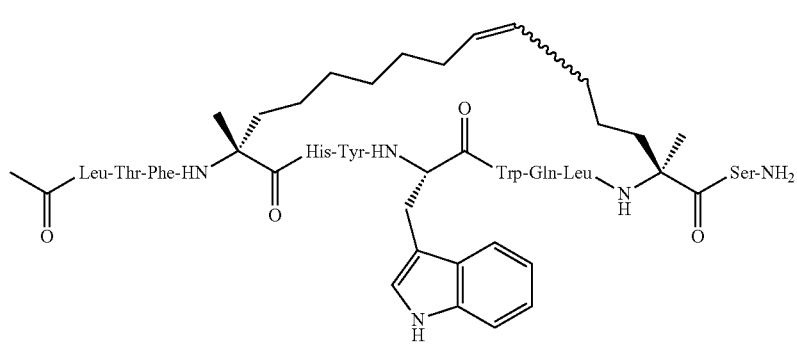
SP-280
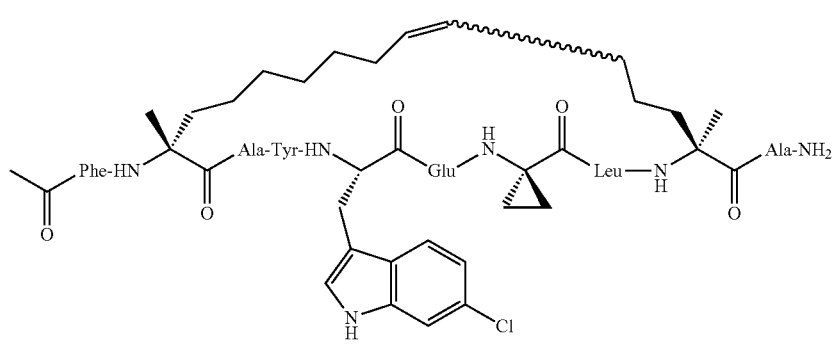
SP-128

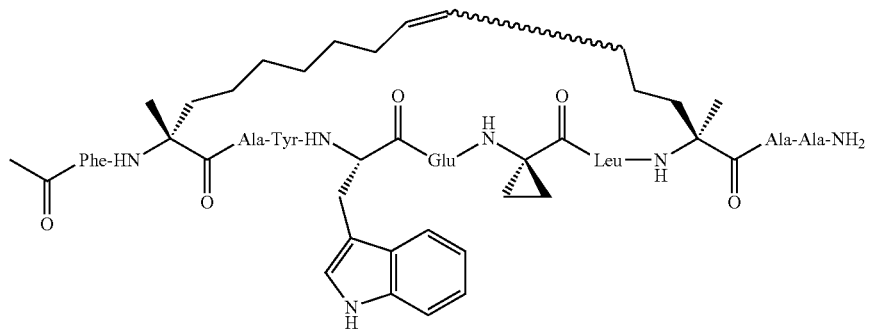
SP-201
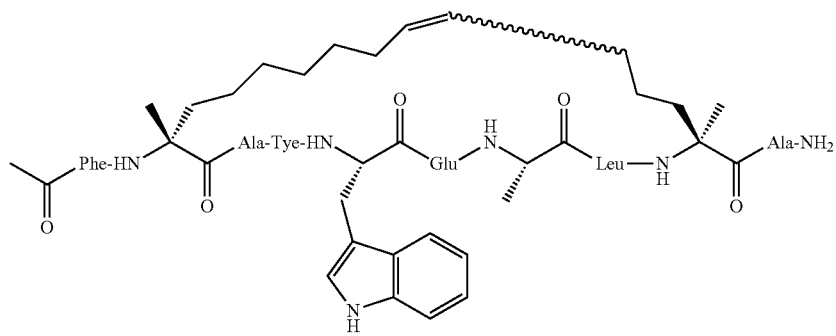
SP-250
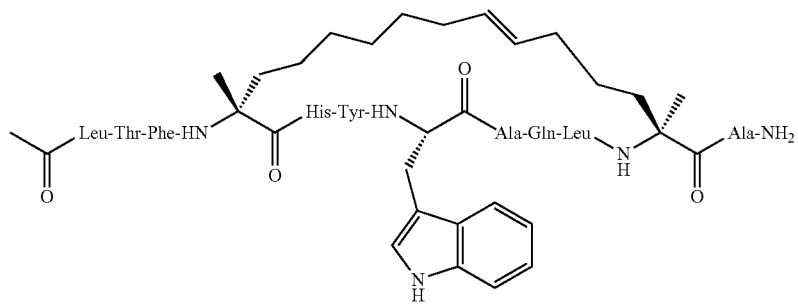
SP-343
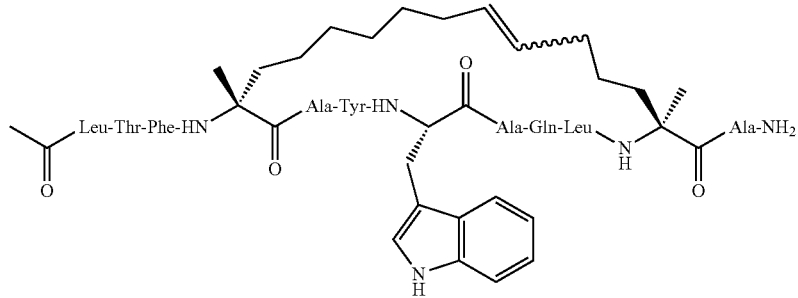
SP-193
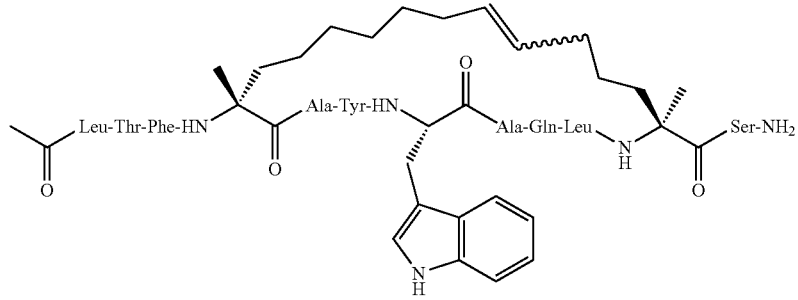
SP-190

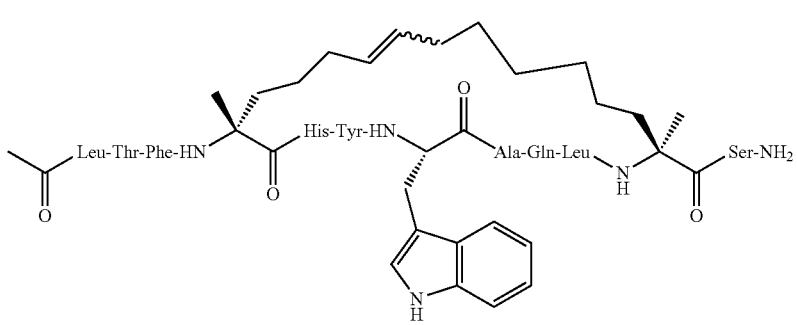

SP-364

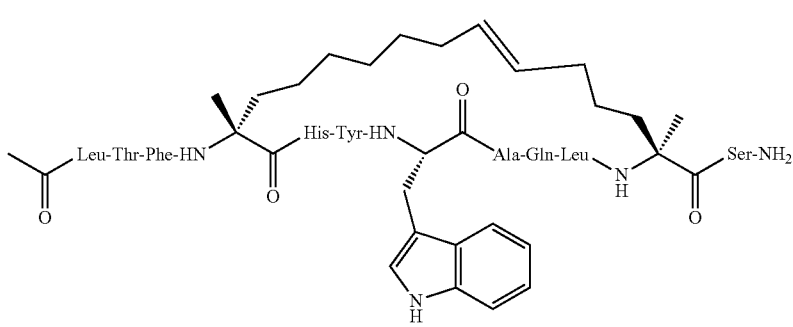

SP-156

Example 3: Competition Binding ELISA (HDM2 & HDMX)

p53-His6 protein (30 nM/well) is coated overnight at room temperature in the wells of a 96-well Immulon plates. On the day of the experiment, plates are washed with 1×PBS-Tween 20 (0.05%) using an automated ELISA plate washer, blocked with ELISA Micro well Blocking for 30 minutes at room temperature; excess blocking agent is washed off by washing plates with 1×PBS-Tween 20 (0.05%). Peptides are diluted from 10 mM DMSO stocks to 500 µM working stocks in sterile water, further dilutions made in 0.5% DMSO to keep the concentration of DMSO constant across the samples. The peptides are added to wells at 2× desired concentrations in 50 µl volumes, followed by addition of diluted GST-HDM2 or GST-HMDX protein (final concentration: 10 nM). Samples are incubated at room temperature for 2 h, plates are washed with PBS-Tween 20 (0.05%) prior to adding 100 µl of HRP-conjugated anti-GST antibody [Hypromatrix, INC] diluted to 0.5 µg/ml in HRP-stabilizing buffer. Post 30 min incubation with detection antibody, plates are washed and incubated with 100 µl per well of TMB-E Substrate solution up to 30 minutes; reactions are stopped using 1M HCL and absorbance measured at 450 nm on micro plate reader. Data is analyzed using Graph Pad PRISM software.

Example 4: SJSA-1 Cell Viability Assay

SJSA1 cells are seeded at the density of 5000 cells/100 µl/well in 96-well plates a day prior to assay. On the day of study cells are washed once with Opti-MEM Media and 90 µL of the Opti-MEM Media is added to cells. Peptides are diluted from 10 mM DMSO stocks to 500 µM working stocks in sterile water, further dilutions made in 0.5% DMSO to keep the concentration of DMSO constant across the samples. The final concentration range µM will be 50, 25, 12.5, 6.25, 3.1, 1.56, 0.8 and 0 µM in 100 µL final volume per well for peptides. Final highest DMSO concentration is 0.5% and will be used as the negative control. Cayman Chemicals Cell-Based Assay (−)-Nutlin-3 (10 mM) is used as positive control. Nutlin was diluted using the same dilution scheme as peptides 10 µl of 10× desired concentrations is added to the appropriate well to achieve the final desired concentrations. Cells are then incubated with peptides for 20-24 h at 37° C. in humidified 5% CO2 atmosphere. Post-incubation period, cell viability is measured using Promega Cell Titer-Glo reagents according to manufacturer' instructions.

Example 5: SJSA-1 p21 Up-Regulation Assay

SJSA1 cells are seeded at the density of 0.8 million cells/2 ml/well in 6-well plates a day prior to assay. On the day of study cells are washed once with Opti-MEM Media and 1350 µL of the Opti-MEM Media is added to cells. Peptides are diluted from 10 mM DMSO stocks to 500 µM working stocks in sterile water, further dilutions made in 0.5% DMSO to keep the concentration of DMSO constant across the samples. Final highest DMSO concentration is 0.5% and is used as the negative control. Cayman Chemicals Cell-Based Assay (−)-Nutlin-3 (10 mM) is used as positive control. Nutlin is diluted using the same dilution scheme as peptides 150 µl of 10× desired concentrations is added to the appropriate well to achieve the final desired concentrations. Cells are then incubated with peptides for 18-20 h at 37° C. in humidified 5% CO2 atmosphere. Post-incubation period, cells are harvested, washed with 1×PBS (without Ca++/Mg++) and lysed in 1× Cell lysis buffer (Cell Signaling technologies 10× buffer diluted to 1× and supplemented with protease inhibitors and Phosphatase inhibitors) on ice for 30 min. Lysates are centrifuged at 13000 rpm speed in a microfuge at 40 C for 8 min; clear supernatants are collected and stored at −80° C. till further use. Total protein content of the lysates is measured using BCA protein detection kit and BSA standards from Thermofisher. 25 µg of the total protein is used for p21 detection ELISA assay. Each condition is set in triplicate for ELISA plate. The ELISA assay protocol is followed as per the manufacturer's instructions. 25 μg total protein used for each well, and each well is set up in triplicate. Data is analyzed using Graph Pad PRISM software.

Example 6: p53 GRIP Assay

Thermo Scientific* BioImage p53-Hdm2 Redistribution Assay monitors the protein interaction with Hdm2 and cellular translocation of GFP-tagged p53 in response to drug compounds or other stimuli. Recombinant CHO-hIR cells stably express human p53(1-312) fused to the C-terminus of enhanced green fluorescent protein (EGFP) and PDE4A4-Hdm2(1-124), a fusion protein between PDE4A4 and Hdm2(1-124). They provide a ready-to-use assay system for measuring the effects of experimental conditions on the interaction of p53 and Hdm2. Imaging and analysis is performed with a HCS platform.

CHO-hIR cells are regularly maintained in Ham's F12 media supplemented with 1% Penicillin-Streptomycin, 0.5 mg/ml Geneticin, 1 mg/ml Zeocin and 10% FBS. Cells seeded into 96-well plates at the density of 7000 cells/100 μl per well 18-24 hours prior to running the assay using culture media. The next day, media is refreshed and PD177 is added to cells to the final concentration of 3 μM to activate foci formation. Control wells are kept without PD-177 solution. 24 h post stimulation with PD177, cells are washed once with Opti-MEM Media and 50 μL of the Opti-MEM Media supplemented with PD-177(6 μM) is added to cells. Peptides are diluted from 10 mM DMSO stocks to 500 μM working stocks in sterile water, further dilutions made in 0.5% DMSO to keep the concentration of DMSO constant across the samples. Final highest DMSO concentration is 0.5% and is used as the negative control. Cayman Chemicals Cell-Based Assay (−)-Nutlin-3 (10 mM) is used as positive control. Nutlin was diluted using the same dilution scheme as peptides. 50 μl of 2× desired concentrations is added to the appropriate well to achieve the final desired concentrations. Cells are then incubated with peptides for 6 h at 37° C. in humidified 5% CO2 atmosphere. Post-incubation period, cells are fixed by gently aspirating out the media and adding 150 μl of fixing solution per well for 20 minutes at room temperature. Fixed cells are washed 4 times with 200 μl PBS per well each time. At the end of last wash, 100 μl of 1 μM Hoechst staining solution is added. Sealed plates incubated for at least 30 min in dark, washed with PBS to remove excess stain and PBS is added to each well. Plates can be stored at 4° C. in dark up to 3 days. The translocation of p53/HDM2 is imaged using Molecular translocation module on Cellomics Arrayscan instrument using 10× objective, XF-100 filter sets for Hoechst and GFP. The output parameters was Mean-CircRINGAveIntenRatio (the ratio of average fluorescence intensities of nucleus and cytoplasm, (well average)). The minimally acceptable number of cells per well used for image analysis was set to 500 cells.

Example 7: Direct Binding Assay hDM2 with Fluorescence Polarization (FP)

The assay was performed according to the following general protocol:
1. Dilute hDM2 (In-house, 41 kD) into FP buffer (High salt buffer-200 mM Nacl, 5 mM CHAPS, pH 7.5) to make 10 μM working stock solution.
2. Add 30 μl of 10 μM of protein stock solution into A1 and B1 well of 96-well black HE microplate (Molecular Devices).
3. Fill in 30 μl of FP buffer into column A2 to A12, B2 to B12, C1 to C12, and D1 to D12.
4. 2 or 3 fold series dilution of protein stock from A1, B1 into A2, B2; A2, B2 to A3, B3; . . . to reach the single digit nM concentration at the last dilution point.
5. Dilute 1 mM (in 100% DMSO) of FAM labeled linear peptide with DMSO to 100 μM (dilution 1:10). Then, dilute from 100 μM to 10 μM with water (dilution 1:10) and then dilute with FP buffer from 10 μM to 40 nM (dilution 1:250). This is the working solution which will be a 10 nM concentration in well (dilution 1:4). Keep the diluted FAM labeled peptide in the dark until use.
6. Add 10 μl of 10 nM of FAM labeled peptide into each well and incubate, and read at different time points. Kd with 5-FAM-BaLTFEHYWAQLTS-NH$_2$ is ~13.38 nM.

Example 8: Competitive Fluorescence Polarization Assay for hDM2

The assay was performed according to the following general protocol:
1. Dilute hDM2 (In-house, 41 kD) into FP buffer (High salt buffer-200 mM Nacl, 5 mM CHAPS, pH 7.5) to make 84 nM (2×) working stock solution.
2. Add 20 μl of 84 nM (2×) of protein stock solution into each well of 96-well black HE microplate (Molecular Devices)
3. Dilute 1 mM (in 100% DMSO) of FAM labeled linear peptide with DMSO to 100 μM (dilution 1:10). Then, dilute from 100 μM to 10 μM with water (dilution 1:10) and then dilute with FP buffer from 10 μM to 40 nM (dilution 1:250). This is the working solution which will be a 10 nM concentration in well (dilution 1:4). Keep the diluted FAM labeled peptide in the dark until use.
4. Make unlabeled peptide dose plate with FP buffer starting with 1 μM (final) of peptide and making 5 fold serial dilutions for 6 points using following dilution scheme.
Dilute 10 mM (in 100% DMSO) with DMSO to 5 mM (dilution 1:2). Then, dilute from 5 mM to 500 μM with H$_2$O (dilution 1:10) and then dilute with FP buffer from 500 μM to 20 μM (dilution 1:25). Making 5 fold serial dilutions from 4 μM (4×) for 6 points.
5. Transfer 10 μl of serial diluted unlabeled peptides to each well which is filled with 20 μl of 84 nM of protein.
6. Add 10 μl of 10 nM (4×) of FAM labeled peptide into each well and incubate for 3 hr to read.
Results of Examples 7 and 8 are provided in HDM2 data in FIGS. 7A-D.

Example 9: Direct Binding Assay hDMX with Fluorescence Polarization (FP)

The assay was performed according to the following general protocol:
1. Dilute hDMX (In-house, 40 kD) into FP buffer (High salt buffer-200 mM Nacl, 5 mM CHAPS, pH 7.5) to make 10 μM working stock solution.
2. Add 30 μl of 10 μM of protein stock solution into A1 and B1 well of 96-well black HE microplate (Molecular Devices).

3. Fill in 30l of FP buffer into column A2 to A12, B2 to B12, C1 to C12, and D1 to D12.
4. 2 or 3 fold series dilution of protein stock from A1, B1 into A2, B2; A2, B2 to A3, B3; . . . to reach the single digit nM concentration at the last dilution point.
5. Dilute 1 mM (in 100% DMSO) of FAM labeled linear peptide with DMSO to 100 µM (dilution 1:10). Then, dilute from 100 µM to 10 µM with water (dilution 1:10) and then dilute with FP buffer from 10 µM to 40 nM (dilution 1:250). This is the working solution which will be a 10 nM concentration in well (dilution 1:4). Keep the diluted FAM labeled peptide in the dark until use.
6. Add 10 µl of 10 nM of FAM labeled peptide into each well and incubate, and read at different time points. Kd with 5-FAM-BaLTFEHYWAQLTS-NH$_2$ is ~51 nM.

Example 10: Competitive Fluorescence Polarization Assay for hDMX

The assay was performed according to the following general protocol:
1. Dilute hDMX (In-house, 40 kD) into FP buffer (High salt buffer-200 mM Nacl, 5 mM CHAPS, pH 7.5.) to make 300 nM (2×) working stock solution.
2. Add 20 µl of 300 nM (2×) of protein stock solution into each well of 96-well black HE microplate (Molecular Devices)
3. Dilute 1 mM (in 100% DMSO) of FAM labeled linear peptide with DMSO to 100 µM (dilution 1:10). Then, dilute from 100 µM to 10 µM with water (dilution 1:10) and then dilute with FP buffer from 10M to 40 nM (dilution 1:250). This is the working solution which will be a 10 nM concentration in well (dilution 1:4). Keep the diluted FAM labeled peptide in the dark until use.
4. Make unlabeled peptide dose plate with FP buffer starting with 5 µM (final) of peptide and making 5 fold serial dilutions for 6 points using following dilution scheme.
5. Dilute 10 mM (in 100% DMSO) with DMSO to 5 mM (dilution 1:2). Then, dilute from 5 mM to 500 µM with H$_2$O (dilution 1:10) and then dilute with FP buffer from 500 µM to 20 µM (dilution 1:25). Making 5 fold serial dilutions from 20 µM (4×) for 6 points.
6. Transfer 10 µl of serial diluted unlabeled peptides to each well which is filled with 20 µl of 300 nM of protein.
7. Add 10 µl of 10 nM (4×) of FAM labeled peptide into each well and incubate for 3 hr to read.

Results of Examples 9 and 10 are provided in HDMX data in FIGS. 7A-D.

Example 11: Cell Viability Assay

The assay was performed according to the following general protocol:

Cell Plating: Trypsinize, count and seed cells at the pre-determined densities in 96-well plates a day prior to assay. Following cell densities are used for each cell line in use:
SJSA-1: 7500 cells/well
RKO: 5000 cells/well
RKO-E6: 5000 cells/well
HCT-116: 5000 cells/well
SW-480: 2000 cells/well
MCF-7: 5000 cells/well On the day of study, replace media with fresh media with 11% FBS (assay media) at room temperature. Add 180 µL of the assay media per well. Control wells with no cells, receive 200 µl media.

Peptide dilution: all dilutions are made at room temperature and added to cells at room temperature.

Prepare 10 mM stocks of the peptides in DMSO. Serially dilute the stock using 1:3 dilution scheme to get 10, 3.3, 1.1, 0.33, 0.11, 0.03, 0.01 mM solutions using DMSO as diluents. Dilute the serially DMSO-diluted peptides 33.3 times using sterile water. This gives range of 10× working stocks. Also prepare DMSO/sterile water (3% DMSO) mix for control wells.

Thus the working stocks concentration range µM will be 300, 100, 30, 10, 3, 1, 0.3 and 0 µM. Mix well at each dilution step using multichannel.

Row H has controls. H1-H3 will receive 20 ul of assay media. H4-H9 will receive 20 ul of 3% DMSO-water vehicle. H10-H12 will have media alone control with no cells.

Positive control: HDM2 small molecule inhibitor, Nutlin-3a (10 mM) is used as positive control. Nutlin was diluted using the same dilution scheme as peptides.

Addition of working stocks to cells:

Add 20 µl of 10× desired concentration to appropriate well to achieve the final concentrations in total 200 µl volume in well. (20 µl of 300 µM peptide+180 µl of cells in media=30 µM final concentration in 200 µl volume in wells). Mix gently a few times using pipette. Thus final concentration range used will be 30, 10, 3, 1, 0.3, 0.1, 0.03 & 0 µM (for potent peptides further dilutions are included).

Controls include wells that get no peptides but contain the same concentration of DMSO as the wells containing the peptides, and wells containing NO CELLS.

Incubate for 72 hours at 37° C. in humidified 5% CO$_2$ atmosphere.

The viability of cells is determined using MTT reagent from Promega. Viability of SJSA-1, RKO, RKO-E6, HCT-116 cells is determined on day 3, MCF-7 cells on day 5 and SW-480 cells on day 6. At the end of designated incubation time, allow the plates to come to room temperature. Remove 80 µl of assay media from each well. Add 15 µl of thawed MTT reagent to each well.

Allow plate to incubate for 2 h at 37° C. in humidified 5% CO$_2$ atmosphere and add 100 µl solubilization reagent as per manufacturer's protocol. Incubate with agitation for 1 h at room temperature and read on Synergy Biotek multiplate reader for absorbance at 570 nM.

Analyze the cell viability against the DMSO controls using GraphPad PRISM analysis tools.

Reagents:

Invitrogen cell culture Media
  i. Falcon 96-well clear cell culture treated plates (Nunc 353072)
DMSO (Sigma D 2650)
RPMI 1640 (Invitrogen 72400)
MTT (Promega G4000)
Instruments:
Multiplate Reader for Absorbance readout (Synergy 2)

Results of Example 11 are provided in SJSA-1 EC50 data in FIGS. 7A-D.

Example 12. P21 ELISA Assay

The assay was performed according to the following general protocol:

Cell Plating:
Trypsinize, count and seed SJSA1 cells at the density of 7500 cells/100 μl/well in 96-well plates a day prior to assay.

On the day of study, replace media with fresh RPMI-11% FBS (assay media). Add 90 μL of the assay media per well. Control wells with no cells, receive 100 μl media.

Peptide Dilution:
Prepare 10 mM stocks of the peptides in DMSO. Serially dilute the stock using 1:3 dilution scheme to get 10, 3.3, 1.1, 0.33, 0.11, 0.03, 0.01 mM solutions using DMSO as diluents. Dilute the serially DMSO-diluted peptides 33.3 times using sterile water This gives range of 10× working stocks. Also prepare DMSO/sterile water (3% DMSO) mix for control wells.

Thus the working stocks concentration range μM will be 300, 100, 30, 10, 3, 1, 0.3 and 0 μM. Mix well at each dilution step using multichannel.

Row H has controls. H1-H3 will receive 10 ul of assay media. H4-H9 will receive 10 ul of 3% DMSO-water vehicle. H10-H12 will have media alone control with no cells.

Positive control: HDM2 small molecule inhibitor, Nutlin-3a (10 mM) is used as positive control. Nutlin was diluted using the same dilution scheme as peptides.

Addition of Working Stocks to Cells:
Add 10 μl of 10× desired concentration to appropriate well to achieve the final concentrations in total 100 μl volume in well. (10 μl of 300 μM peptide+90 μl of cells in media=30 μM final concentration in 100 μl volume in wells). Thus final concentration range used will be 30, 10, 3, 1, 0.3 & 0 μM.

Controls will include wells that get no peptides but contain the same concentration of DMSO as the wells containing the peptides, and wells containing NO CELLS.

20 h-post incubation, aspirate the media; wash cells with 1×PBS (without $Ca^{++}/Mg^{++}$) and lyse in 60 μl of 1× Cell lysis buffer (Cell Signaling technologies 10× buffer diluted to 1× and supplemented with protease inhibitors and Phosphatase inhibitors) on ice for 30 min.

Centrifuge plates in at 5000 rpm speed in at 4° C. for 8 min; collect clear supernatants and freeze at −80° C. till further use.

Protein Estimation:
Total protein content of the lysates is measured using BCA protein detection kit and BSA standards from Thermofisher. Typically about 6-7 μg protein is expected per well.

Use 50 μl of the lysate per well to set up p21 ELISA.

Human Total p21 ELISA:
The ELISA assay protocol is followed as per the manufacturer's instructions. 50 μl lysate is used for each well, and each well is set up in triplicate.

Reagents:
Cell-Based Assay (−)-Nutlin-3 (10 mM): Cayman Chemicals, catalog #600034
OptiMEM, Invitrogen catalog #51985
Cell Signaling Lysis Buffer (10×), Cell signaling technology, Catalog #9803
Protease inhibitor Cocktail tablets (mini), Roche Chemicals, catalog #04693124001
Phosphatase inhibitor Cocktail tablet, Roche Chemicals, catalog #04906837001
Human total p21 ELISA kit, R&D Systems, DYC1047-5
STOP Solution (1M HCL), Cell Signaling Technologies, Catalog #7002

Instruments: Micro centrifuge—Eppendorf 5415D and Multiplate Reader for Absorbance readout (Synergy 2)

Results of Example 12 are provided in p21 data in FIGS. 7A-D.

Example 13: Caspase 3 Detection Assay

The assay was performed according to the following general protocol:

Cell Plating: Trypsinize, count and seed SJSA1 cells at the density of 7500 cells/100 μl/well in 96-well plates a day prior to assay. On the day of study, replace media with fresh RPMI-11% FBS (assay media). Add 180 μL of the assay media per well. Control wells with no cells, receive 200 μl media.

Peptide Dilution:
Prepare 10 mM stocks of the peptides in DMSO. Serially dilute the stock using 1:3 dilution scheme to get 10, 3.3, 1.1, 0.33, 0.11, 0.03, 0.01 mM solutions using DMSO as diluents. Dilute the serially DMSO-diluted peptides 33.3 times using sterile water This gives range of 10× working stocks. Also prepare DMSO/sterile water (3% DMSO) mix for control wells.

Thus the working stocks concentration range μM will be 300, 100, 30, 10, 3, 1, 0.3 and 0 μM. Mix well at each dilution step using multichannel. Add 20 ul of 10× working stocks to appropriate wells.

Row H has controls. H1-H3 will receive 20 ul of assay media. H4-H9 will receive 20 ul of 3% DMSO-water vehicle. H10-H12 will have media alone control with no cells.

Positive control: HDM2 small molecule inhibitor, Nutlin-3a (10 mM) is used as positive control. Nutlin was diluted using the same dilution scheme as peptides.

Addition of Working Stocks to Cells:
Add 10 μl of 10× desired concentration to appropriate well to achieve the final concentrations in total 100 μl volume in well. (10 μl of 300 μM peptide+90 μl of cells in media=30 μM final concentration in 100 μl volume in wells). Thus final concentration range used will be 30, 10, 3, 1, 0.3 & 0 μM.

Controls will include wells that get no peptides but contain the same concentration of DMSO as the wells containing the peptides, and wells containing NO CELLS.

48 h-post incubation, aspirate 80 μl media from each well; add 100 μl Caspase3/7Glo assay reagent (Promega Caspase 3/7 glo assay system, G8092) per well, incubate with gentle shaking for 1 h at room temperature.

read on Synergy Biotek multiplate reader for luminescence.

Data is analyzed as Caspase 3 activation over DMSO-treated cells.

Results of Example 13 are provided in p21 data in FIGS. 7A-D.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11008366B2). An electronic copy of the "Sequence Listing" will also be available from the USPTO upon request and payment of the fee set forth in 37 CFR 1.19(b)(3).

What is claimed is:

1. A method of treating neutropenia, thrombocytopenia, or anemia in a subject, the method comprising administering an effective amount of a peptidomimetic macrocycle to the subject, wherein the peptidomimetic macrocycle comprises an amino acid sequence that is at least 80% identical to SEQ ID NO: 760.

2. The method of claim 1, wherein the peptidomimetic macrocycle comprises an amino acid sequence which is at least 90% identical to SEQ ID NO: 760.

3. The method of claim 1, wherein the peptidomimetic macrocycle comprises an amino acid sequence which is SEQ ID NO: 760.

4. The method of claim 1, wherein the peptidomimetic macrocycle has the formula:

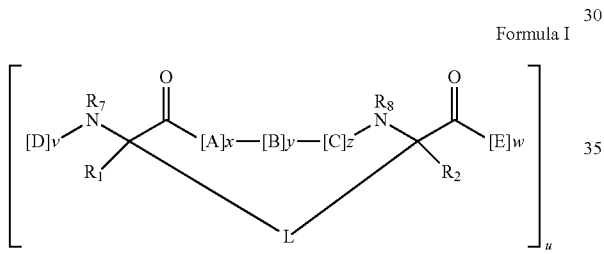

Formula I wherein:
  each A, C, D, and E is independently a natural or non-natural amino acid, and each D or E independently optionally includes a capping group;
  each B is independently a natural or non-natural amino acid, amino acid analog, or

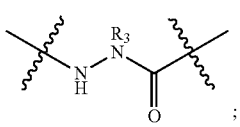

each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-;
  each $R_3$ is independently hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;
  each L is independently a macrocycle-forming linker of the formula -$L_1$-$L_2$-;
  each $L_1$ and $L_2$ is independently alkylene, alkenylene, alkynylene, heteroalkylene, cycloalkylene, heterocycloalkylene, cycloarylene, heterocycloarylene, or [—$R_4$—K—$R_4$—]$_n$, each optionally substituted with $R_5$;
  each $R_4$ is independently alkylene, alkenylene, alkynylene, heteroalkylene, cycloalkylene, heterocycloalkylene, arylene, or heteroarylene;
  each K is independently O, S, SO, $SO_2$, CO, $CO_2$, or $CONR_3$;
  each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
  each $R_6$ is independently —H, alkyl, alkenyl, alkynyl, arylalkyl, cycloalkylalkyl, heterocycloalkyl, a fluorescent moiety, a radioisotope or a therapeutic agent;
  each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, each optionally substituted with $R_5$, or forms part of a cyclic structure with a D residue;
  each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, each optionally substituted with $R_5$, or forms part of a cyclic structure with an E residue;
  each v and w is independently an integer from 1-1000;
  u is an integer from 1-10;
  each x, y and z is independently an integer from 0-10; and
  each n is independently an integer from 1-5.

5. The method of claim 4, wherein D comprises the capping group.

6. The method of claim 4, wherein E comprises the capping group.

7. The method of claim 6, wherein the capping group comprises an amino group.

8. The method of claim 4, wherein the peptidomimetic macrocycle comprises an α-helix.

9. The method of claim 4, wherein the peptidomimetic macrocycle comprises an α,α-disubstituted amino acid.

10. The method of claim 4, wherein $L_1$ and $L_2$ are independently $C_3$-$C_6$ alkenylene.

11. The method of claim 4, wherein $R_1$ and $R_2$ are methyl.

* * * * *